US009637528B2

(12) United States Patent
Bradbury et al.

(10) Patent No.: US 9,637,528 B2
(45) Date of Patent: *May 2, 2017

(54) METHOD OF GENERATING PLOYNUCLEOTIDES ENCODING ENHANCED FOLDING VARIANTS

(75) Inventors: Andrew M. Bradbury, Santa Fe, NM (US); Csaba Kiss, Los Alamos, NM (US); Geoffrey S. Waldo, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 853 days.

This patent is subject to a terminal disclaimer.

(21) Appl. No.: 12/286,967

(22) Filed: Oct. 2, 2008

(65) Prior Publication Data

US 2009/0142820 A1    Jun. 4, 2009

Related U.S. Application Data

(60) Continuation-in-part of application No. 11/900,551, filed on Sep. 11, 2007, now abandoned, which is a division of application No. 10/423,688, filed on Apr. 24, 2003, now Pat. No. 7,271,241, which is a continuation-in-part of application No. 10/132,067, filed on Apr. 24, 2002, now abandoned.

(51) Int. Cl.
| | | |
|---|---|---|
| *C07K 14/435* | (2006.01) | |
| *C07K 16/00* | (2006.01) | |
| *C12N 15/10* | (2006.01) | |
| *G01N 33/533* | (2006.01) | |
| *G01N 33/58* | (2006.01) | |

(52) U.S. Cl.
CPC ........ *C07K 14/43595* (2013.01); *C07K 16/00* (2013.01); *C12N 15/1058* (2013.01); *G01N 33/533* (2013.01); *G01N 33/582* (2013.01); *C07K 2317/565* (2013.01)

(58) Field of Classification Search
None
See application file for complete search history.

(56) References Cited

U.S. PATENT DOCUMENTS

| 7,910,700 B2 * | 3/2011 | Bradbury | ......... | C07K 14/43595 530/350 |
| 8,168,411 B2 * | 5/2012 | Bradbury | ......... | C07K 14/43595 435/252.33 |

OTHER PUBLICATIONS

Cabantous et al. (PLoS One, vol. 3, iss. 6, pp. 1-10, 2008).*
Dublet et al. (JBC, vol. 274, No. 27, 1999, pp. 18909-18915.*
Zhang et al. (Gene, vol. 350, 2005, pp. 25-31).*
Prabha et al. (FEBS Letters, vol. 557, pp. 69-72, 2004) Pang et al. (Current Biology, vol. 8, pp. 405-408, 1998).*

Stemmer, William P.C., "Rapid Evolution of a Protein In Vitro by DNA Shuffling," Nature 370, 389 (1994).
Stemmer, William P.C., "DNA Shuffling by Random Fragmentation and Reassembly: In Vitro Recombination for Molecular Evolution," Proc. Natl. Acad. Sci. USA 91, 10747 (1994).
Stemmer, William P.C., "Searching Sequence Space: Using Recombination to Search More Efficiently and Thoroughly Instead of Making Bigger Combinatorial Libraries," Biotechnology 13, 549 (1995).
Arnold, Francis H. "Directed Evolution: Creating Biocatalysts for the Future," by Frances H. Arnold, Chemical Engineering Science 51, 5091 (1996).
Zhang, Ji-Hu, et al., "Directed Evolution of a Fucosidase From a Galactosidase by DNA Shuffling and Screening," Proc. Natl. Acad. Sci. USA 94, 4504 (1997).
Zhao, H. and Arnold, Frances, "Functional and Nonfunctional Mutations Distinguished by Random Combination of Homologous Genes," by Proc. Natl. Acad. Sci. USA 94, 7997 (1997).
Moore, J. et al., "Strategies for the In Vitro Evolution of Protein Function: Enzyme Evolution by Random Recombination of Improved Sequences", J. Mol. Biol. 272, 336-346 (1997).
Zacchi, P., et al. "Selecting open reading frames from DNA", Genome Res 13, 980-90, (2003).
Maxwell, K. L. et al., "A simple in vivo assay for increased protein solubility", Protein Sci. 8, 1908-11, (1999).
Lutz, S.et al., (2002) "A universal, vector-based system for nucleic acid reading-frame selection", Protein Eng 15, 1025-30.
Fisher, A. C., et al, (2006) "Genetic selection for protein solubility enabled by the folding quality control feature of the twin-arginine translocation pathway", Protein Sci 15, 449-58.
Nakayama, M. & Ohara, O. (2003). "A system using convertible vectors for screening soluble recombinant proteins produced in Escherichia coli from randomly fragmented cDNAs", Biochem Biophys Res Commun 312, 825-30.
Liu, J. W., et al., (2006). "Improving protein solubility: the use of the *Escherichia coli* dihydrofolate reductase gene as a fusion reporter", Protein Expr Purif 47, 258-63.
Waldo, G. S., Standish, B. M., Berendzen, J. & Terwilliger, T. C. (1999). Rapid protein-folding assay using green fluorescent protein. Nat. Biotechnol. 17, 691-5.
Wigley, W. C., et al., (2001). "Protein solubility and folding monitored in vivo by structural complementation of a genetic marker protein" Nat Biotechnol 19, 131-6.

(Continued)

*Primary Examiner* — Hope Robinson
(74) *Attorney, Agent, or Firm* — Klarquist Sparkman, LLP

(57) ABSTRACT

The invention provides directed evolution methods for improving the folding, solubility and stability (including thermostability) characteristics of polypeptides. In one aspect, the invention provides a method for generating folding and stability-enhanced variants of proteins, including but not limited to fluorescent proteins, chromophoric proteins and enzymes. In another aspect, the invention provides methods for generating thermostable variants of a target protein or polypeptide via an internal destabilization baiting strategy. Internally destabilization a protein of interest is achieved by inserting a heterologous, folding-destabilizing sequence (folding interference domain) within DNA encoding the protein of interest, evolving the protein sequences adjacent to the heterologous insertion to overcome the destabilization (using any number of mutagenesis methods), thereby creating a library of variants. The variants in the library are expressed, and those with enhanced folding characteristics selected.

3 Claims, 28 Drawing Sheets

(56) References Cited

OTHER PUBLICATIONS

Pedelacq, J. D. et al.,(2002) "Engineering soluble proteins for structural genomics" *Nat Biotechnol* 20, 927-32.
Arnold, F. H. et al, (1999) "Directed evolution of mesophilic enzymes into their thermophilic counterparts" *Ann N Y Acad Sci* 870, 400-3.
Giver, L. et al., (1998) "Directed evolution of a thermostable esterase" *Proc Natl Acad Sci U S A* 95, 12809-13.
Fridjonsson, O. et al., (2002), "Thermoadaptation of alpha-galactosidase AgaB1 in Thermus thermophilus" *J Bacteriol* 184, 3385-91.
Nakamura, A. et al., (2005) "In vivo directed evolution for thermostabilization of *Escherichia coli* hygromycin B phosphotransferase and the use of the gene as a selection marker in the host-vector system of Thermus thermophilus" *J Biosci Bioeng* 100, 158-63.
Sieber, V. et al., (1998) "Selecting proteins with improved stability by a phage-based method" *Nat Biotechnol* 16, 955-60.
Kristensen, P. & Winter, G. (1998) "Proteolytic selection for protein folding using filamentous bacteriophages" *Fold Des* 3, 321-8.
Wunderlich, M. & Schmid, F. X. (2006), "In vitro evolution of a hyperstable Gbeta1 variant", *J Mol Biol* 363, 545-57.
Wunderlich, M. et al., (2005), Evolutionary protein stabilization in comparison with computational design. *J Mol Biol* 351, 1160-8.
Wunderlich, M. et al., (2005) "Stabilization of the cold shock protein CspB from Bacillus subtilis by evolutionary optimization of Coulombic interactions", *J Mol Biol* 347, 1063-76.
Martin, A. et al., (2003), "Proside: a phage-based method for selecting thermostable proteins", *Methods Mol Biol* 230, 57-70.
Martin, A. & Schmid, F. X. (2003) "Evolutionary stabilization of the gene-3-protein of phage fd reveals the principles that govern the thermodynamic stability of two-domain proteins", *J Mol Biol* 328, 863-75.
Martin, A. et al., (2001), In-vitro selection of highly stabilized protein variants with optimized surface. *J Mol Biol* 309, 717-26.
Shusta, E. V. et al., (1999) "Yeast polypeptide fusion surface display levels predict thermal stability and soluble secretion efficiency", *J. Mol. Biol*. 292, 949-56.
Park, S. et al., (2006), "Limitations of yeast surface display in engineering proteins of high thermostability" *Protein Eng Des Sel* 19, 211-7.
Steipe, B. (2004). "Consensus-based engineering of protein stability: from intrabodies to thermostable enzymes" *Methods Enzymol* 388, 176-86.
Steipe, B. et al., (1994), "Sequence statistics reliably predict stabilizing mutations in a protein domain" *J. Mol. Biol*. 240, 188-92.
Knappik, A. et al., (2000), "Fully synthetic human combinatorial antibody libraries (HuCAL) based on modular consensus frameworks and CDRs randomized with trinucleotides", *J. Mol. Biol*. 296, 57-86.
Lehmann, M. et al., (2002), "The consensus concept for thermostability engineering of proteins: further proof of concept", *Protein Eng* 15, 403-11.
Lehmann, M. & Wyss, M. (2001), "Engineering proteins for thermostability: the use of sequence alignments versus rational design and directed evolution", *Curr Opin Biotechnol* 12, 371-5.
Lehmann, M. et al., (2000), "The consensus concept for thermostability engineering of proteins", *Biochim Biophys Acta* 1543, 408-415.
Lehmann, M. et al., (2000), "From DNA sequence to improved functionality: using protein sequence comparisons to rapidly design a thermostable consensus phytase", *Protein Eng* 13, 49-57.
Devi, V. S. et al, (2004), "Folding of a designed simple ankyrin repeat protein", *Protein Sci* 13, 2864-70.
Kohl, A. et al., (2003), "Designed to be stable: Crystal structure of a consensus ankyrin repeat protein", *Proc Natl Acad Sci U S A* 100, 1700-5.
Main, E. R. et al., (2003), "The folding and design of repeat proteins: reaching a consensus", *Curr Opin Struct Biol* 13, 482-9.
Dai, M. et al., (2007), "The creation of a novel fluorescent protein by guided consensus engineering", *Protein Eng Des Sel* 20, 69-79.
Binz, H. K. et al., (2004), "High-affinity binders selected from designed ankyrin repeat protein libraries", *Nat Biotechnol* 22, 575-82.
Bloom, J. D. et al., (2006), "Protein stability promotes evolvability", *Proc Natl Acad Sci U S A* 103, 5869-74.
Pedelacq, J. D. et al., (2006), "Engineering and characterization of a superfolder green fluorescent protein", *Nat Biotechnol* 24, 79-88.
Crameri, A. et al., (1996), "Improved Green Fluorescent Protein by Molecular Evolution Using DNA Shuffling", Nature Biotechnology 14, 315.
Macbeath, G. et al., (1998), "Redesigning enzyme topology by directed evolution", Science 279, 1958-1961.
Martineau, P. et al., (1998), "Expression of an antibody fragment at high levels in the bacterial cytoplasm", J. Mol. Biol. 280, 117-127.
Proba, K. et al., (1998), "Antibody scFv fragments without disulfide bonds made by molecular evolution", J. Mol. Biol. 275, 245-253.
Zhanglin, L. et al., (1999), "Functional Expression of Horseradish Peroxidase in *E. coli* by Directed Evolution", Biotechnol. Prog. 15, 467-471.

\* cited by examiner

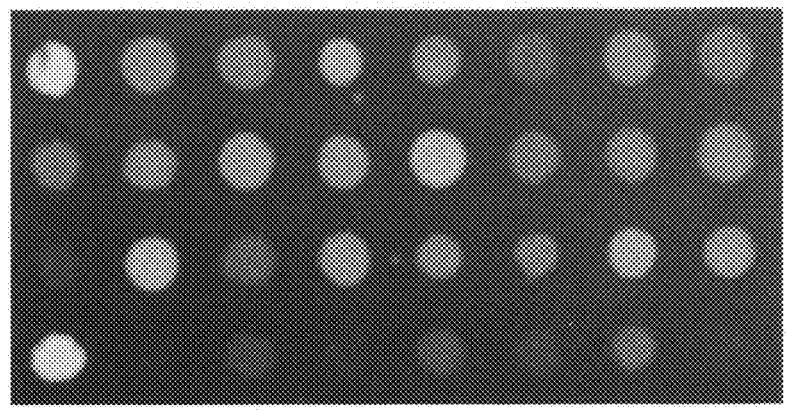
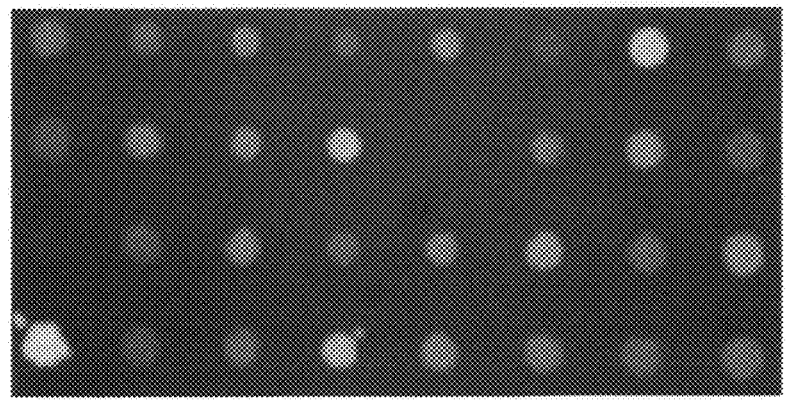
FIG. 1B

FIG. 3

```
          ----------10--------|--------20-------|--------30--------|--------40--------|--------50--------|--------60--------|--------70--------|--------80--------|--------90--------|-------100--------|-------110-------120
                              ---------1--------|--------2----7----|------------------|--------3---------|-----------113----|------------------|--------2---------|------------------|------------------|----------6-------
    CGP                       MSVIKPDMKIKLRMEGAV|NGHKFVIEGEGKPFEGTQMDLTVKEGAPLPFAYDILTVFQYGNRAFAKYPKDIPDYFKQTPPEGYSWERSMTYE|DQGICIATSDITMEGDCFFYKIRF
    eCGP1                     MSVIKPEMKIKLRMEGAV|NGHKFVIEGEGKGNPFEGTQTLDLTVKEGAPLPFAYDILTPVFQYGNRAFAKYPQDIPDYFKQTPEGYSWERSMTYE|DHGICIATSDITMEGDCFIYKIRF
    eCGP13                    MSVIKPEMKIKLRMEGAV|NGHKFVIEGEGKPFEGTQTLDLTVKEGAPLPFAYDILTPVFQYGNRAFTKYPQDIPDYFKQTFPEGYSWERSMTYE|DHGICIATSDITMEGDCFIYKIRF
    eCGP2                     MSVIKPEMKIKLRLEGAV|NGHEFVIEGEGKGKPFEGTQTLDLTVKEGAPLPFAYDILTPAFQYGNRAFAKYPKDIPDYFKQTPPEGYSWERSMTYE|DQGICIATSDITMEGDCFFYKIRF
    eCGP23                    MSVIKPEMKIKLRLEGAV|NGHEFVIEGEGKGKPFEGTQTLDLTVKEGAPLPFAYDILTPAFQYGNRAFTKYPKDIPDYFKQTPEGYSWERSMTYE|DQGICIATSDITMEGDCFFYKIRF
    eCGP123                   MSVIKPEMKIKLRMEGAV|NGHKFVIEGEGIGKPYEGTQTLDLTVKEGAPLPFSYDILTPAFQYGNRAFTKYPKDIPDYFKQAFPEGYSWERSMTYE|DQGICIATSDITMEGDCFFYKIRF

-------130--------|-------140--------|-------150--------|-------160--------|---170-----------|-------180-------|-------190-------|-------200-------|-------210-------|-------220
                                                                                                      ---------4------------------
    CGP                       DGTNFPPNGPVMQKKTLKWEPSTEKMYVRDGVLKGDVNMALLLE|GGGHYRCDFKTTYKAKKDVRLPDAHKVDHRIEILSHDKDYNKVKLYEHAEARYSMLPSQAK
    eCGP1                     DGTNFPPNGPVMQKKTLKWEPSTEKMYVRDGVLKGDVNMALLLE|GGGHYRCDFKTTYKAKKDVRLPDAHKVDHRIEILSHDKDYNKVKLYEHAEARYSMLPSQAK
    eCGP13                    DGTNFPPNGPVMQKKTLKWEPSTEKMYVRDGVLKGDVNMALLLE|GGGHYRCDFKTTYKAKKDVRLPGAHKVDHRIEILSHDKDYNKVKLYEHAEARYSMLPSQAK
    eCGP2                     DGTNFPPNGPVMQKKTLKWEPSTEKMYVRDGVLKGDVNMALLLE|GGGHYRCDFKTTYKAKKDVRLPDAHKVDHRIEILSHDKDYNKVKLYEHAEARYSMLPSQAK
    eCGP23                    DGTNFPPNGPVMQKKTLKWEPSTEKMYVRDGVLKGDVNMALLLE|GGGHYRCDFKTTYKAKKDVRLPDAHEVDHRIEILSHDKDYNKVKLYEHAEARYSMLPSQAK
    eCGP123                   DGTNFPPNGPVMQKKTLKWEPSTEKMYVRDGVLKGDVNMALLLE|GGGHYRCDFKTTYKAKKDVRLPDAHEVDHRIEILSHDKDYNKVRLYEHAEARYSMLPSQAK
```

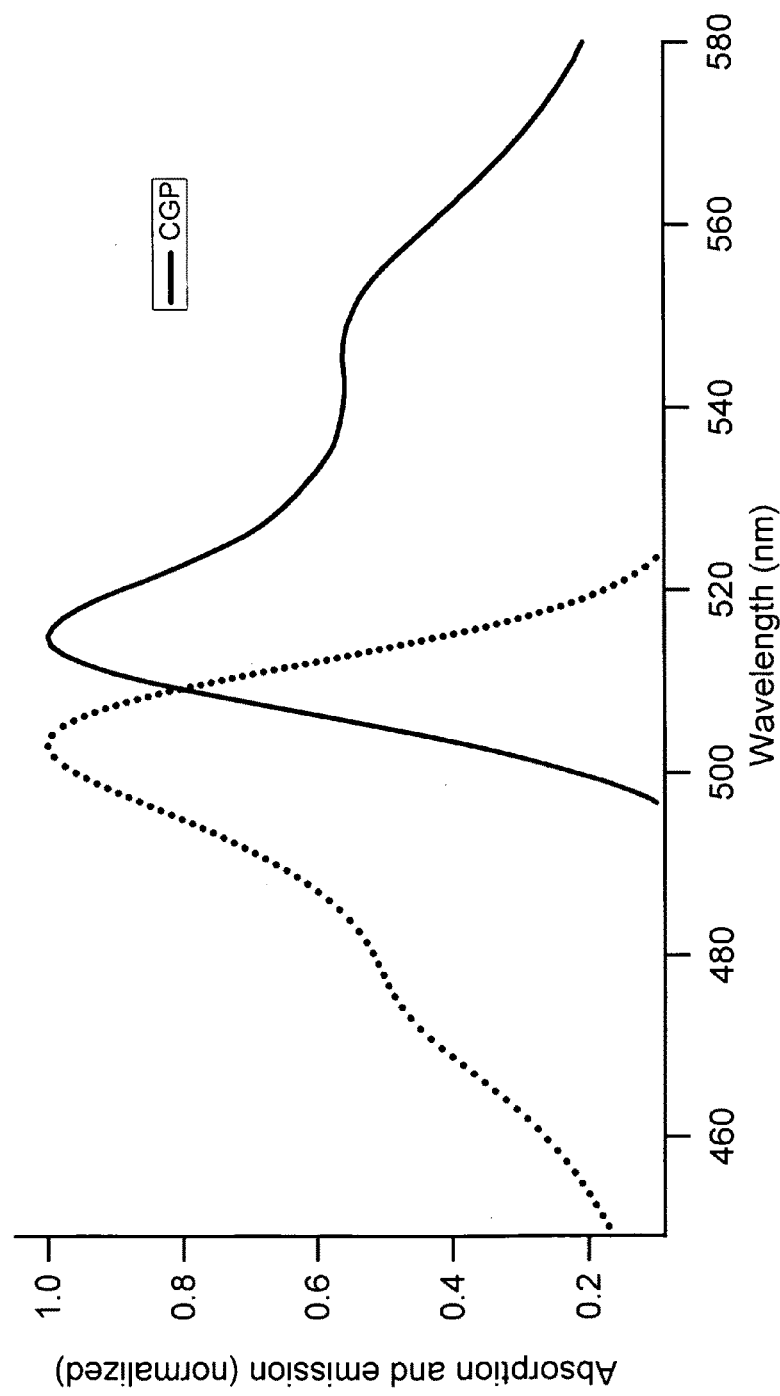
FIG. 4B-i

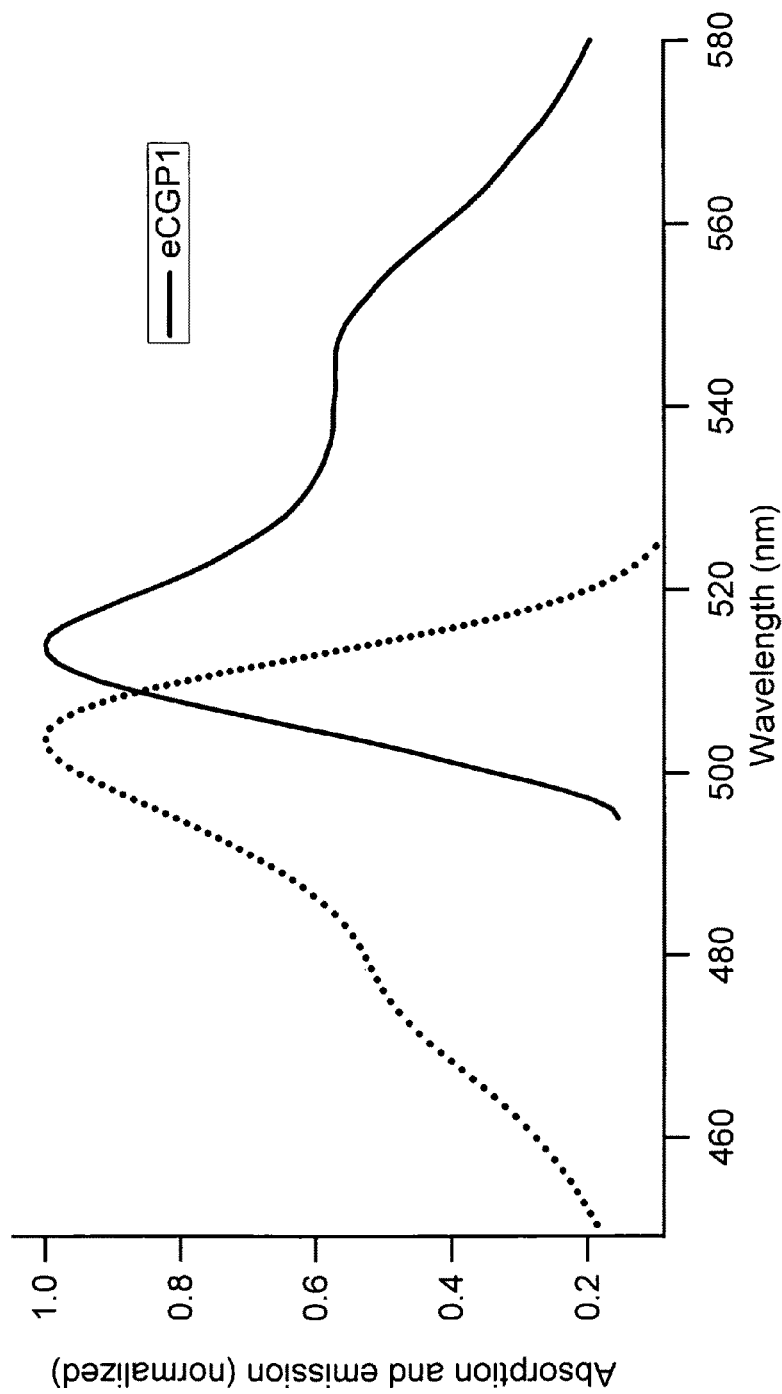
FIG. 4B-ii

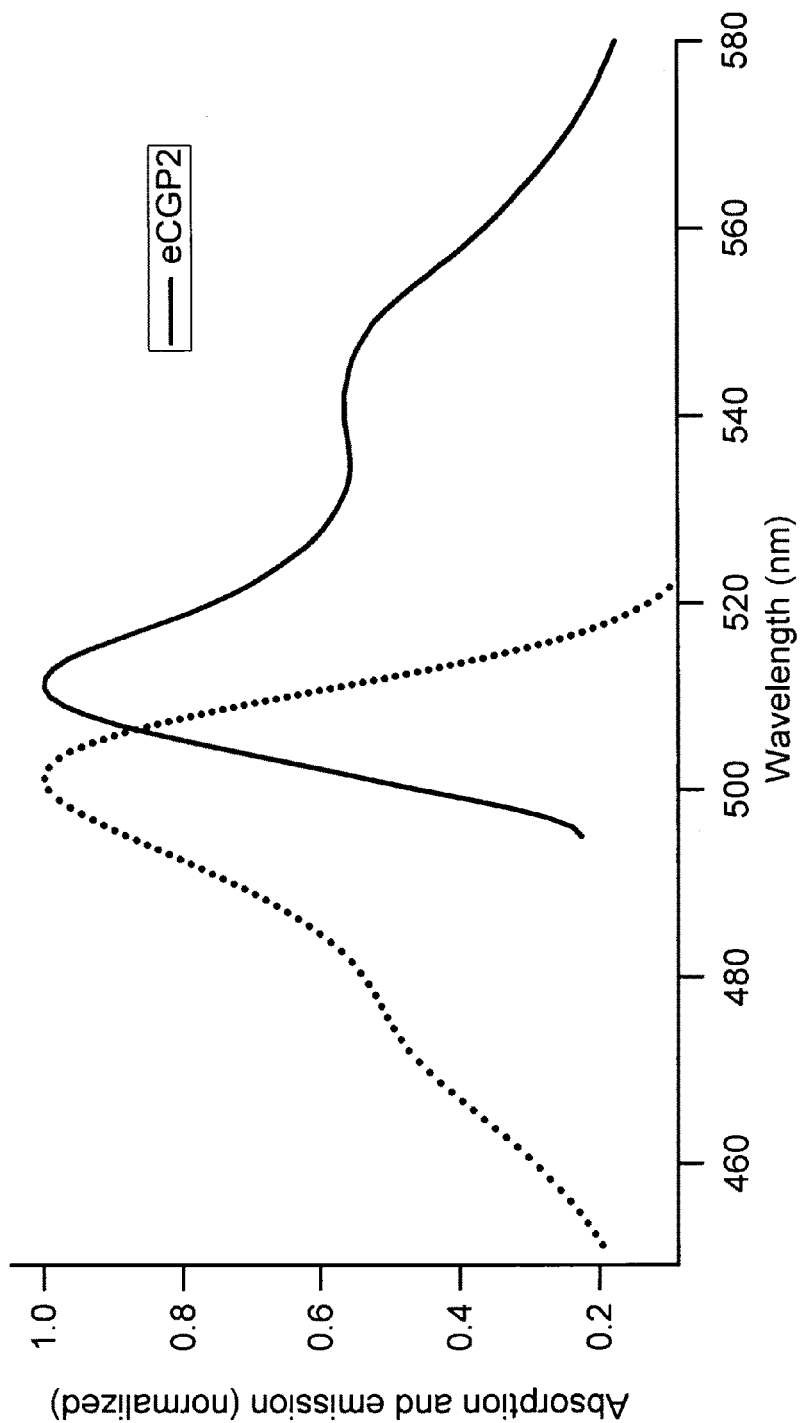
FIG. 4B-iii

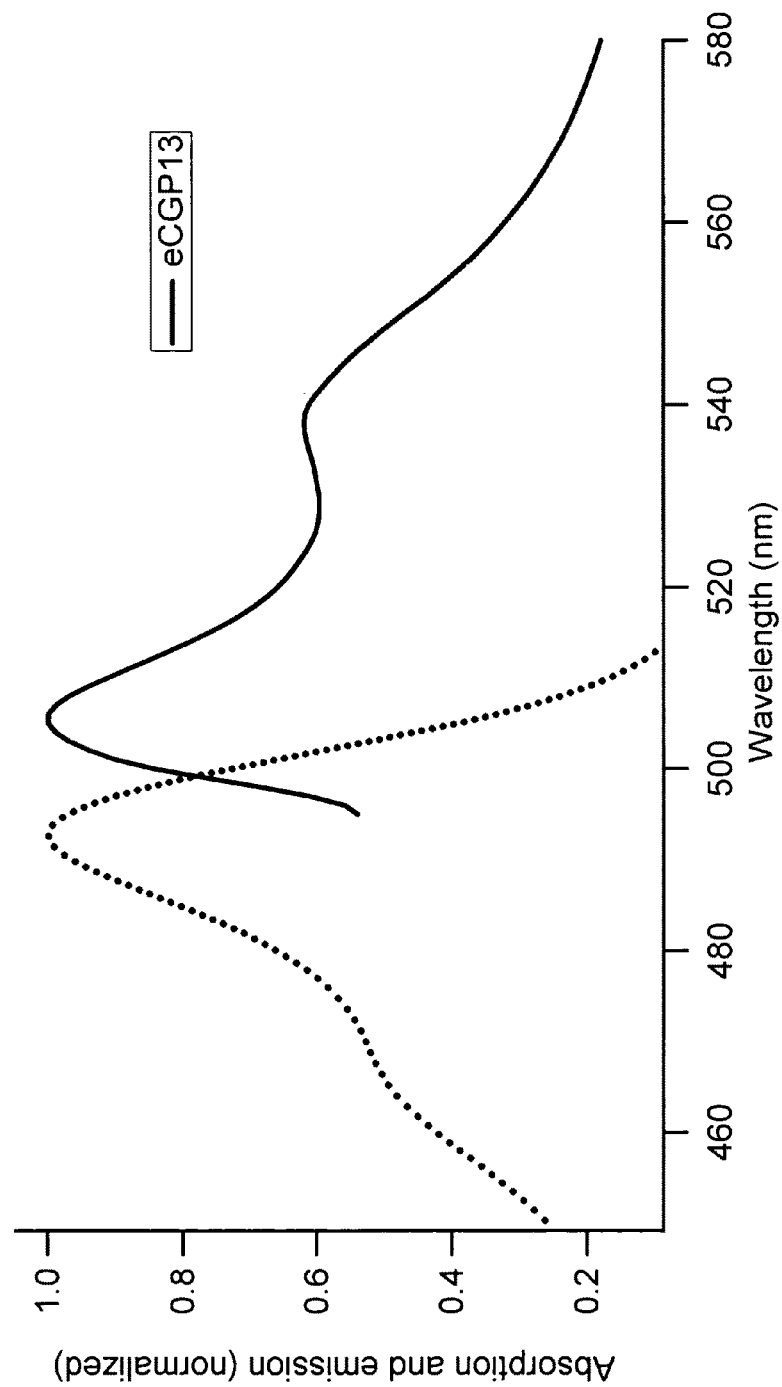
FIG. 4B-iv

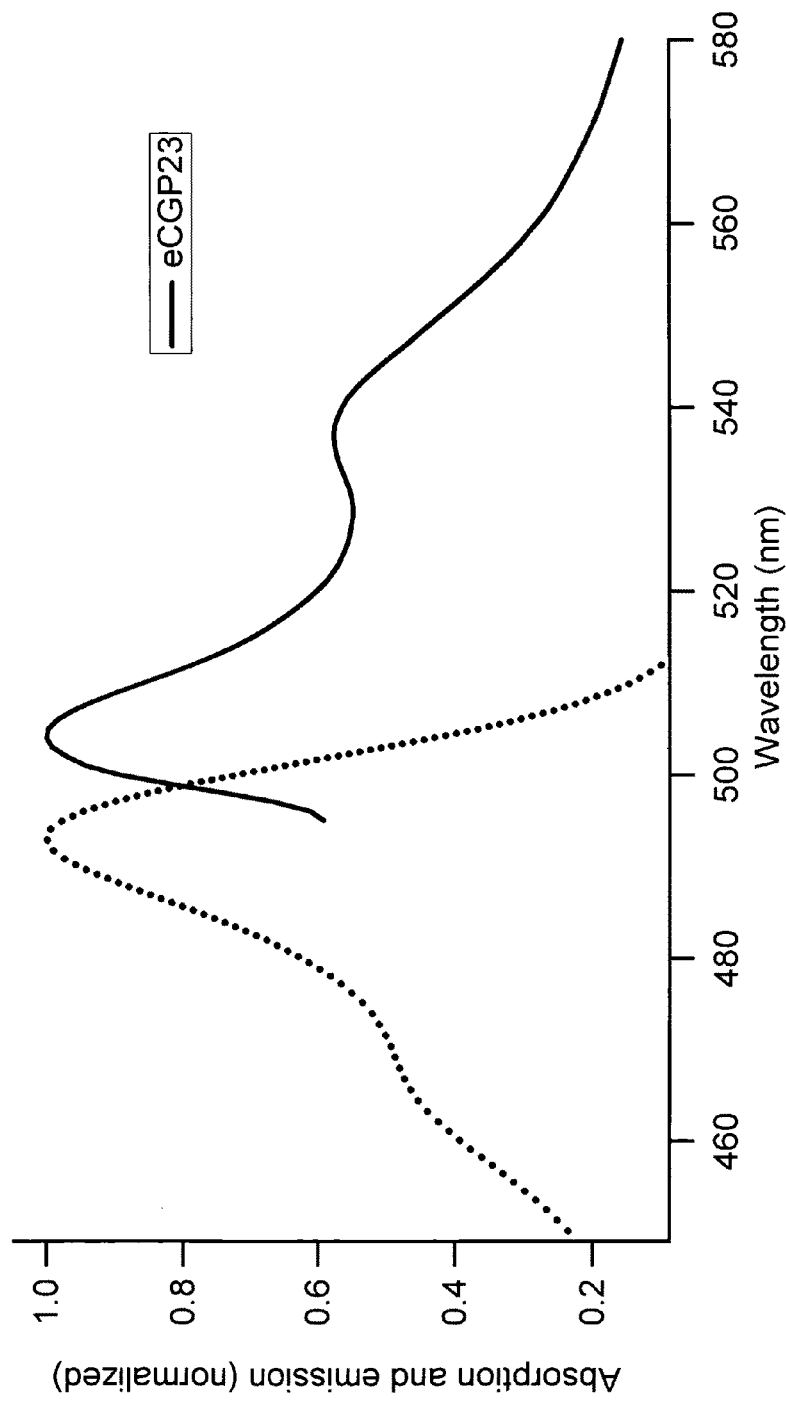
FIG. 4B-v

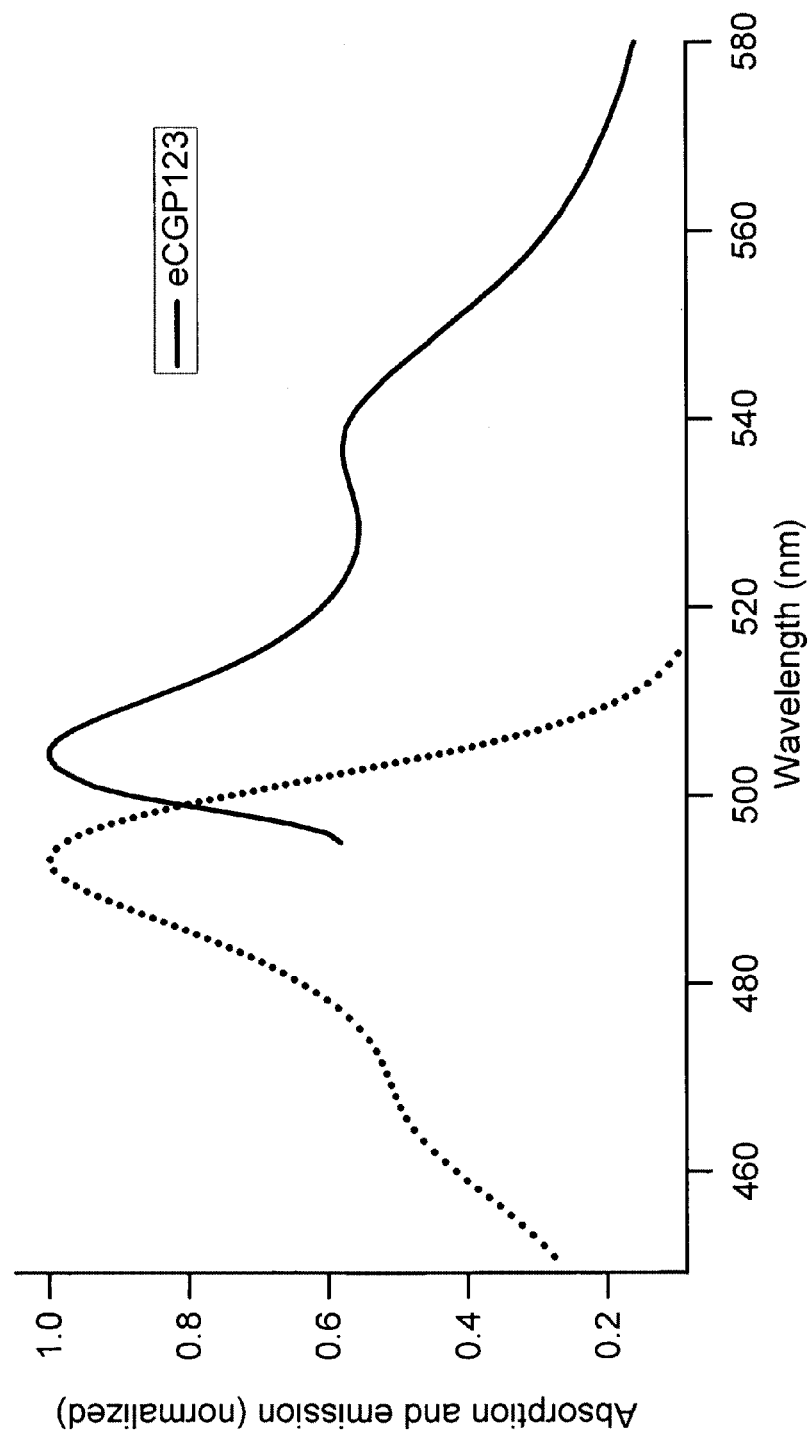
FIG. 4B-vi

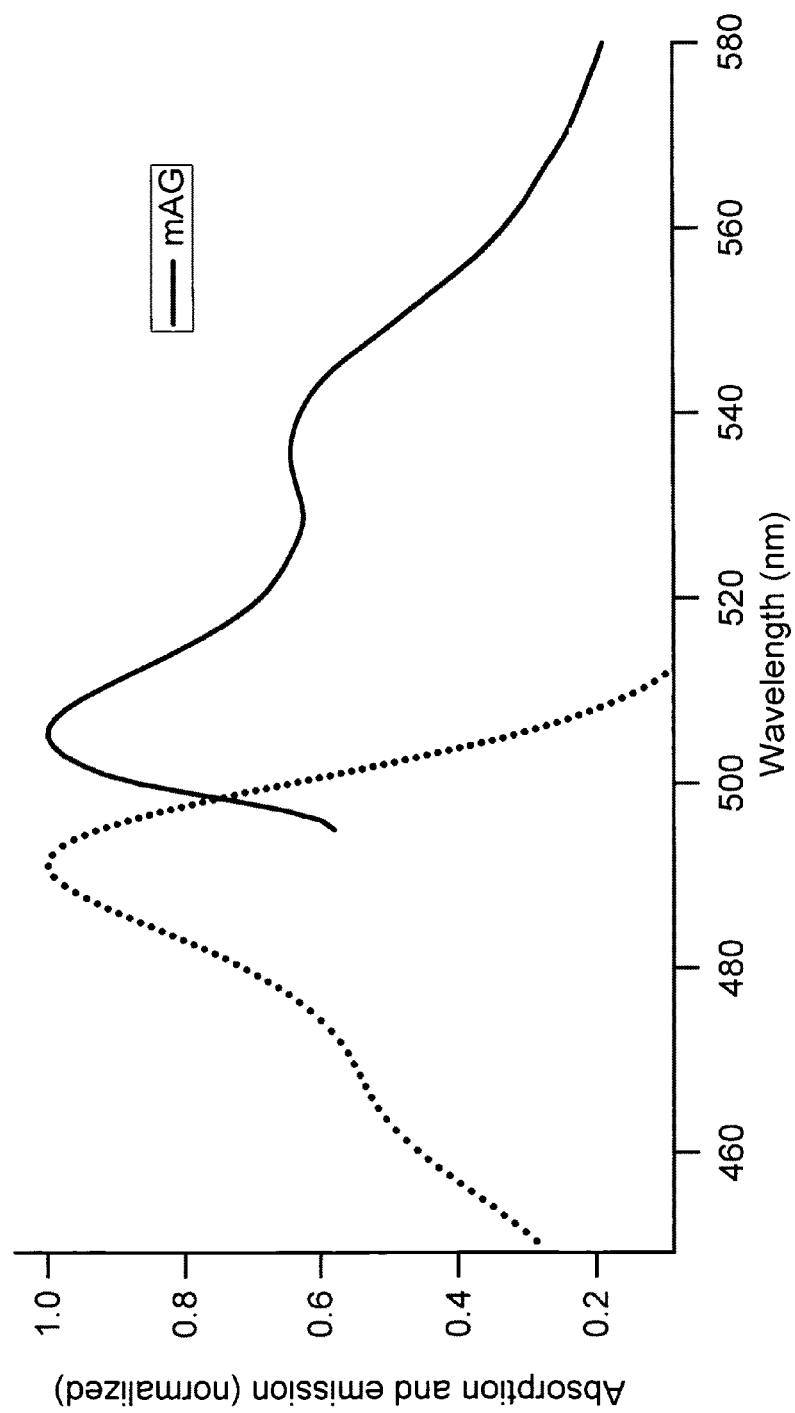
FIG. 4B-vii

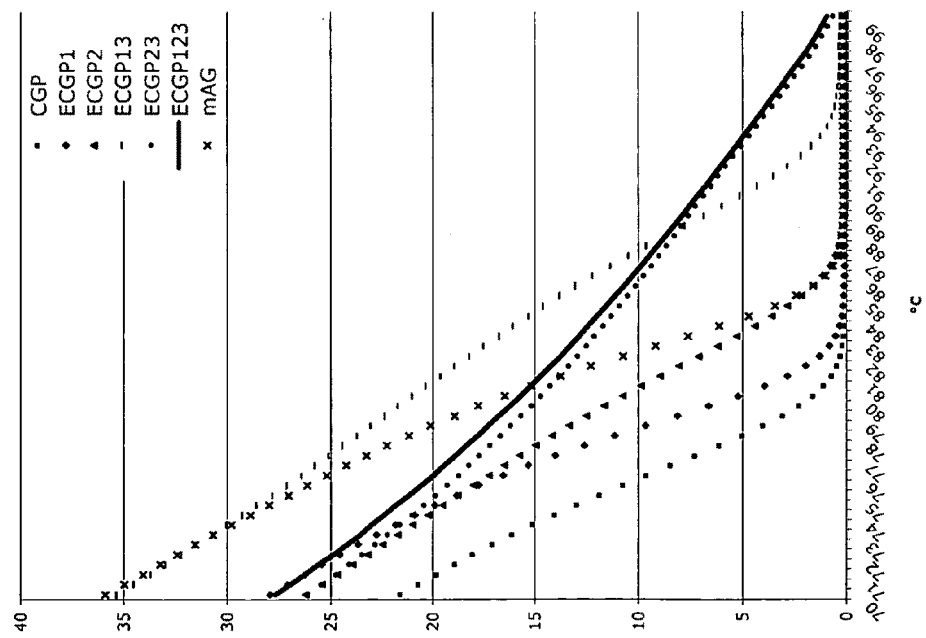

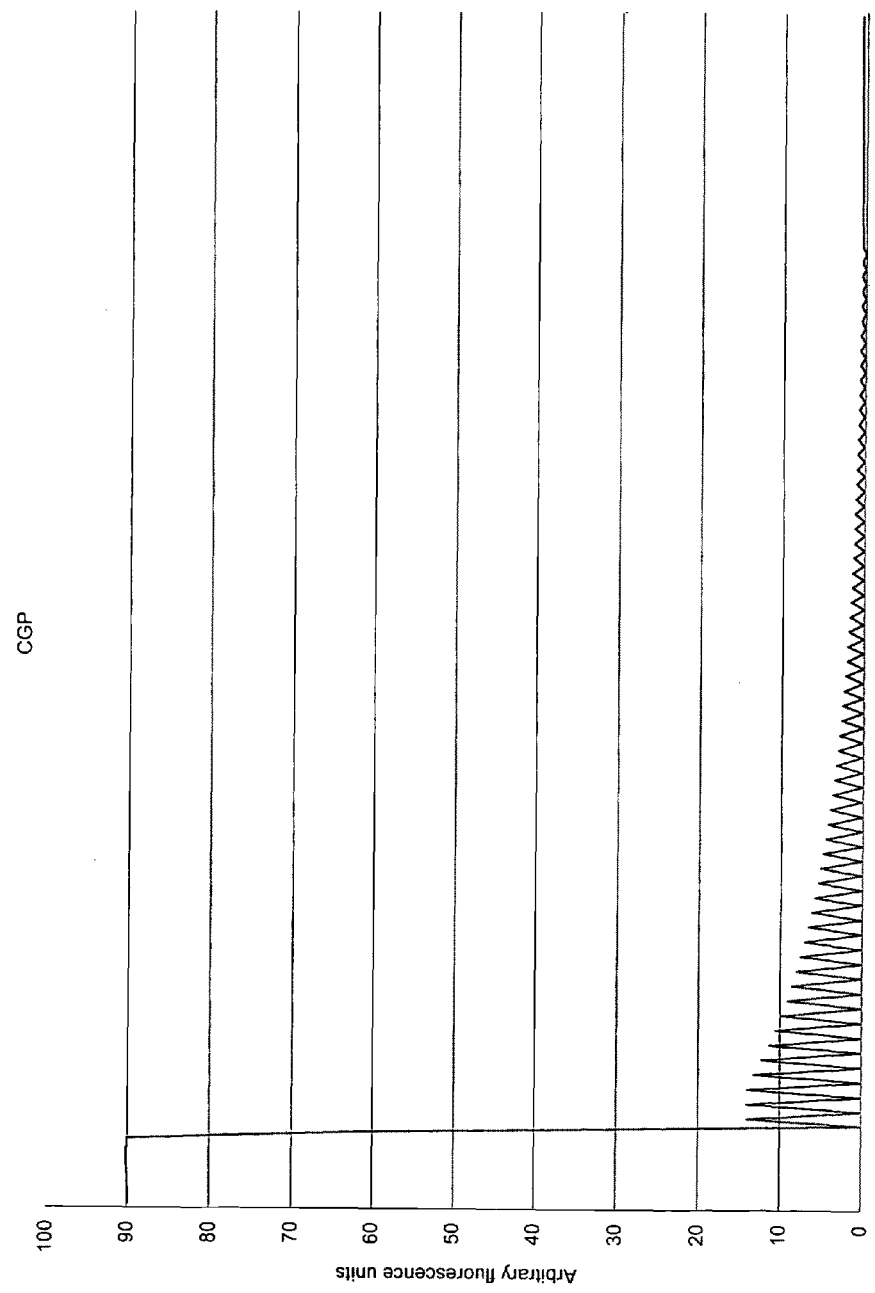

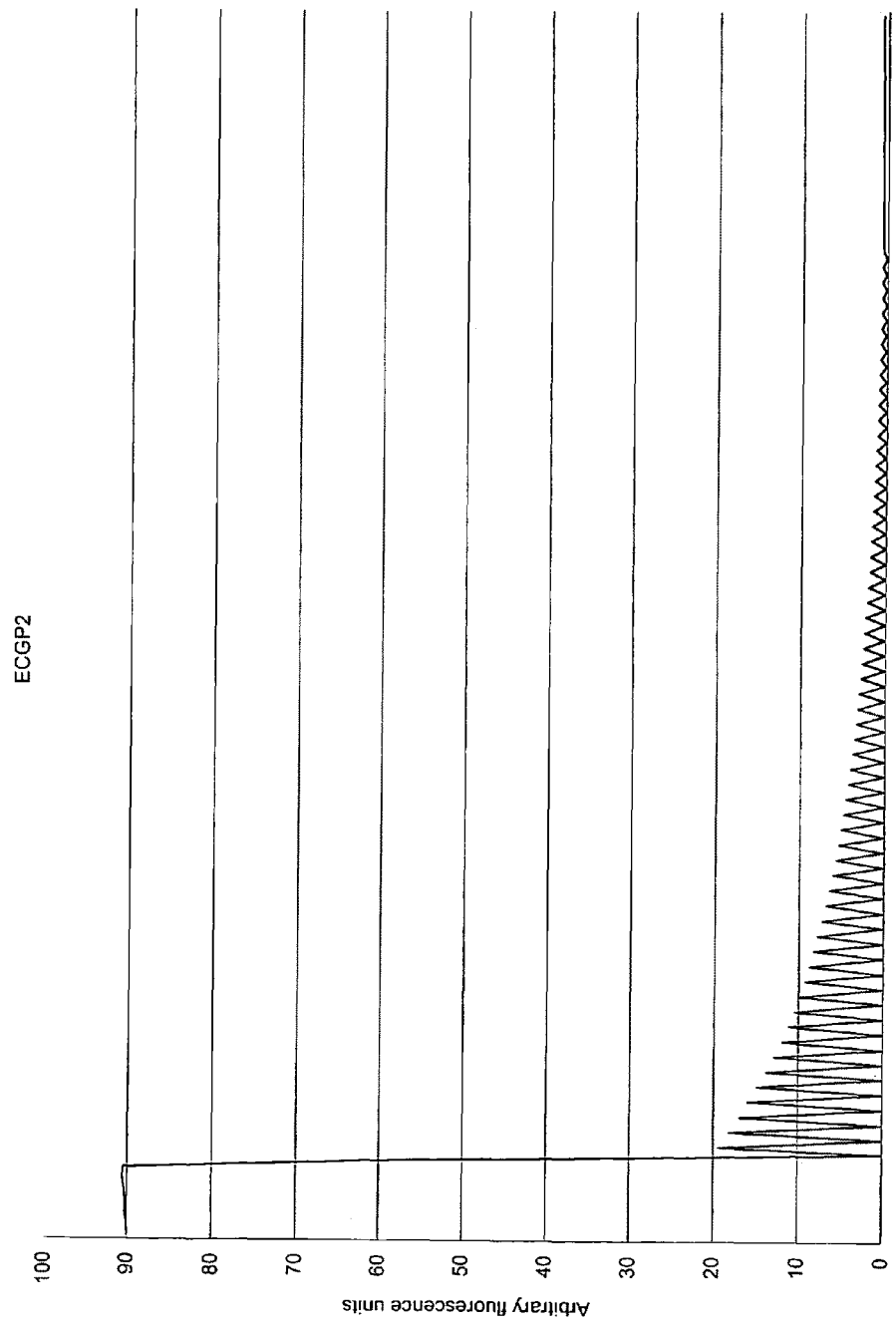

FIG. 5C-iv

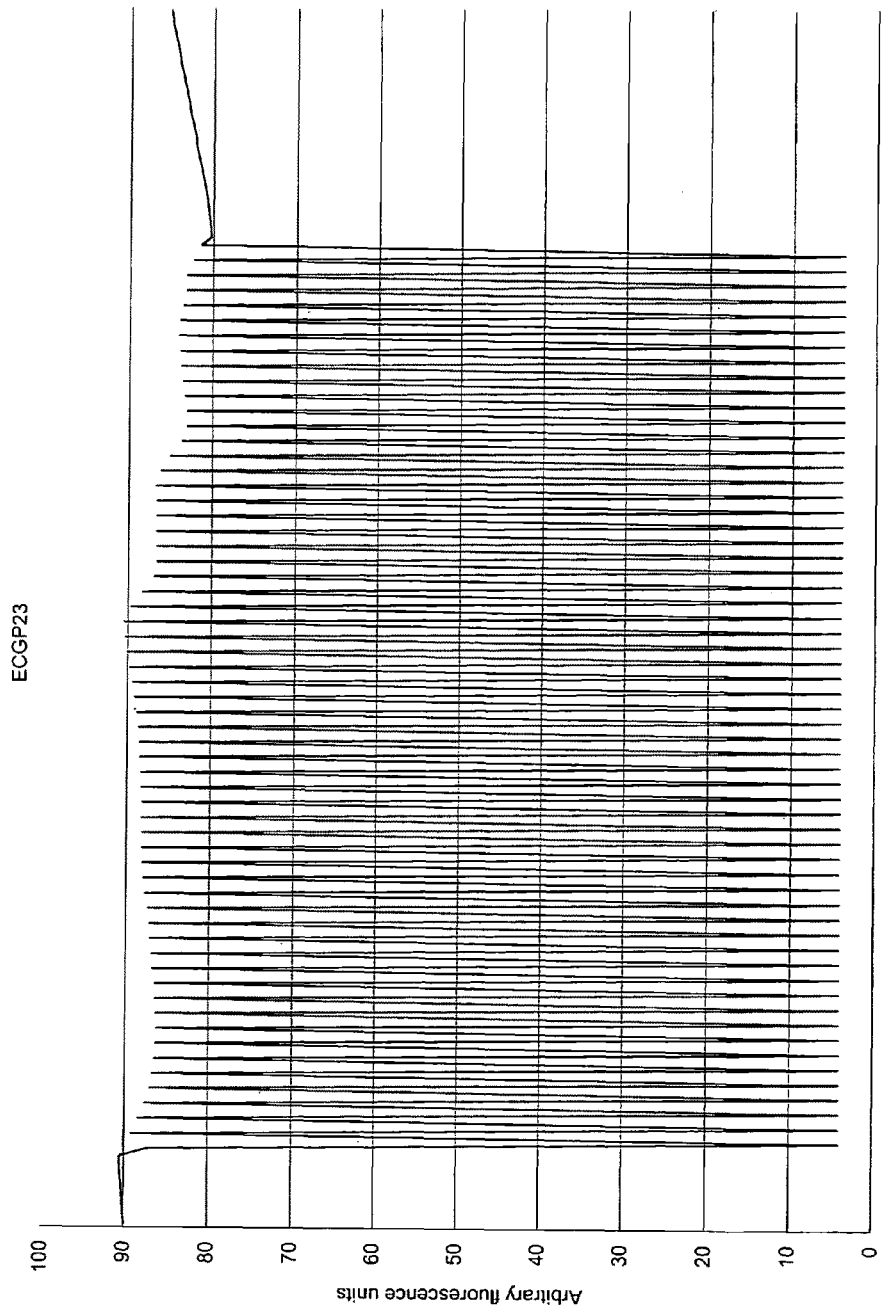
FIG. 5C-v

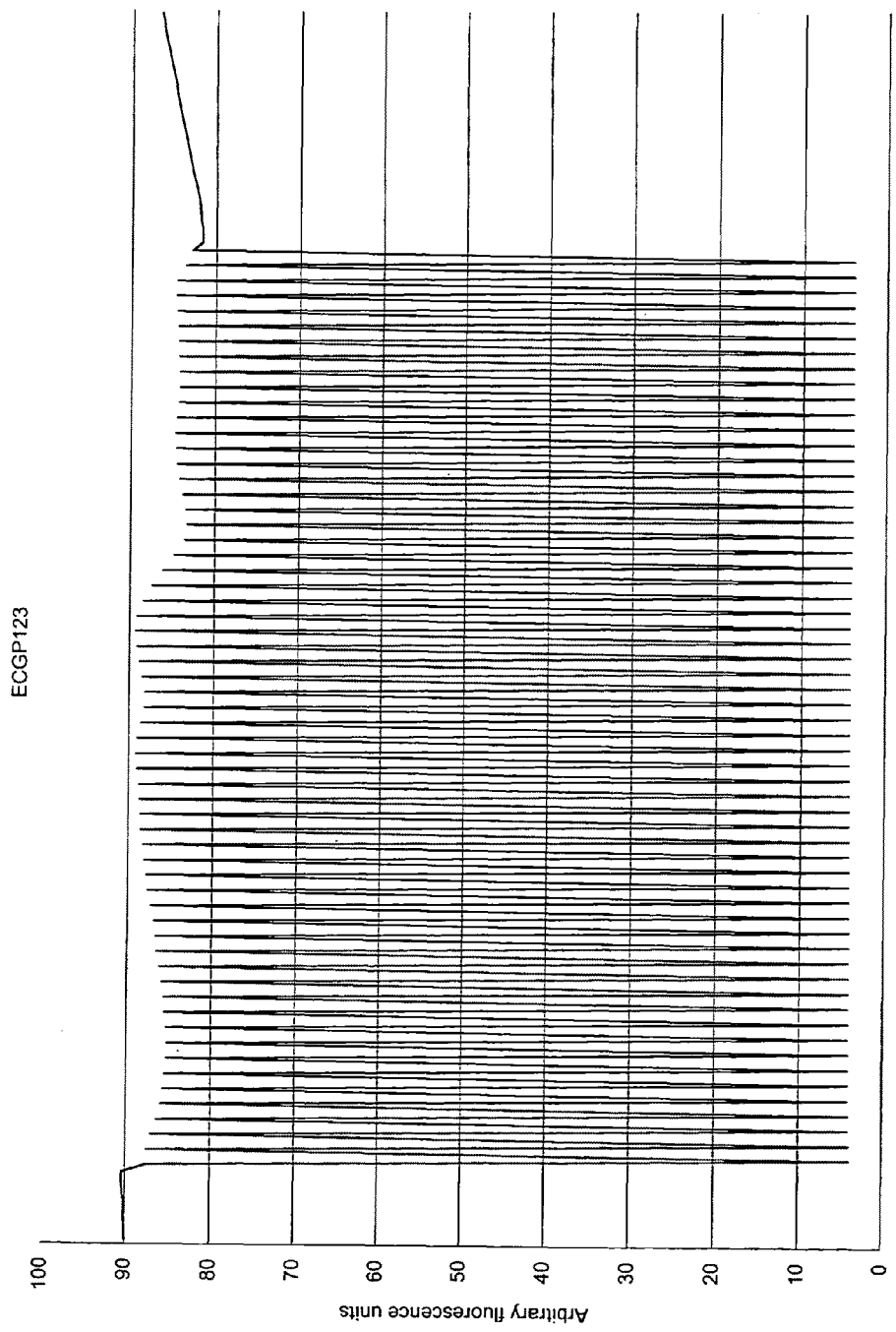
FIG. 5C-vi

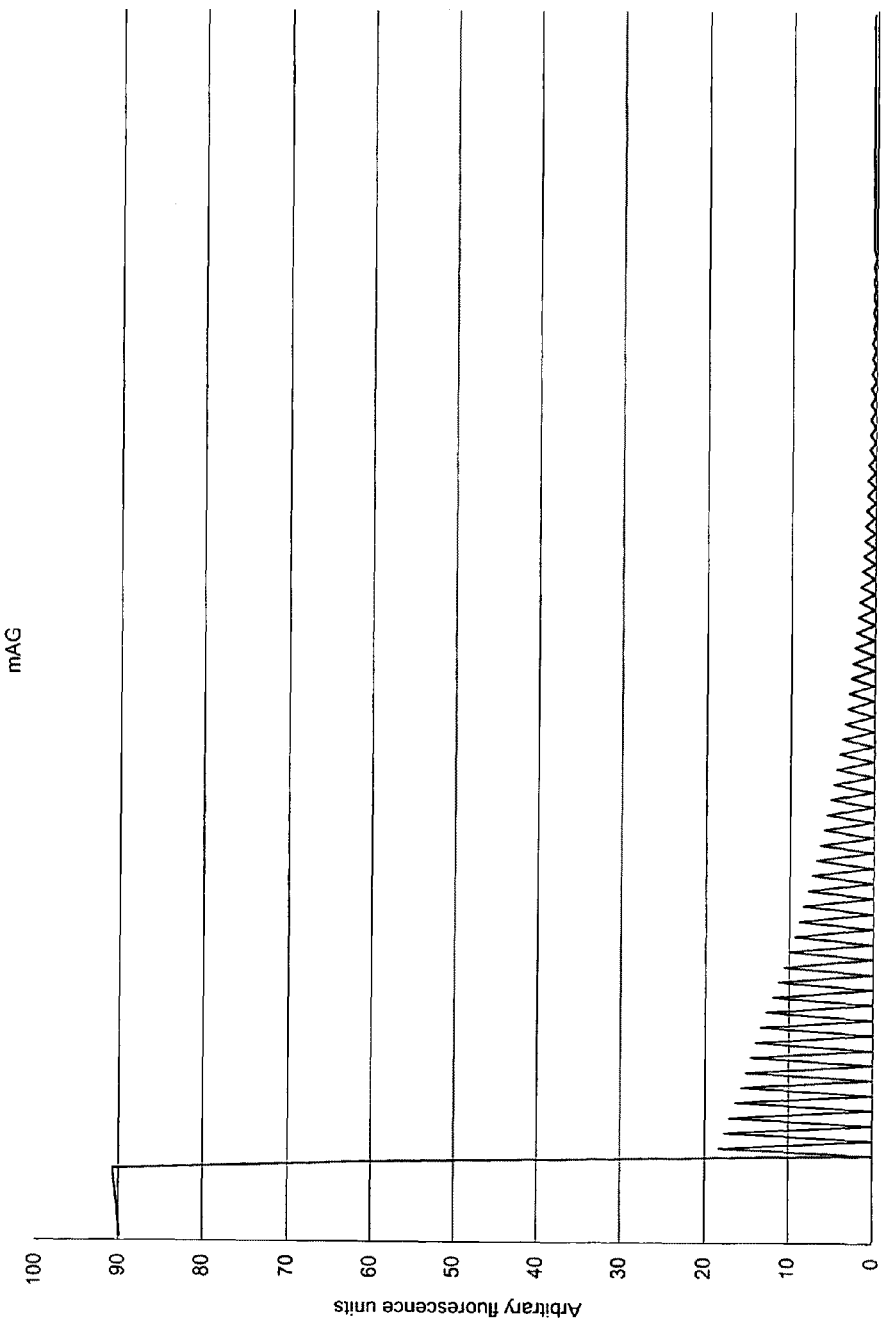
FIG. 5C-vii

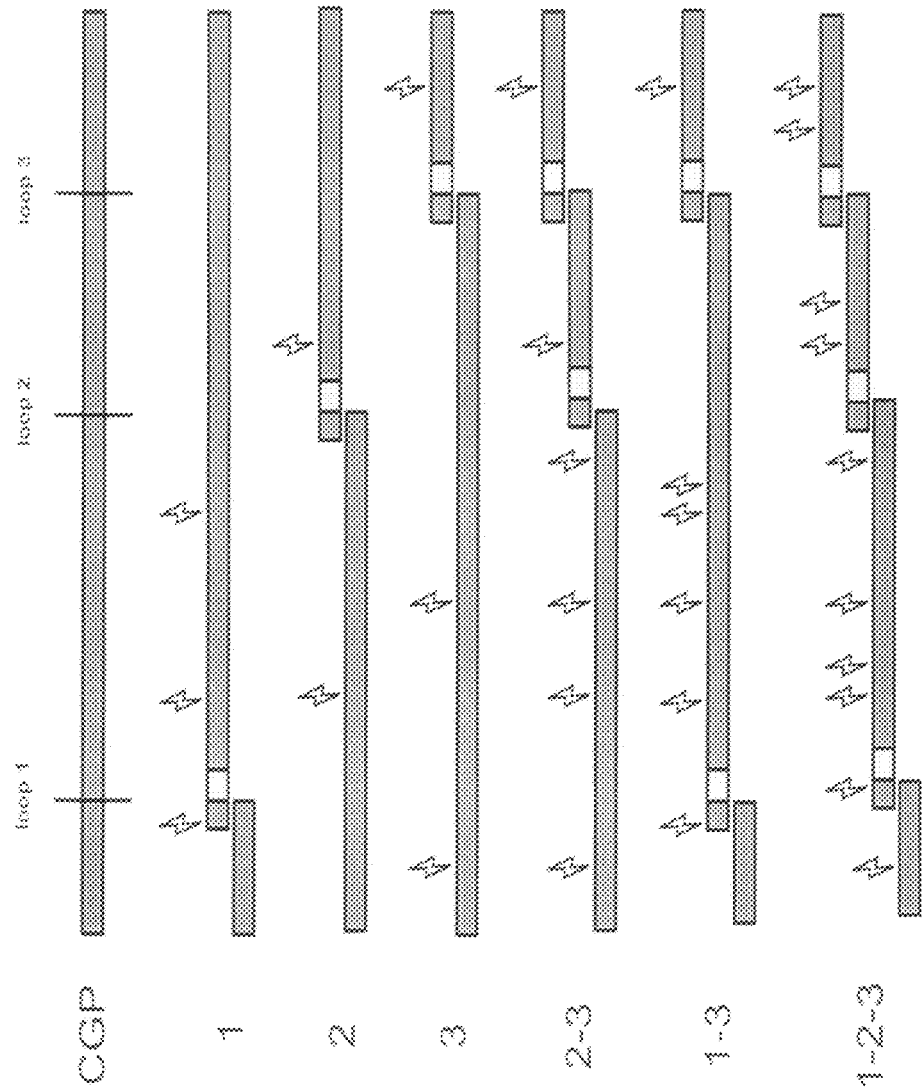

SEQUENCE LISTING

<160> NUMBER OF SEQ ID NOS: 28

<210> SEQ ID NO 1
<211> LENGTH: 681
<212> TYPE: DNA
<213> ORGANISM: Artificial
<220> FEATURE:
<223> OTHER INFORMATION: Synthetic DNA Encoding Engineered Fluorescent
    Protein

<400> SEQUENCE: 1

```
atgtcagtaa ttaaaccgga atgaaaatt aaattgcgta tggaaggtgc cgttaacggc      60
cataaatttg taattgaagg ggaaggaaaa ggcaacccat cgaaggaac ccagaccctg     120
gatttaaccg taaagaagg cgcacctctc cctttcgcgt acgacatcct caccccagtc     180
ttccaatacg gcaatcgcgc tttcgccaaa tacccacaag atattccaga ctattttaaa    240
caaacattcc ccgaaggcta ttcttgggaa cgctctatga cctatgaaga tcatggaatt    300
tgtatcgcta cctccgacat tactatggaa ggcgactgtt ttatttataa aattcgcttt    360
gatggaacta acttccccc gaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taagccaaa     540
aaagatgttc gtcttccaga tgcacacaag gtggaccacc gcattgaaat cctgagccac    600
gataaagatt ataataaagt taaactctat gaacacgccg aagcccgcta ttctatgtta    660
ccgtctcagg ctaaagctag c                                              681
```

<210> SEQ ID NO 2
<211> LENGTH: 681
<212> TYPE: DNA
<213> ORGANISM: Artificial
<220> FEATURE:
<223> OTHER INFORMATION: Synthetic DNA Encoding Engineered Fluorescent
    Protein

<400> SEQUENCE: 2

```
atgtcagtaa ttaaaccgga atgaaaatt aaattgcgtt tggaaggtgc cgttaacggc      60
catgaatttg taattgaagg agaaggaaaa ggcaaaccat cgaaggaac ccagaccctg     120
gatttaaccg taaagaagg cgcacctctc cctttcgcgt acgacatcct caccccagcc     180
ttccaatacg gcaatcgcgc tttcgccaaa tacccaaaag atattccaga ctattttaaa    240
caaacattcc ccgaaggcta ttcttgggaa cgctctatga cctatgaaga tcaaggaatt    300
tgtatcgcta cctccgacat tactatggaa ggagactgtt ttttttataa aattcgcttt    360
gatggaacta acttccccc gaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taagccaaa     540
aaagatgttc gtcttccaga tgcacacaag gtggaccacc gcattgaaat cctgagccac    600
gataaagatt ataataaagt taaactctat gaacacgccg aagcccgcta ttctatgtta    660
ccgtctcagg ctaaagctag c                                              681
```

<210> SEQ ID NO 3
<211> LENGTH: 681
<212> TYPE: DNA
<213> ORGANISM: Artificial
<220> FEATURE:
<223> OTHER INFORMATION: Synthetic DNA Encoding Engineered Fluorescent -continued Protein

<400> SEQUENCE: 3

| | |
|---|---|
| atgtcagtaa ttaaaccgga atgaaaatt aaattgcgta tggaaggtgc cgttaacggc | 60 |
| cataaatttg taattgaagg ggaaggaaaa ggcaacccat cgaaggaac ccagaccctg | 120 |
| gatttaaccg taaaggaagg cgcacctctc cctttcgcgt acgacatcct caccccagtc | 180 |
| ttccaatacg gcaatcgcgc tttcaccaaa tacccacaag atattccaga ctattttaaa | 240 |
| caaacattcc ccgaaggcta ttcttgggaa cgctctatga cctatgaaga tcatggaatt | 300 |
| tgtatcgcta cctccgacat tactatgaa ggcgactgtt ttatttataa aattcgcttt | 360 |
| gatggaacta acttcccccc aaacggccct gtaatgcaaa agaagacctt aaaatgggaa | 420 |
| cctagcaccg aaaaaatgta tgtacgcgac ggagttctta agggtgacgt aaacatggca | 480 |
| cttctgctcg aaggaggtgg acactaccgc tgcgatttta aaccactta taaagccaaa | 540 |
| aaagatgttc gtcttccagg tgcacacaag gtggaccacc gcattgaaat cctgagccac | 600 |
| gataaagatt ataataaagt taaactctat gaacacgccg aagcccgcta ttctatgtta | 660 |
| ccgtctcagg ctaaagctag c | 681 |

<210> SEQ ID NO 4
<211> LENGTH: 681
<212> TYPE: DNA
<213> ORGANISM: Artificial
<220> FEATURE:
<223> OTHER INFORMATION: Synthetic DNA Encoding Engineered Fluorescent
      Protein

<400> SEQUENCE: 4

| | |
|---|---|
| atgtcagtaa ttaaaccgga atgaaaatt aaattgcgtt tggaaggtgc cgttaacggc | 60 |
| catgaatttg taattgaagg agaaggaaaa ggcaaaccat cgaaggaac ccagaccctg | 120 |
| gatttaaccg taaagaagg cgcacctctc cctttcgcgt acgacatcct caccccagcc | 180 |
| ttccaatacg gcaatcgcgc tttcaccaaa tacccaaaag atattccaga ctattttaaa | 240 |
| caaacattcc ccgaaggcta ttcttgggaa cgctctatga cctatgaaga tcaaggaatt | 300 |
| tgtatcgcta cctccgacat tactatgaa ggagactgtt ttttttataa gattcgcttt | 360 |
| gatggaacta acttcccccc gaacggccct gtaatgcaaa agaagacctt aaaatgggaa | 420 |
| cctagcaccg aaaaaatgta tgtacgcgac ggagttctta agggtgacgt aaacatggca | 480 |
| cttctgctcg aaggaggtgg acactaccgc tgcgatttta aaccactta taaagccaaa | 540 |
| aaagatgttc gtcttccaga tgcacacgag gtggaccacc gcattgaaat cctgagccac | 600 |
| gataaagatt ataataaagt taaactctat gaacacgccg aagcccgcta ttctatgtta | 660 |
| ccgtctcagg ctaaagctag c | 681 |

<210> SEQ ID NO 5
<211> LENGTH: 681
<212> TYPE: DNA
<213> ORGANISM: Artificial
<220> FEATURE:
<223> OTHER INFORMATION: Synthetic DNA Encoding Engineered Fluorescent
      Protein

<400> SEQUENCE: 5

| | |
|---|---|
| atgtcagtaa ttaaaccgga atgaaaatt aaattgcgta tggaaggtgc cgttaacggc | 60 |
| cataaatttg taattgaagg agaaggaata ggcaaaccat acgaaggaac ccagaccctg | 120 |
| gatttaaccg taaagaagg cgcacctctc cctttctcgt acgacatcct caccccagcc | 180 |

```
ttccaatacg gcaatcgcgc tttcaccaaa tacccaaaag atattccaga ctattttaaa    240
caagcattcc ccgaaggcta ttcttgggaa cgctctatga cctatgaaga tcaaggaatt    300
tgtatcgcta cctccgacat tactatggaa ggagactgtt ttttttataa gattcgcttt    360
gatggaacta acttcccccc gaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taaagccaaa    540
aaagatgttc gtcttccaga tgcacacgag gtggaccacc gcattgaaat cctgagccac    600
gataaagatt ataataaagt tagactctat gaacacgccg aagcccgcta ttctatgtta    660
ccgtctcagg ctaaagctag c                                              681
```

```
<210> SEQ ID NO 6
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 6
```

Met Ser Val Ile Lys Pro Glu Met Lys Ile Lys Leu Arg Met Glu Gly
1               5                   10                  15

Ala Val Asn Gly His Lys Phe Val Ile Glu Gly Glu Gly Lys Gly Asn
            20                  25                  30

Pro Phe Glu Gly Thr Gln Thr Leu Asp Leu Thr Val Lys Glu Gly Ala
        35                  40                  45

Pro Leu Pro Phe Ala Tyr Asp Ile Leu Thr Pro Val Phe Gln Tyr Gly
    50                  55                  60

Asn Arg Ala Phe Ala Lys Tyr Pro Gln Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp His Gly Ile Cys Ile Ala Thr Ser Asp Ile Thr Met Glu Gly Asp
            100                 105                 110

Cys Phe Ile Tyr Lys Ile Arg Phe Asp Gly Thr Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Ala His Lys Val Asp
            180                 185                 190

His Arg Ile Glu Ile Leu Ser His Asp Lys Asp Tyr Asn Lys Val Lys
        195                 200                 205

Leu Tyr Glu His Ala Glu Ala Arg Tyr Ser Met Leu Pro Ser Gln Ala
    210                 215                 220

Lys
225

```
<210> SEQ ID NO 7
<211> LENGTH: 225
<212> TYPE: PRT
<213> ORGANISM: Artificial
```

<220> FEATURE:
<223> OTHER INFORMATION: Synthetic Fluorescent Protein

<400> SEQUENCE: 7

Met Ser Val Ile Lys Pro Glu Met Lys Ile Lys Leu Arg Leu Glu Gly
1               5                   10                  15

Ala Val Asn Gly His Glu Phe Val Ile Glu Gly Glu Gly Lys Gly Lys
            20                  25                  30

Pro Phe Glu Gly Thr Gln Thr Leu Asp Leu Thr Val Lys Glu Gly Ala
        35                  40                  45

Pro Leu Pro Phe Ala Tyr Asp Ile Leu Thr Pro Ala Phe Gln Tyr Gly
    50                  55                  60

Asn Arg Ala Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
            100                 105                 110

Cys Phe Phe Tyr Lys Ile Arg Phe Asp Gly Thr Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Ala His Lys Val Asp
            180                 185                 190

His Arg Ile Glu Ile Leu Ser His Asp Lys Asp Tyr Asn Lys Val Lys
        195                 200                 205

Leu Tyr Glu His Ala Gly Ala Arg Tyr Ser Met Leu Pro Ser Gln Ala
    210                 215                 220

Lys
225

<210> SEQ ID NO 8
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 8

Met Ser Val Ile Lys Pro Glu Met Lys Ile Lys Leu Arg Met Glu Gly
1               5                   10                  15

Ala Val Asn Gly His Lys Phe Val Ile Glu Gly Glu Gly Lys Gly Asn
            20                  25                  30

Pro Phe Glu Gly Thr Gln Thr Leu Asp Leu Thr Val Lys Glu Gly Ala
        35                  40                  45

Pro Leu Pro Phe Ala Tyr Asp Ile Leu Thr Pro Val Phe Gln Tyr Gly
    50                  55                  60

Asn Arg Ala Phe Thr Lys Tyr Pro Gln Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp His Gly Ile Cys Ile Ala Thr Ser Asp Ile Thr Met Glu Gly Asp

```
            100                 105                 110
Cys Phe Ile Tyr Lys Ile Arg Phe Asp Gly Thr Asn Phe Pro Pro Asn
        115                 120                 125
Gly Pro Val Met Gln Lys Lys Thr Leu Lys Trp Glu Pro Ser Thr Glu
    130                 135                 140
Lys Met Tyr Val Arg Asp Gly Val Leu Lys Gly Asp Val Asn Met Ala
145                 150                 155                 160
Leu Leu Leu Glu Gly Gly Gly His Tyr Arg Cys Asp Phe Lys Thr Thr
                165                 170                 175
Tyr Lys Ala Lys Lys Asp Val Arg Leu Pro Gly Ala His Lys Val Asp
            180                 185                 190
His Arg Ile Glu Ile Leu Ser His Asp Lys Asp Tyr Asn Lys Val Lys
        195                 200                 205
Leu Tyr Glu His Ala Glu Ala Arg Tyr Ser Met Leu Pro Ser Gln Ala
    210                 215                 220
Lys
225

<210> SEQ ID NO 9
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 9

Met Ser Val Ile Lys Pro Glu Met Lys Ile Lys Leu Arg Leu Glu Gly
1               5                   10                  15
Ala Val Asn Gly His Glu Phe Val Ile Glu Gly Glu Gly Lys Gly Lys
            20                  25                  30
Pro Phe Glu Gly Thr Gln Thr Leu Asp Leu Thr Val Lys Glu Gly Ala
        35                  40                  45
Pro Leu Pro Phe Ala Tyr Asp Ile Leu Thr Pro Ala Phe Gln Tyr Gly
    50                  55                  60
Asn Arg Ala Phe Thr Lys Tyr Pro Lys Asp Ile Pro Asp Tyr Phe Lys
65                  70                  75                  80
Gln Thr Phe Pro Glu Gly Tyr Ser Trp Glu Arg Ser Met Thr Tyr Glu
                85                  90                  95
Asp Gln Gly Ile Cys Ile Ala Thr Ser Asp Ile Thr Met Glu Gly Asp
            100                 105                 110
Cys Phe Phe Tyr Lys Ile Arg Phe Asp Gly Thr Asn Phe Pro Pro Asn
        115                 120                 125
Gly Pro Val Met Gln Lys Lys Thr Leu Lys Trp Glu Pro Ser Thr Glu
    130                 135                 140
Lys Met Tyr Val Arg Asp Gly Val Leu Lys Gly Asp Val Asn Met Ala
145                 150                 155                 160
Leu Leu Leu Glu Gly Gly Gly His Tyr Arg Cys Asp Phe Lys Thr Thr
                165                 170                 175
Tyr Lys Ala Lys Lys Asp Val Arg Leu Pro Asp Ala His Glu Val Asp
            180                 185                 190
His Arg Ile Glu Ile Leu Ser His Asp Lys Asp Tyr Asn Lys Val Lys
        195                 200                 205
Leu Tyr Glu His Ala Glu Ala Arg Tyr Ser Met Leu Pro Ser Gln Ala
    210                 215                 220
Lys
```

<210> SEQ ID NO 10
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 10

```
Met Ser Val Ile Lys Pro Glu Met Lys Ile Lys Leu Arg Met Glu Gly
1               5                   10                  15

Ala Val Asn Gly His Lys Phe Val Ile Glu Gly Glu Gly Ile Gly Lys
            20                  25                  30

Pro Tyr Glu Gly Thr Gln Thr Leu Asp Leu Thr Val Lys Glu Gly Ala
        35                  40                  45

Pro Leu Pro Phe Ser Tyr Asp Ile Leu Thr Pro Ala Phe Gln Tyr Gly
    50                  55                  60

Asn Arg Ala Phe Thr Lys Tyr Pro Lys Asp Ile Pro Asp Tyr Phe Lys
65                  70                  75                  80

Gln Ala Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
            100                 105                 110

Cys Phe Phe Tyr Lys Ile Arg Phe Asp Gly Thr Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Ala His Glu Val Asp
            180                 185                 190

His Arg Ile Glu Ile Leu Ser His Asp Lys Asp Tyr Asn Lys Val Arg
        195                 200                 205

Leu Tyr Glu His Ala Glu Ala Arg Tyr Ser Met Leu Pro Ser Gln Ala
    210                 215                 220

Lys
225
```

<210> SEQ ID NO 11
<211> LENGTH: 43
<212> TYPE: DNA
<213> ORGANISM: Artificial
<220> FEATURE:
<223> OTHER INFORMATION: Synthetic Amplification Primer

<400> SEQUENCE: 11
cttgcaatcc gatcttgcag caggtgactt cgactcttgg ggt        43

<210> SEQ ID NO 12
<211> LENGTH: 65
<212> TYPE: DNA
<213> ORGANISM: Artificial
<220> FEATURE:
<223> OTHER INFORMATION: Synthetic Amplification Primer

<400> SEQUENCE: 12

```
cttgcaatcc gatcttgcag caggtgactt cgactcttgg ggtaacggcc ataaatttgt      60
aattg                                                                 65

<210> SEQ ID NO 13
<211> LENGTH: 43
<212> TYPE: DNA
<213> ORGANISM: Artificial
<220> FEATURE:
<223> OTHER INFORMATION: Synthetic Amplification Primer

<400> SEQUENCE: 13
cacctgctgc aagatcggat tgcaagtaga agctacgagc act                       43

<210> SEQ ID NO 14
<211> LENGTH: 62
<212> TYPE: DNA
<213> ORGANISM: Artificial
<220> FEATURE:
<223> OTHER INFORMATION: Synthetic Amplification Primer

<400> SEQUENCE: 14
cacctgctgc aagatcggat tgcaagtaga agctacgagc actaacggca ccttccatac     60
gc                                                                    62

<210> SEQ ID NO 15
<211> LENGTH: 43
<212> TYPE: DNA
<213> ORGANISM: Artificial
<220> FEATURE:
<223> OTHER INFORMATION: Synthetic Amplification Primer

<400> SEQUENCE: 15
cctccaaagt gacttagctg ccggcgattt tgatagctgg ggc                       43

<210> SEQ ID NO 16
<211> LENGTH: 63
<212> TYPE: DNA
<213> ORGANISM: Artificial
<220> FEATURE:
<223> OTHER INFORMATION: Synthetic Amplification Primer

<400> SEQUENCE: 16
cctccaaagt gacttagctg ccggcgattt tgatagctgg ggcgatcaag gaatttgtat     60
cgc                                                                   63

<210> SEQ ID NO 17
<211> LENGTH: 43
<212> TYPE: DNA
<213> ORGANISM: Artificial
<220> FEATURE:
<223> OTHER INFORMATION: Synthetic Amplification Primer

<400> SEQUENCE: 17
cgccggcagc taagtcactt tggaggtaaa atgagcgggc cga                       43

<210> SEQ ID NO 18
<211> LENGTH: 64
<212> TYPE: DNA
<213> ORGANISM: Artificial
<220> FEATURE:
<223> OTHER INFORMATION: Synthetic Amplification Primer

<400> SEQUENCE: 18
cgccggcagc taagtcactt tggaggtaaa atgagcgggc cgattcatag gtcatagagc     60
```

```
gttc                                                            64

<210> SEQ ID NO 19
<211> LENGTH: 43
<212> TYPE: DNA
<213> ORGANISM: Artificial
<220> FEATURE:
<223> OTHER INFORMATION: Synthetic Amplification Primer

<400> SEQUENCE: 19
tttacagtct gacttggcgg ctggggattt cgattcgtgg ggg                  43

<210> SEQ ID NO 20
<211> LENGTH: 63
<212> TYPE: DNA
<213> ORGANISM: Artificial
<220> FEATURE:
<223> OTHER INFORMATION: Synthetic Amplification Primer

<400> SEQUENCE: 20
tttacagtct gacttggcgg ctggggattt cgattcgtgg ggggaggtg gacactaccg  60 ctg                                                             63

<210> SEQ ID NO 21
<211> LENGTH: 43
<212> TYPE: DNA
<213> ORGANISM: Artificial
<220> FEATURE:
<223> OTHER INFORMATION: Synthetic Amplification Primer

<400> SEQUENCE: 21
ccccagccgc caagtcagac tgtaaataga aagaccgcgc aga                  43

<210> SEQ ID NO 22
<211> LENGTH: 62
<212> TYPE: DNA
<213> ORGANISM: Artificial
<220> FEATURE:
<223> OTHER INFORMATION: Synthetic Amplification Primer

<400> SEQUENCE: 22
ccccagccgc caagtcagac tgtaaataga aagaccgcgc agattcgagc agaagtgcca  60
tg                                                              62

<210> SEQ ID NO 23
<211> LENGTH: 41
<212> TYPE: DNA
<213> ORGANISM: Artificial
<220> FEATURE:
<223> OTHER INFORMATION: Synthetic Amplification Primer

<400> SEQUENCE: 23
tttgccgcta gctttagcct gagacggtaa catagaatag c                    41

<210> SEQ ID NO 24
<211> LENGTH: 35
<212> TYPE: DNA
<213> ORGANISM: Artificial
<220> FEATURE:
<223> OTHER INFORMATION: Synthetic Amplification Primer

<400> SEQUENCE: 24
tacatatggg cgcgcatgcc tcagtaatta aaccg                           35
```

<210> SEQ ID NO 25
<211> LENGTH: 8
<212> TYPE: PRT
<213> ORGANISM: Artificial
<220> FEATURE:
<223> OTHER INFORMATION: Synthetic Peptide

<400> SEQUENCE: 25

Asp Tyr Lys Asp Asp Asp Asp Lys
1               5

<210> SEQ ID NO 26
<211> LENGTH: 20
<212> TYPE: PRT
<213> ORGANISM: Artificial
<220> FEATURE:
<223> OTHER INFORMATION: Synthetic Peptide

<400> SEQUENCE: 26

Ser Ala Arg Ser Phe Tyr Leu Gln Ser Asp Leu Ala Ala Gly Asp Phe
1               5                   10                  15

Asp Ser Trp Gly
            20

<210> SEQ ID NO 27
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 27

Met Ser Val Ile Lys Pro Asp Met Lys Ile Lys Leu Arg Met Glu Gly
1               5                   10                  15

Ala Val Asn Gly His Lys Phe Val Ile Glu Gly Glu Gly Lys Gly Lys
                20                  25                  30

Pro Phe Glu Gly Thr Gln Thr Met Asp Leu Thr Val Lys Glu Gly Ala
            35                  40                  45

Pro Leu Pro Phe Ala Tyr Asp Ile Leu Thr Thr Val Phe Gln Tyr Gly
        50                  55                  60

Asn Arg Ala Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
            100                 105                 110

Cys Phe Phe Tyr Lys Asp Gly Thr Asn Phe Pro Pro Asn Gly Pro Val
        115                 120                 125

Met Gln Lys Lys Thr Leu Lys Trp Glu Pro Ser Thr Glu Lys Met Tyr
    130                 135                 140

Val Arg Asp Gly Val Leu Lys Gly Asp Val Asn Met Ala Leu Leu Leu
145                 150                 155                 160

Glu Gly Gly Gly His Tyr Arg Cys Asp Phe Lys Thr Thr Tyr Lys Ala
                165                 170                 175

Lys Lys Asp Val Arg Leu Pro Asp Ala His Lys Val Asp His Arg Ile
            180                 185                 190

Glu Ile Leu Ser His Asp Lys Asp Tyr Asn Lys Val Lys Leu Tyr Glu
        195                 200                 205

His Ala Glu Ala Arg Tyr Ser Met Leu Pro Ser Gln Ala Lys Ile Arg

```
              210                 215                 220
Phe
225

<210> SEQ ID NO 28
<211> LENGTH: 8
<212> TYPE: PRT
<213> ORGANISM: Artificial Sequence
<220> FEATURE:
<223> OTHER INFORMATION: Epitope tag

<400> SEQUENCE: 28

Asp Tyr Lys Asp Asp Asp Asp Lys
1               5
```

METHOD OF GENERATING PLOYNUCLEOTIDES ENCODING ENHANCED FOLDING VARIANTS

RELATED APPLICATIONS

This application is a continuation-in-part of co-owned U.S. patent application Ser. No. 11/900,551, filed Sep. 11, 2007 now abandoned, which is a divisional of Ser. No. 10/423,688 filed Apr. 24, 2003, now issued as U.S. Pat. No. 7,271,241, which is a continuation-in-part of Ser. No. 10/132,067 filed Apr. 24, 2002 now abandoned.

STATEMENT AS TO RIGHTS TO INVENTIONS MADE UNDER FEDERALLY SPONSORED RESEARCH OR DEVELOPMENT

This invention was made with government support under Contract No. DE-AC52-06 NA 25396 awarded by the U.S. Department of Energy. The government has certain rights in the invention.

BACKGROUND OF THE INVENTION

Protein insolubility constitutes a significant problem in basic and applied bioscience, in many situations limiting the rate of progress in these areas. Protein folding and solubility has been the subject of considerable theoretical and empirical research. However, there still exists no general method for improving intrinsic protein folding and solubility. Such a method would greatly facilitate protein structure-function studies, drug design, de novo peptide and protein design and associated structure-function studies, industrial process optimization using bioreactors and microorganisms, and many disciplines in which a process or application depends on the ability to tailor or improve the solubility of proteins, screen or modify the solubility of large numbers of unique proteins about which little or no structure-function information is available, or adapt the solubility of proteins to new environments when the structure and function of the protein(s) are poorly understood or unknown.

Overexpression of cloned genes using an expression host, for example E. coli, is the principal method of obtaining proteins for most applications. Unfortunately, many such cloned foreign proteins are poorly folded, insoluble and/or unstable when overexpressed. There are two sets of approaches currently in use which deal with such proteins. One set of approaches modifies the environment of the protein in vivo and/or in vitro. For example, proteins may be expressed as fusions with more soluble proteins, or directed to specific cellular locations. Chaperons may be coexpressed to assist folding pathways. Insoluble proteins may be purified from inclusion bodies using denaturants and the protein subsequently refolded in the absence of the denaturant. Modified growth media and/or growth conditions can sometimes improve the folding and solubility of a foreign protein. However, these methods are frequently cumbersome, unreliable, ineffective, or lack generality. A second set of approaches changes the sequence of the expressed protein. Rational approaches employ site-directed mutation of key residues to improve protein stability and solubility. Alternatively, a smaller, more soluble fragment of the protein may be expressed. These approaches require a priori knowledge about the structure of the protein, knowledge which is generally unavailable when the protein is insoluble. Furthermore, rational design approaches are best applied when the problem involves only a small number of amino-acid changes. Finally, even when the structure is known, the changes required to improve solubility may be unclear. Thus, many thousands of possible combinations of mutations may have to be investigated leading to what is essentially an "irrational" or random mutagenesis approach. Such an approach requires a method for rapidly determining the solubility of each version.

Random or "irrational" mutagenesis redesign of protein solubility carries the possibility that the native function of the protein may be destroyed or modified by the inadvertent mutation of residues which are important for function, but not necessarily related to solubility. However, protein solubility is strongly influenced by interaction with the environment through surface amino acid residues, while catalytic activities and/or small substrate recognition often involve partially buried or cleft residues distant from the surface residues. Thus, in many situations, rational mutation of proteins has demonstrated that the solubility of a protein can be modified without destroying the native function of the protein. Modification of the function of a protein without effecting its solubility has also been frequently observed. Furthermore, spontaneous mutants of proteins bearing only 1 or 2 point mutations have been serendipitously isolated which have converted a previously insoluble protein into a soluble one. This suggests that the solubility of a protein can be optimized with a low level of mutation and that protein function can be maintained independently of enhancements or modifications to solubility. Furthermore, a screen for function may be applied concomitantly after each round of solubility selection during the directed evolution process.

In the absence of a screen for function, for example when the function is unknown, the final version of the protein can be backcrossed against the wild type in vitro to remove nonessential mutations. This approach has been successfully applied by Stemmer in "Rapid Evolution Of A Protein In Vitro By DNA Shuffling," by W. P. C. Stemmer, Nature 370, 389 (1994), and in "DNA Shuffling By Random Fragmentation And Reassembly: In Vitro Recombination For Molecular Evolution," by W. P. C. Stemmer, Proc. Natl. Acad. Sci. USA 91, 10747 (1994) to problems in which the function of a protein had been optimized and it was desired to remove nonessential mutations accumulated during directed evolution. The development of highly specialized protein variants by directed, in vitro evolution, which exerts unidirectional selection pressure on organisms, is further discussed in: "Searching Sequence Space: Using Recombination To Search More Efficiently And Thoroughly Instead Of Making Bigger Combinatorial Libraries," by Willem P. C. Stemmer, Biotechnology 13, 549 (1995); in "Directed Evolution: Creating Biocatalysts For The Future," by Frances H. Arnold, Chemical Engineering Science 51, 5091 (1996); in "Directed Evolution Of A Fucosidase From A Galactosidase By DNA Shuffling And Screening," by Ji-Hu Zhang et al., Proc. Natl. Acad. Sci. USA 94, 4504 (1997); in "Functional And Nonfunctional Mutations Distinguished By Random Combination Of Homologous Genes," by Huimin Zhao and Frances H. Arnold, Proc. Natl. Acad. Sci. USA 94, 7007 (1997); and in "Strategies For The In Vitro Evolution of Protein Function: Enzyme Evolution By Random Recombination of Improved Sequences", by Jeff Moore et al., J. Mol. Biol. 272, 336-346 (1997). Therein, efficient strategies for engineering new proteins by multiple generations of random mutagenesis and recombination coupled with screening for improved variants is described.

In order to use directed evolution to improve the folding of a protein of interest, it can be fused to a folding reporter. When poorly folding proteins are fused to such folding reporters, they adversely affect the function of the reporter proteins to which they are fused, by trapping them in aggregated or unfolded non-functional states. When the folding reporter has an easily identifiable phenotype, such as antibiotic resistance[1-6], fluorescence[7] or color complementation[8] it is relatively straightforward to identify or select bacteria expressing protein fragments which are soluble and well folded following directed evolution, by using the phenotype of the fused folding reporter. This approach has been applied to the selection of mutated versions of naturally insoluble or poorly expressed proteins[4,7,9].

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India). GFP-like proteins are an expanding family of homologous, 25-30 kDa polypeptides sharing a conserved 11 beta-strand "barrel" structure. The GFP-like protein family currently comprises well over 100 members, cloned from various Anthozoa and Hydrozoa species, and includes red, yellow and green fluorescent proteins and a variety of non-fluorescent chromoproteins. A wide variety of fluorescent protein labeling assays and kits are commercially available, encompassing a broad spectrum of GFP spectral variants and GFP-like fluorescent proteins, including DsRed and other red fluorescent proteins (Clontech, Palo Alto, Calif.; Amersham, Piscataway, N.J.).

Wild type green fluorescent protein (GFP) cloned from *Aequorea victoria*, normally misfolds and is poorly fluorescent when overexpressed in the heterologous host *E. coli*. It is found predominantly in the inclusion body fraction of cell lysates. The misfolding is incompletely understood, but is thought to result from the increased expression level or rate in *E. coli*, or the inadequacy of the bacterial chaperone and related folding machinery under conditions of overexpression. The folding yield also decreases dramatically at higher temperatures (37° C. vs. 27° C.). This wild type GFP is a very poor folder, as it is extremely sensitive to the expression environment.

DNA shuffling has been used to obtain a GFP mutant having a whole cell fluorescence 45-times greater than the standard, commercially available plasmid GFP. See, e.g., "Improved Green Fluorescent Protein By Molecular Evolution Using DNA Shuffling," by Andreas Crameri et al., Nature Biotechnology 14, 315 (1996). The screening process optimizes the function of GFP (green fluorescence), and thus uses a functional screen. The screening process coincidentally optimizes the solubility of the GFP, in that the GFP is only fluorescent when properly folded, this being the basis for the use of GFP as a folding reporter.

It has been demonstrated that improving the apparent functionality of a protein can sometimes increase the concomitant solubility of the protein, as in: "Redesigning enzyme topology by directed evolution," by G. Macbeath, P. Kast, and D Hilvert, Science 279, 1958-1961 (1998); "Expression of an antibody fragment at high levels in the bacterial cytoplasm," by P. Martineau, P. Jones, and G. Winter, J. Mol. Biol. 280, 117-127 (1998); "Antibody scFv fragments without disulfide bonds made by molecular evolution," K. Proba, A. Worn, A. Honegger, and A. Pluckthun, J. Mol. Biol. 275, 245-253 (1998); and "Functional Expression of Horseradish Peroxidase in *E. coli* by Directed Evolution," Lin Zhanglin, Todd Thorsen, and Frances H. Arnold, Biotechnol. Prog. 15, 467-471 (1999). In each case, the driving force for the directed evolution was the functionality of the protein of interest. For example, if the protein was an enzyme, the assay for improved function was the turnover of a chromogenic analog of the enzyme's natural substrate; if the protein was an antibody, it was the recognition of the target antigen by the antibody.

For cytoplasmic expression of antibodies, the recognition was linked to cell survival, (binding of the antibody to a selectable protein marker which was an antigen for the antibody of interest providing selection for functional antibodies); in the case of phage displayed antibodies without disulfide bonds, the recognition was transduced to successful binding of the displayed phage to the target antigen of the displayed antibody in a biopanning protocol. An apparent increase in the amount of protein expressed in the soluble fraction relative to the unselected target proteins was noted upon expression of the proteins in *E. coli*. The apparent increase in activity of desirable mutants during the evolution was due at least in part to an increase in the number of correctly folded (and hence functional) protein molecules, and not exclusively to an increase in the specific activity of a given protein molecule. However, the driving force for the selection or screening process during the directed evolution depended on the functionality (and functional assay for) the protein of interest.

Many proteins have no easily detectable functional assay, and thus identification of proteins with improved folding yield by an increase in apparent activity due to a larger number of correctly folded molecules, is not a general method for improving folding by directed evolution. Furthermore, even when functional assays are available, apparent increases in activity can also be due to increases in the specific activity (activity of an individual protein molecule) even when the total number of correctly folded molecules remains the same. Thus, increases in apparent activity do not necessarily translate to increases in the solubility of proteins. Furthermore, functional assays are protein-specific, and thus must be developed on a case-by-case basis for each new protein. Functional assays therefore lack the generality needed to identify proteins which are soluble, or to find genetic variants (mutants and fragments) of proteins with improved solubility, in a high-throughput manner for proteomics or functional genomics wherein large numbers of different proteins about which little or no functional/structural information is known, are to be solubly expressed.

A number of different methods have been developed to create thermostable proteins, most of which involve the creation of libraries and the identification of improved proteins by selection or screening. Conceptually, the most straightforward way to identify proteins with improved thermostability has been to apply a thermal challenge to a collection of individual clones and test the remaining functionality of the clones, repeating this process if necessary, to combine useful mutations[10, 11]. A similar method, which does not rely on such extensive screening requirements, involves direct selection of clones growing at elevated temperature within thermophilic bacteria. However, to date, this method has only been applied to the selection of thermophilic antibiotic resistance proteins[13,14], and as laboratory organisms typically do not grow at elevated temperatures, it has been difficult to generalize. As a result, considerable effort has been put into the development of alternative approaches which involve selection or screening for biophysical or biological properties which can serve as surrogates for, and are often correlated with, thermostability.

One of the first examples of this approach is the PRO-SIDE (protein stability increased by directed evolution)[15-22] approach in which resistance to protease digestion is used as the surrogate property for protein stability, with filamentous phage infectivity being the selection modality. Proteins under test are expressed between two domains in g3p (the phage receptor for bacteria): if they are cleaved by protease, the filamentous phage loses the N terminal g3p domain and consequently its ability to infect; if the protein is protease resistant infectivity is maintained. This has been successfully used to increase the stability of the beta1 domain of protein G[17], the cold shock protein of *B. subtilis*[19] and ribonuclease T1[15]. In another approach involving directed evolution, Shusta et al., showed that the display levels of heterologous proteins on the surface of yeast correlated with expression levels and thermal stability[23], although exceptions to this have been recently described[24].

Consensus engineering[25,26] is an approach to increase protein stability which does not use directed evolution, but the informational content of aligned sequences. By modifying a sequence so that it more closely resembles a consensus derived from the alignment of numerous proteins of a particular family, it has been found that significant increases in stability can be obtained. This has been applied to antibodies and antibody fragments[26-34], GroEL minichaperones[35-36], p53[37], WW[38] and SH3 domains[39]. More recently consensus engineering has been applied to the creation of novel proteins, rather than the stepwise modification of pre-existing ones to resemble a consensus. Perhaps the most striking success was the application to phytases[40-42], in which a final protein with a Tm of 90.4° C. was obtained: 52° C. greater than the best component parental sequence[43]. Similar stability was obtained with a consensus ankyrin sequence based on the alignment of 2000 different ankyrins[44-46]. We recently applied this method to the creation of a consensus green protein (CGP)[47]. Although we obtained a functional fluorescent protein, its Tm was 5° C. less than the monomeric Azami Green[48] used to identify the sequences comprising the consensus. However, in this case no effort was made to examine the effects of individual mutations, and it is likely that some of the consensus mutations were destabilizing, as had been previously shown for the phytase[40-43].

Other methods used to increase protein stability, relying heavily on structural information, include "helix capping"[49-52] or optimization[53-55], the introduction of salt bridges or their replacement by hydrophobic interactions[56-62], the introduction of clusters of aromatic-aromatic interactions[63-65] and rigidification strategies, in which disulfide bonds or glycine to alanine, or Xaa to proline changes are introduced[66-68]. However, most of these have been carried out on model structures, and none has been widely adopted.

Thermostabilization of proteins is regarded as important in a number of biotechnological and pharmaceutical applications. Within the context of industrial enzymes, thermostability leads to longer enzyme survival times, as well as more efficient reactions at higher temperatures and diminished microbial contamination, all of which result in diminished costs. In the pharmaceutical arena, thermostability of protein therapeutics leads to longer half lives and more effective drugs[69-71]. Thermostability has also been regarded as important in the use of proteins as scaffolds to generate libraries of specific binders. It has been reasoned that if a starting scaffold is more stable, it will be more tolerant to the destabilizing effects of mutations, or insertions, used to mediate binding. This has been shown for affinity reagents based on ankyrins[72], and has also been applied to the creation of phage antibody libraries[30]. Finally, proteins of increased thermostability are more resistant to mutations than the protein from which they are derived, promoting evolvability by providing greater permissivity to mutations leading to novel functions[73,74].

SUMMARY OF THE INVENTION

The invention provides directed evolution methods for improving the folding, solubility and stability (including thermostability) characteristics of polypeptides. In one aspect, the invention provides a method for generating folding and stability-enhanced variants of proteins, including but not limited to fluorescent proteins, chromophoric proteins and enzymes. In another aspect, the invention provides methods for generating thermostable variants of a target protein or polypeptide via an internal destabilization baiting strategy. Internally destabilization a protein of interest is achieved by inserting a heterologous, folding-destabilizing sequence (folding interference domain) within DNA encoding the protein of interest, evolving the protein sequences adjacent to the heterologous insertion to overcome the destabilization (using any number of mutagenesis methods), thereby creating a library of variants. The variants in the library are expressed, and those with enhanced folding characteristics selected. Following the initial round(s) of evolution to overcome the destabilizing influence of the heterologous insert, additional destabilizing heterologous inserts may placed into the protein at other locations, followed by further evolution to overcome the resulting destabilization. This may be continued, in a recursive fashion, until the desired degree of stability is achieved, whereupon the heterologous inserts are removed to produce the selected variant protein.

More particularly, in one embodiment, the invention provides a directed-evolution method of generating a polynucleotide encoding an enhanced folding variant of a target polypeptide, which comprises: (a) linking a polynucleotide encoding the target polypeptide to a polynucleotide encoding a folding interference domain, wherein the folding interference domain is inserted into a permissive site of the target polypeptide; (b) mutating the polynucleotide encoding the target polypeptide to generate a library of mutated fusion protein constructs; (c) expressing the fusion proteins of the library; and, (d) selecting a polynucleotide encoding a fusion protein with enhanced folding activity compared to a fusion protein encoded by the linked polypeptides of step (a). Optionally, the process is repeated, in order to conduct one or more rounds of directed evolution (steps "b" through "d" on the polynucleotide selected in the previous round. In a related embodiment, the method is repeated by introducing yet another destabilizing heterologous insert into a different location within the protein, whilst maintaining the initial heterologous insert, and further evolving to generate variants capable of regaining the additional destabilizing insert. Thus, the method may further comprise conducting one or more subsequent rounds of the directed evolution process of steps (a) through (e) on a polynucleotide selected in step (d), wherein a further folding interference domain is inserted into a permissive site other than the one used in the preceding round of the directed evolution process. This process may be continued in a recursive manner, through two, three, or more rounds, in order to achieve the maximal (or otherwise desired) stability enhancement. In some embodiments, the polypeptide variant displays increased thermostability compared with the target protein.

Once the evolution has been completed, and one or more polynucleotides encoding enhanced folding variants selected, the inserted folding interference domain(s) is/are removed from the polynucleotide, in order to permit the generation of the variant protein. This may be accomplished by expressing the polynucleotide after the folding interference domains have been removed. Therefore, also provided are the polypeptide variants encoded by such resulting polynucleotides, including without limitation, enhanced folding variants of fluorescent proteins (see Example 1, infra), related proteins such as chromophoric proteins, enzymes and the like.

Folding interference domains are inserted into a "permissive site" within the target protein (or variants selected from an initial round of evolution). A permissive site may be, without limitation, a site exposed on the polypeptide surface, a beta turn in the polypeptide, or a hydrophilic region of the polypeptide. However, in practice, any site may be used as hereinafter defined.

Folding activity, and enhancement thereof, is determined by any number of means well known in the art, including without limitation, measuring folding kinetics, thermostability, resistance to chemical denaturation, biological activity and tolerance to heterologous inserts.

As described further and in the Examples, the method of the invention was applied to a fluorescent protein, and successfully generated highly thermostable variants, one of which can be heated to 99° C. for short periods of time without denaturing, and retains 85% of its fluorescence when heated to 80° C. for fourteen hours (see Examples, infra).

BRIEF DESCRIPTION OF THE DRAWINGS

FIG. 1. Schematic outline of the internal destabilization methodology used to generate thermostable variants of CGP (see Example 1). FIG. 1B shows induced bacterial colonies, with a colony expressing CGP before (1) and after insertion of the HCDR3 in loop 1 (colony 2) or loop 2 (colony 3). The remaining colonies are mutated variants, showing fluorescent improvements.

FIG. 3. Sequence alignments of various thermostable fluorescent protein variants generated according to the methods of the invention, compared to the reference protein, CGP, and to the protein from which CGP was initially derived, mAG (BAD52002). Shown are sequences of CGP [SEQ ID NO: 27], eCGP1 [SEQ ID NO: 6], eCGP13 [SEQ ID NO: 8], eCGP2 [SEQ ID NO: 7], eCGP23 [SEQ ID NO: 9], eCGP123 [SEQ ID NO: 10].

FIG. 7. PCR assembly shown diagrammatically (see Example 1). For each of the libraries in which a single folding interference domain was inserted, the full length protein was assembled using two fragments as shown in the figure under error prone PCR conditions in which mutations accumulated in the CGP gene, but not the inserted domain. The mutations are indicated as small lightening bolts. For libraries in which two folding interference domains were inserted, the full length protein was assembled using three fragments as shown in the figure. The template was a collection of mutated CGP genes obtained after mutation and selection of CGP containing a single insert. For libraries in which three folding interference domains were inserted, the full length protein was assembled using four fragments as shown. The template was a collection of mutated CGP genes obtained after mutation and selection of CGP containing two inserts. Those mutations that are beneficial tend to accumulate.

SEQUENCES

Figure 1A:
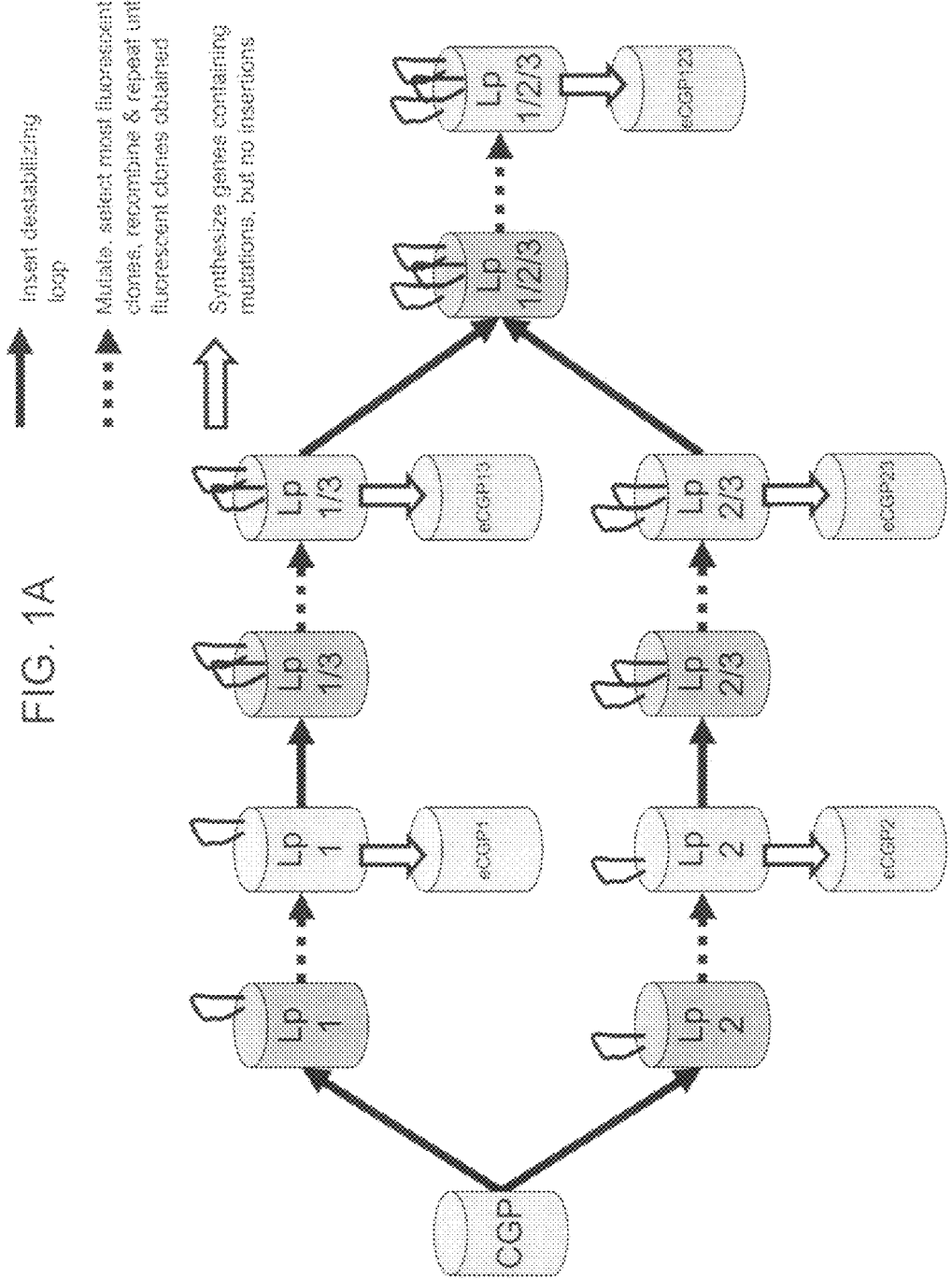
FIG. 1A shows the strategy applied. After the insertion of a single insert at two different sites, CGP loses fluorescence that can be regained by mutation and selection. This process is repeated until a fluorescent protein resistant to the destabilizing effects of three loops is obtained. For each evolved fluorescent variant, a gene is synthesized which lacks the inserted loop(s).
Figure 2:
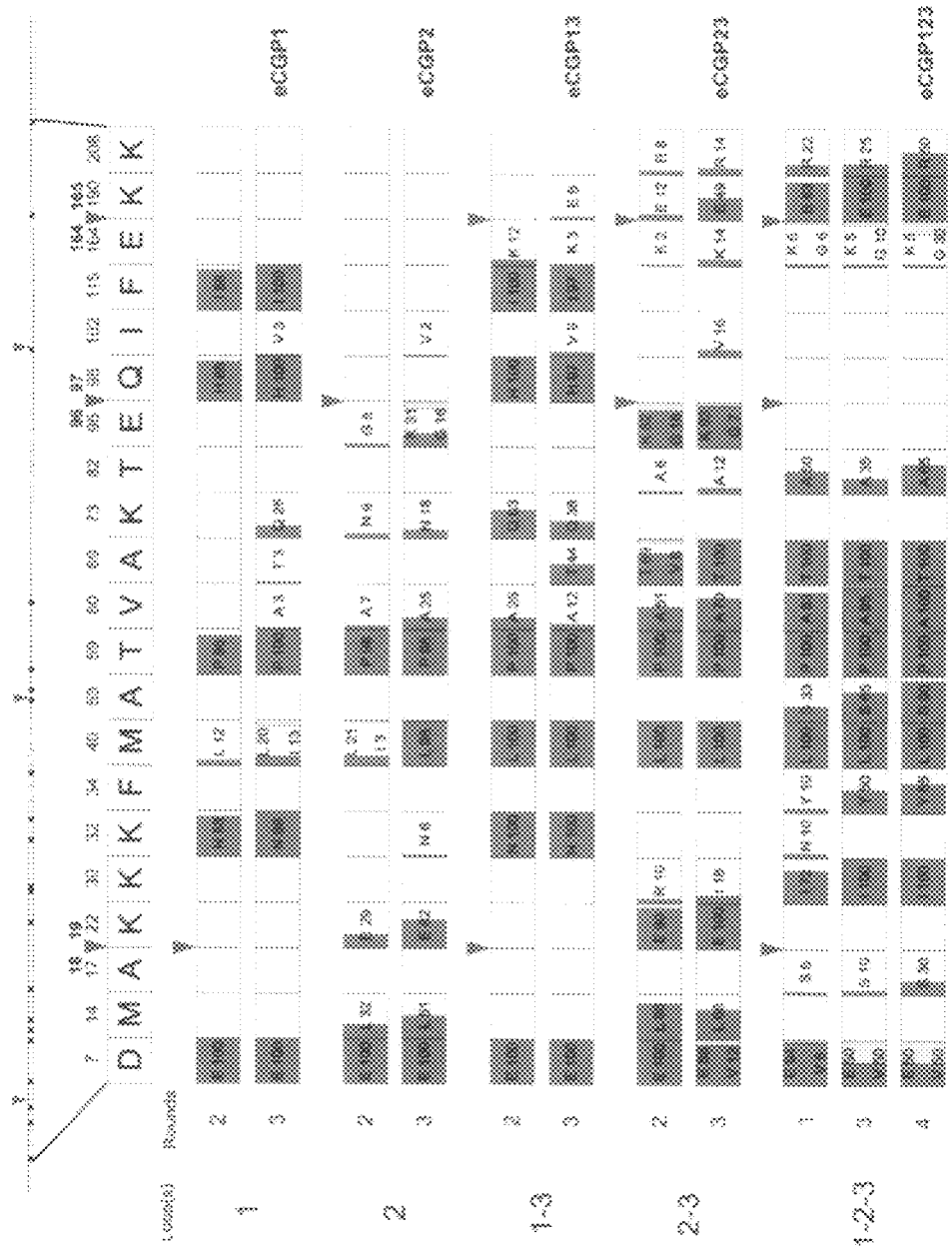
FIG. 2. Accumulation of amino acid mutations through iterative internal destabilization. The original sequence of CGP is represented by the small squares at the top, with the positions of amino acids that underwent mutation indicated as black boxes. The exact positions and wild type sequences of these are shown below, with the three insertion sites indicated as inverted red triangles flanked by the exact positions. The mutations occurring at each site, for each evolutionary round and loop insertion strategy, are shown. White squares indicate wild type sequence. Where a mutation has occurred, the letter indicates the new mutation, and the number the percentage of the sequenced fluorescent clones that contain that mutation. This is also represented graphically by that portion of the white square colored green. For example, at position 7, in all early evolutionary rounds 100% of clones changed the wild type aspartate to a glutamate. If more than one mutation is found at a particular site, both amino acids are given with their percentages, indicated by green and yellow boxes. After three rounds when loops 2 and 3 were targeted, 12% of clones also showed a valine at this position, which increased to 50% in later rounds. The percentage of clones carrying a particular mutation are shown if that mutation comprises more than 5% of clones in any of the evolutionary rounds.

The Sequence Listing is submitted as an ASCII text file named "87389-01_ST25.txt," created on Jun. 16, 2011, 21.3 KB, which is incorporated by reference herein.

DETAILED DESCRIPTION OF THE INVENTION

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is a protein that has intrinsic fluorescence. Typically, a fluorescent protein has a structure that includes an 11-stranded beta-barrel.

A "chromophoric protein" or "chromoprotein" are used interchangeably and refer to a class of proteins, recently identified from various corals, anemones and often sea organisms, which have intrinsic color and, in some cases, variable degrees of intrinsic or inducible fluorescence. Their color is usually due to absorption, rather than fluorescence. Typically, a chromo-protein has a structure similar to the fluorescent proteins, i.e., an 11-stranded beta-barrel.

The "MMDB Id: 5742 structure" as used herein refers to the GFP structure disclosed by Ormo & Remington, MMDB Id: 5742, in the Molecular Modeling Database (MMDB), PDB Id: 1EMA PDB Authors: M. Ormo & S. J. Remington PDB Deposition: 1 Aug. 96 PDB Class: Fluorescent Protein PDB Title: Green Fluorescent Protein From *Aequorea Victoria*. The Protein Data Bank (PDB) reference is Id PDB Id: 1 EMA PDB Authors: M. Ormo & S. J. Remington PDB Deposition: 1 Aug. 96 PDB Class: Fluorescent Protein PDB Title: Green Fluorescent Protein From *Aequorea Victoria*. (see, e.g., Ormo et al. "Crystal structure of the *Aequorea victoria* green fluorescent protein." *Science* 1996 Sep. 6; 273(5280):1392-5; Yang et al, "The molecular structure of green fluorescent protein." *Nat Biotechnol.* 1996 October; 14(10):1246-51).

"Root mean square deviation" ("RMSD") refers to the root mean square superposition residual in Angstroms. This number is calculated after optimal superposition of two structures, as the square root of the mean square distances between equivalent C-alpha-atoms.

A "folding interference domain" as used herein refers to a domain that interferes with the folding of a polypeptide ("Xid"). The presence of a folding interference domain in a fusion protein of a polypeptide of interest should detectably interfere with folding, as measured by any criteria capable of discriminating between better and poorer folded versions of the polypeptide of interest, P, within the context of a fusion with Xid. In the practice of the method of the invention, the folding interference domain need not be misfolded itself. In fact, it may be folded, not folded, soluble or it might be insoluble. In one aspect of the invention, the interference domain, Xid, is inserted within the protein at a "permissive site", to form the structure $P_1$-Xid-$P_2$, where $P_1$ and $P_2$ are two (contiguous) portions of the same protein. Further details regarding the detection and assessment of folding is set forth infra.

A "complementarity determining region" (CDR) is a portion of an antibody that contacts the antigen. In general antibodies have three complementarity regions in the heavy chain and three in the light chain. The CDRs are the most variable portions of an antibody, and have also been termed hypervariable regions. In both heavy and light chains, the third complementarity determining regions are the most variable in both sequence and length.

"Domain" refers to a unit of a protein or protein complex, comprising a polypeptide subsequence, a complete polypeptide sequence, or a plurality of polypeptide sequences.

A "permissive site" is any region within the protein or polypeptide into which a folding interference domain may be inserted with the effect of reducing the activity or folding of the protein or polypeptide, but without completely destroying the activity or folding of the protein or polypeptide. Thus, for example, when applying the method to a fluorescent protein, a folding interference domain inserted into a permissive site should reduce fluorescence but not eliminate this activity altogether. In general, a permissive site may be anywhere within the protein of interest, and may be within an exposed surface and/or hydrophilic region, such as for example a loop domain (i.e., beta turn).

"Physical linkage", "link" and "join" refer to any method known in the art for functionally connecting two or more molecules or domains (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

A "fusion protein" refers to a chimeric molecule formed by the joining of two or more polypeptides through a bond formed one polypeptide and another polypeptide. Fusion proteins may also contain a linker polypeptide in between the constituent polypeptides of the fusion protein. The term "fusion construct" or "fusion protein construct" is generally meant to refer to a polynucleotide encoding a fusion protein.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

A "reporter molecule" has a detectable phenotype. Often, the reporter molecule is a polypeptide, such as an enzyme, or a fluorescent polypeptide. A reporter polypeptide may have intrinsic activity. In the context of the methods of the invention, a reporter molecule has a detectable phenotype associated with correct folding or solubility of the reporter molecule. For example, the reporter could be an enzyme or a fluorescent polypeptide. For an enzyme, the detectable phenotype would then be the ability to turn over a substrate giving a detectable product or change in substrate concentration or physical state. For a fluorescent protein, the activity would be the emission of fluorescence upon excitation by the appropriate wavelength(s) of light.

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A e protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Such conservatively modified variants are in addition to and do not exclude polymorphic variants, interspecies homologs, and alleles of the invention.

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 98% or 99% similar over a specified region or, when not specified, over the entire sequence), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100, 200, 300, 400, 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

Directed Evolution Method of Improving Folding, Solubility and Stability

To improve the folding of a polypeptide, a nucleic acid molecule encoding the polypeptide is joined to a folding interference domain coding sequence, which when expressed, causes the polypeptide to fold poorly. DNA encoding the polypeptide is mutagenized and a library of variants expressed. Sequence alterations that overcome the poor folding imposed by the folding interference domain can be identified by an increase in the activity of the polypeptide or a reporter linked to the polypeptide. Such sequence mutations can include modification of coding sequence, deletion of coding sequence, insertion of additional coding sequences, change of order of coding sequences, within the existing coding sequence or at the N or C termini (5' or 3' end of the encoding nucleic acid), non-native amino acids.

It is often desirable to improve folding of a protein that does not have a detectable activity. For such an application, a detectable moiety can be linked to the target polypeptide/folding interference domain fusion protein to provide a means of assaying for enhanced folding. Thus, the method of selecting robustly-folding proteins has wide applicability.

Where the target protein P has an easily measured phenotype, its folding (or solubility) success can be monitored in the presence of a bait protein domain, herein termed a "folding interference domain" (Xid), as Xid-L-P, for example. These bait domains may also be inserted internally into permissive sites of P, e.g., for GFP at any of the loop positions (as in, for example, $P_1$-Xid-$P_2$ and $P_1$-Xid$_a$-$P_2$-Xid$_b$-$P_3$; wherein $P_1$, $P_2$ and $P_3$ Xid$_a$ and Xid$_b$ may be the same Xid or different Xids). New variants of target protein P, better suited for folding and/or solubility under stringent conditions can thereby be produced. See further discussion of the internal destabilization methodology, under the subheading "Thermostable/Highly Stable Protein Variants Using Internal Destabilization", below.

When P has no easily measured phenotype associated with correct folding, a reporter domain can be used, for example, in a construct such as Xid-L1-P-L2-R, where R is the reporter domain that tells about the folding of P, Xid is the folding interference domain, and L1 and L2 are flexible linkers.

As will be appreciated by one of skill in the art, this method can also be applied in a block-optimization of a new protein scaffolding, P, comprised of a series of smaller domains, or subdomains of P ($P_1$, $P_2$, etc.). In this embodiment, for example, a construct such as Xid-L-$P_1$-R is used to optimize $P_1$ using R as the reporter. Next, a subdomain, $P_2$, can be added, e.g., in a construct such as Xid-L-$P_2$-$P_1$-R and used to optimize $P_2$ using R as the reporter. Optionally, $P_1$ can be optimized for folding at the same time. The same reporter domain need not be used to optimize each $P_N$. Eventually, after $P_N$ is added, the entire P domain is built from the smaller subdomains.

Thus, the methods of the invention can be used to increase folding and solubility of a target polypeptide as well as subdomains contained within the target polypeptide.

Thermostable/Highly Stable Protein Variants Using Internal Destabilization:

The methods of the invention may be used to generate better folding, highly stable protein variants, including thermostable variants. Internal destabilization of a protein via the insertion of one or more folding interference domains within the protein structure may be used to provide the destabilizing stimulus for evolving a more stable protein. In this aspect of the invention, a folding interference domain is inserted into a permissive site of the target protein structure, and evolution is applied in order to overcome its destabilizing effect. In a related embodiment, a recursive evolution strategy is employed, whereby additional folding interference domains are introduced into the protein, one at a time (while maintaining previously introduced insert(s)), and evolution is conducted to overcome the destabilizing impact. Such a recursive evolution process was employed in the generation of the highly stable fluorescent protein variants as described in Example 1, infra, in which three destabilizing inserts were introduced in three rounds of destabilization and evolution. To further illustrate, this would involve the initial creation of P1-Xid-P2 in a first round, with the optional creation of $P_1$-Xid-$P_2$-Xid-$P_3$ in a subsequent round following evolution of $P_1$-Xid-$P_2$ to functionality. Such insertion can be continued for three or more insertions. Furthermore, as described above, when the protein P has no detectable phenotype, a construct of the kind $P_1$-Xid-$P_2$-R, where R is a reporter, can also be employed.

More particularly, in the practice of the internal destabilization method of the invention, the destabilization is mediated by the sequential introduction of destabilizing heterologous inserts (folding interference domains) into the protein of interest, with the use of gene synthesis (or other methods) to "remove" such inserts after the evolution process is complete. Single destabilizing internal inserts are grafted into permissive sites within a protein in such a way that upon each insertion, folding and function are significantly affected but not destroyed (FIG. 1A). Upon overcoming the effect of a single insert by the initial round of evolution, the procedure is repeated with additional destabilizing inserts in an iterative fashion. The method enables one to overcome a final destabilizing force that would completely destroy both folding and function if applied in a single step. Although conceptually similar to the transplantation of global suppressor mutations to wild type proteins, the level of thermostability that can be attained is greater, and also tunable: the more destabilizing folding interference domains inserted, and overcome, the greater the stability/thermostability of the eventual protein produced.

Thus, in one embodiment, the invention provides a directed evolution method of generating a polynucleotide encoding an enhanced folding variant of a target polypeptide, comprising the steps of: (a) linking a polynucleotide encoding the target polypeptide to a polynucleotide encoding a folding interference domain, wherein the folding interference domain is inserted into a permissive site of the target polypeptide; (b) mutating the polynucleotide encoding the target polypeptide to generate a library of mutated fusion protein constructs; (c) expressing the fusion proteins of the library; and, (d) selecting a polynucleotide encoding a fusion protein with enhanced folding activity compared to a fusion protein encoded by the linked polypeptides of step (a).

Optionally, the process above is repeated, in order to conduct one or more rounds of directed evolution (steps "b" through "d" on the polynucleotide selected in the previous round. In a related embodiment, the method is repeated by introducing yet another destabilizing heterologous insert into a different location within the protein, whilst maintaining the initial heterologous insert, and further evolving to generate variants capable of regaining the additional destabilizing insert. Thus, the method may further comprise conducting one or more subsequent rounds of the directed evolution process of steps (a) through (e) on a polynucleotide selected in step (d), wherein a further folding interference domain is inserted into a permissive site other than the one used in the preceding round of the directed evolution process. This process may be continued in a recursive manner, through two, three, or more rounds, in order to achieve the maximal (or otherwise desired) stability enhancement. In some embodiments, the polypeptide variant displays increased thermostability compared with the target protein.

Once the evolution has been completed, and one or more polynucleotides encoding enhanced folding variants selected, the inserted folding interference domain(s) is/are removed from the polynucleotide, in order to permit the generation of the variant protein. This may be accomplished by expressing the polynucleotide after the folding interference domains have been removed.

"Superfolding", highly stable fluorescent proteins have been generated using the methods set forth herein. In a particular embodiment, a number of fluorescent protein variants derived from an artificial fluorescent protein were generated (see Example 1, infra. Briefly, an iterative internal destabilization strategy was employed, resulting in the generation of fluorescent protein variants with superior folding and stability characteristics, as judged across multiple parameters, including thermal stability. In the case of one such variant, eCGP123, thermal stability was increased to such an extent that the protein could be incubated overnight at 80° C. without being denatured. This protein could also be heated at 99° C. without completely losing fluorescence (see Example 1 infra).

In a further embodiment, a set of enhanced folding variants are produced according to the methods, supra, and examined at the coding and amino acid structural level in order to rationally "recombine" certain mutations which occur in a number of different variants. For example, in the approach to generating thermostable variants of a fluorescent protein as described in Example 1, a set of variant protein sequences (generated after two or three rounds of internal destabilization and evolution) were aligned and compared in order to generate a synthetic gene encoding a variant protein having the benefit of amino acid mutations that occurred in 20% or more of all of the variants in the set. In addition, this synthetic gene also included any silent (DNA level) mutations that occurred in greater than 90% of the coding sequences of the variants in the set. Finally, in order to concentrate on mutations responsible for global increases in stability, rather than mutations responding to specific changes in secondary structure adjacent to the insert site, mutations found within two amino acids of any insertion point were not included in the synthetic gene. The resulting polynucleotide sequence encodes a highly thermostable variant of the fluorescent protein (see Example 1).

The application of the methods of the invention to any other fluorescent or chromophoric protein is facilitated by the ease with which screening for correct folding can be carried out. This method is also likely to be generally applicable to any protein, providing three criteria are fulfilled: 1) Surface exposed insert sites are correctly identified; 2) An appropriate destabilizing insert is used; and 3) A method to select correctly folded clones is available. In the example used here, the structure of Dronpa[75] was used to identify the surface exposed loops. When structures or models are unavailable, secondary or tertiary structural prediction methods may provide sufficient information to identify suitable surface turns, since it is unlikely that inserts placed within protein cores could be overcome by mutation. The insert used here, based on an antibody HCDR3, was able to provide destabilization without completely inhibiting folding. However, other inserts are likely to be equally effective, and such inserts could even comprise whole proteins in which the N and C termini were close to one another. Perhaps most crucial for this method to work is the need for a method to select or screen for correctly folded clones. This is straightforward for fluorescent proteins, or ones for which calorimetric or fluorescent reagents are available. However, for the majority of proteins that have no directly screenable phenotype, alternative methods, such as folding reporters[7], will have to be used. These rely on observations applicants[1,74] and others[2] have made regarding the ability of poorly folding proteins to adversely affect the function of "reporter proteins" to which they are fused. When the folding reporter has an easily identifiable phenotype, such as antibiotic resistance[1,2], fluorescence[7] or color complementation[8] bacteria expressing well folded proteins can be easily identified. By fusing proteins containing destabilizing inserts to folding reporters, it should be possible to undertake direct phenotypic selection of colonies with correctly folded target proteins[76]. These alternative approaches provide a possible means to apply insertional destabilization and evolution to any protein that can be fused to a folding reporter. Such constructs would correspond to the $P_1$-Xid-$P_2$-R variety described above.

As described in Example 1, the destabilizing insert used to generate highly stable fluorescent proteins was based on an antibody heavy chain complementarity determining region 3 (HCDR3). This insert was chosen as the N and C termini of HCDR3s are close to one another within the context of an anti-parallel beta strand[77], thereby presumptively providing destabilization without completely inhibiting folding. It is likely that alternative inserts could also provide appropriate degrees of destabilization, and it is possible that a panel of destabilizing inserts could be developed. In fact, such inserts could even comprise whole proteins in which the N and C termini were close to one another.

In example 1 below, a family of proteins was evolved from the starting fluorescent protein CGP. These were named eCGP1, eCGP2, eCGP13, eCGP23 and eCGP123, and corresponded to the proteins evolved after insertion of a single Xid (eCGP1 and eCGP2), two Xid's (eCGP13, eCGP23) or three Xid's (eCGP123). The Xid in this case is a modified HCDR3.

Figure 5A:
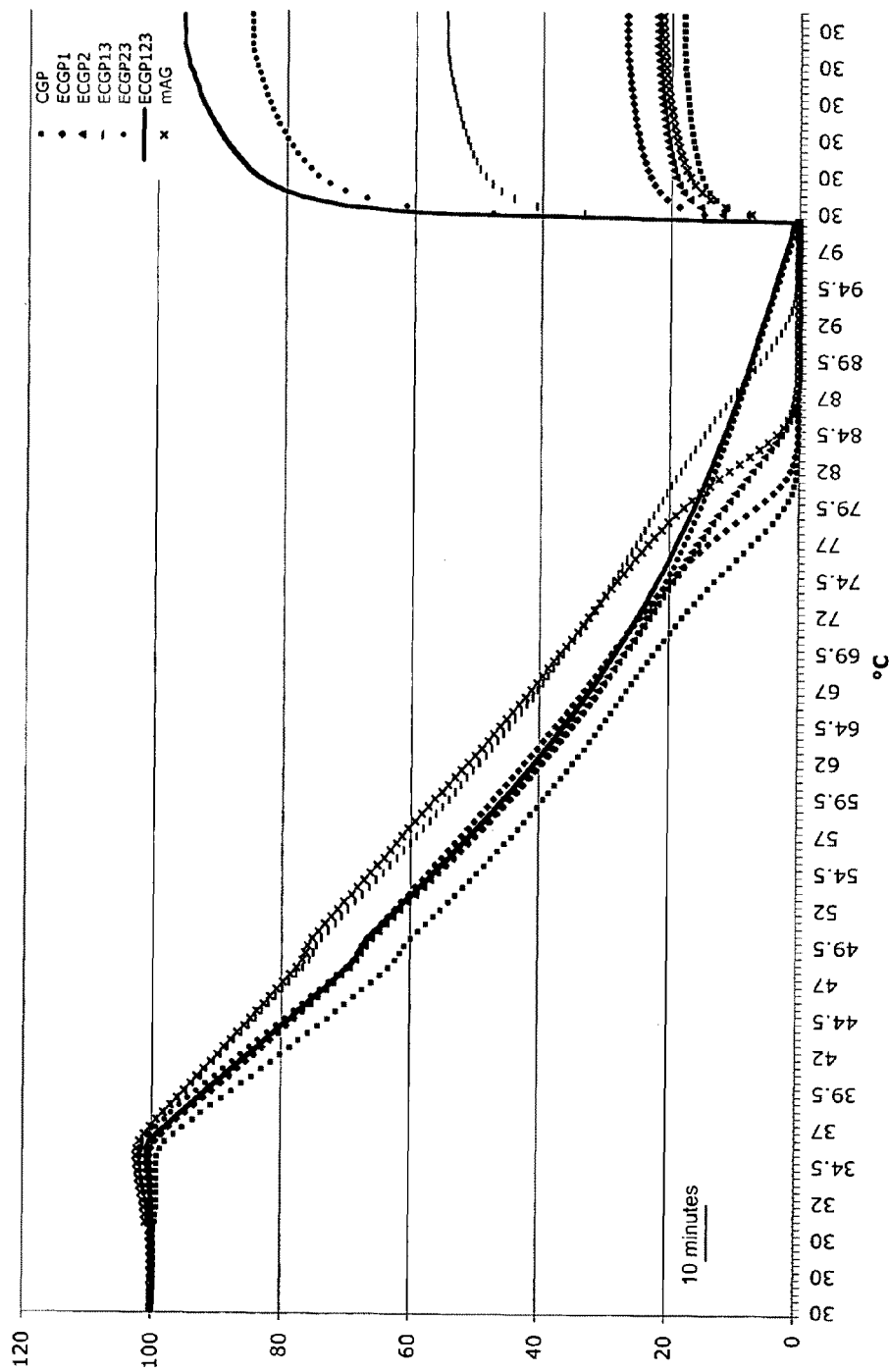
FIG. 5. Thermal stability of evolved fluorescent proteins. (A) Fluorescence profile of the different proteins gradually heated to 99° C. and then allowed to recover at 30° C. Fluorescence was measured every six seconds, and normalized to the fluorescence level at 30° C. (B) Enlargement of fluorescence profile from 90-99° C., showing the persistence of low levels of fluorescence with eCGP123 and eCGP23 at 99° C. (C) Stability with repeated heating and cooling cycles. Proteins were heated to 99° C. for one minute and then cooled to 30° C. for two minutes. This was carried out sixty times and fluorescence was measured at the end of each heating or cooling period. (D) The survival of fluorescent proteins at 80° C. was assessed by heating to 80° C., measuring fluorescence every six seconds. Fluorescence was normalized to the fluorescence level after five minutes at 80° C., at which time the initial rapid loss of fluorescence due to heating stabilized. (E) The survival of fluorescent proteins at 80° C. was assessed by heating to 80° C., and measuring fluorescence each six seconds. Fluorescence was normalized to the fluorescence level after five minutes at 80° C.
(FIG. 5D). (F): As FIG. 5E, except proteins were heated to 85° C.
Figure 5D:
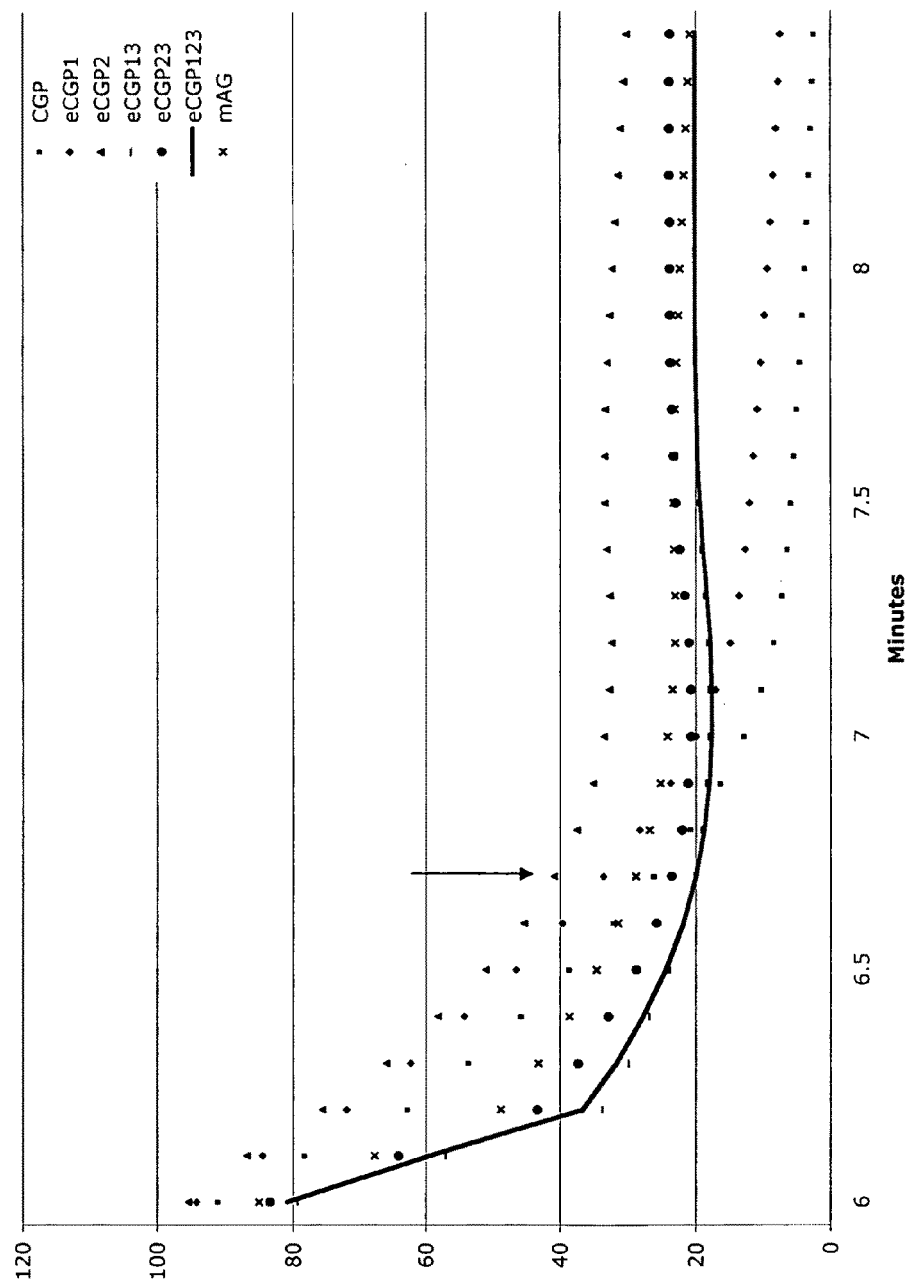
Figure 5E:
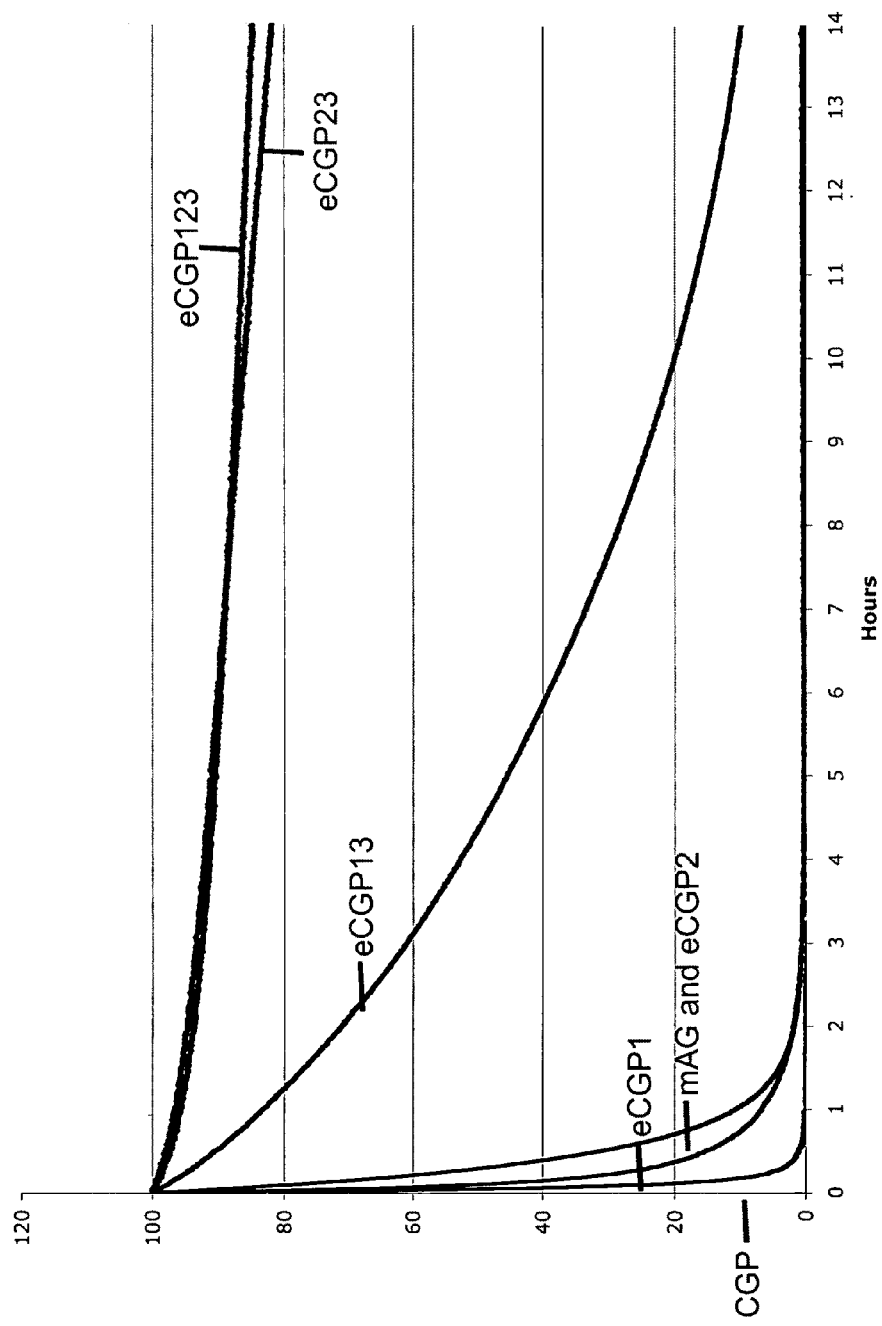
Figure 5F:
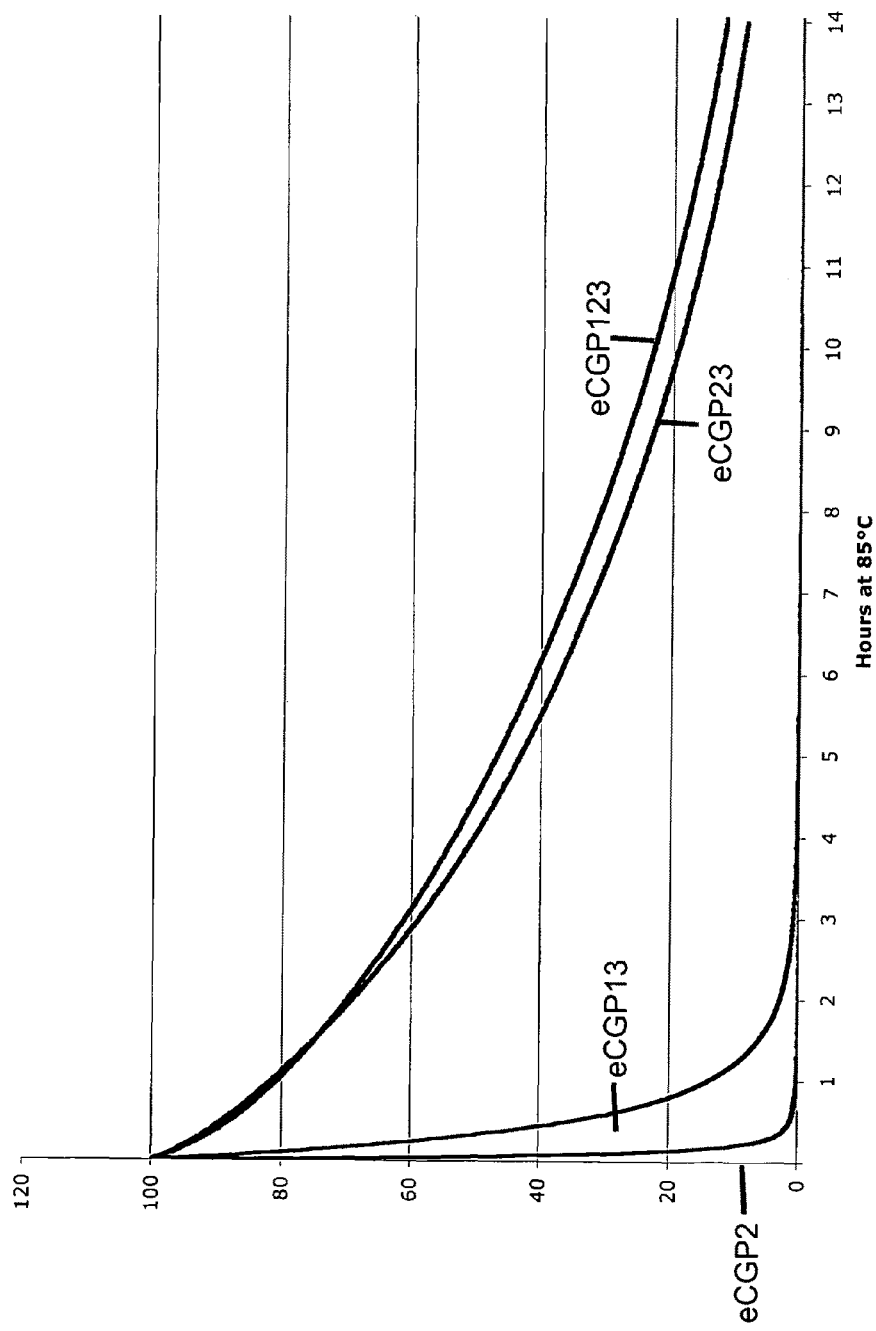

The fluorescence loss that occurs when fluorescent proteins are heated is caused by a combination of disruption of the local fluorophore environment caused by thermal vibrations and unfolding. Unfolding, in turn, can be either reversible or irreversible. In general, the loss of fluorescence caused by thermal vibrations is almost instantaneously reversible, that caused by reversible unfolding depends upon the kinetics of refolding, while irreversible unfolding does not recover. A number of lines of evidence indicate that most of the loss of fluorescence with heating eCGP123 to 99° C. is due to disruption of the local fluorophore environment, rather than unfolding of the protein. First, a thermal melt does not show the inflection point characteristic of the onset of cooperative unfolding, shown by the other proteins (FIGS. 5a and 5b); secondly, at 99° C., some residual fluorescence is clearly present for eCGP123 and eCGP23, while it is completely lost for the other proteins (FIGS. 5b and 5c); thirdly, upon cooling after the thermal melt, over 60% of the fluorescence returns immediately (FIG. 5a and TABLE II); and finally, when the protein is repeatedly cycled between 99 and 30° C. fluorescence recovery is essentially immediate, and complete, with each cycle (FIG. 5c), while refolding would be expected to take longer. However, although it appears that most of the protein remains folded after short periods at 99° C., it is clear that prolonged incubations at high temperatures below 99° C. can cause significant loss of fluorescence. After 14 hours at 80° C., only 15% of the fluorescence normalized after stabilization at 80° C. is lost (FIG. 5e), whereas at 85° C., only 15% of the fluorescence remains (FIG. 5f).

When the thermal stability of the different evolved eCGP proteins is compared, the increased stability with increased evolution is striking, with the order of stability being eCGP123>eCGP23>eCGP13>eCGP2>eCGP1>CGP: evolution around each additional loop, results in increased stability. However, the individual loops are not equal in their stabilizing effects, with evolution around loop 2, appearing to provide the greatest individual stabilizing effect (compare eCGP1 to eCGP2 and eCGP13 to eCGP23). In fact, eCGP23 and eCGP123 are extremely similar to one another in their stability.

Figure 6A:
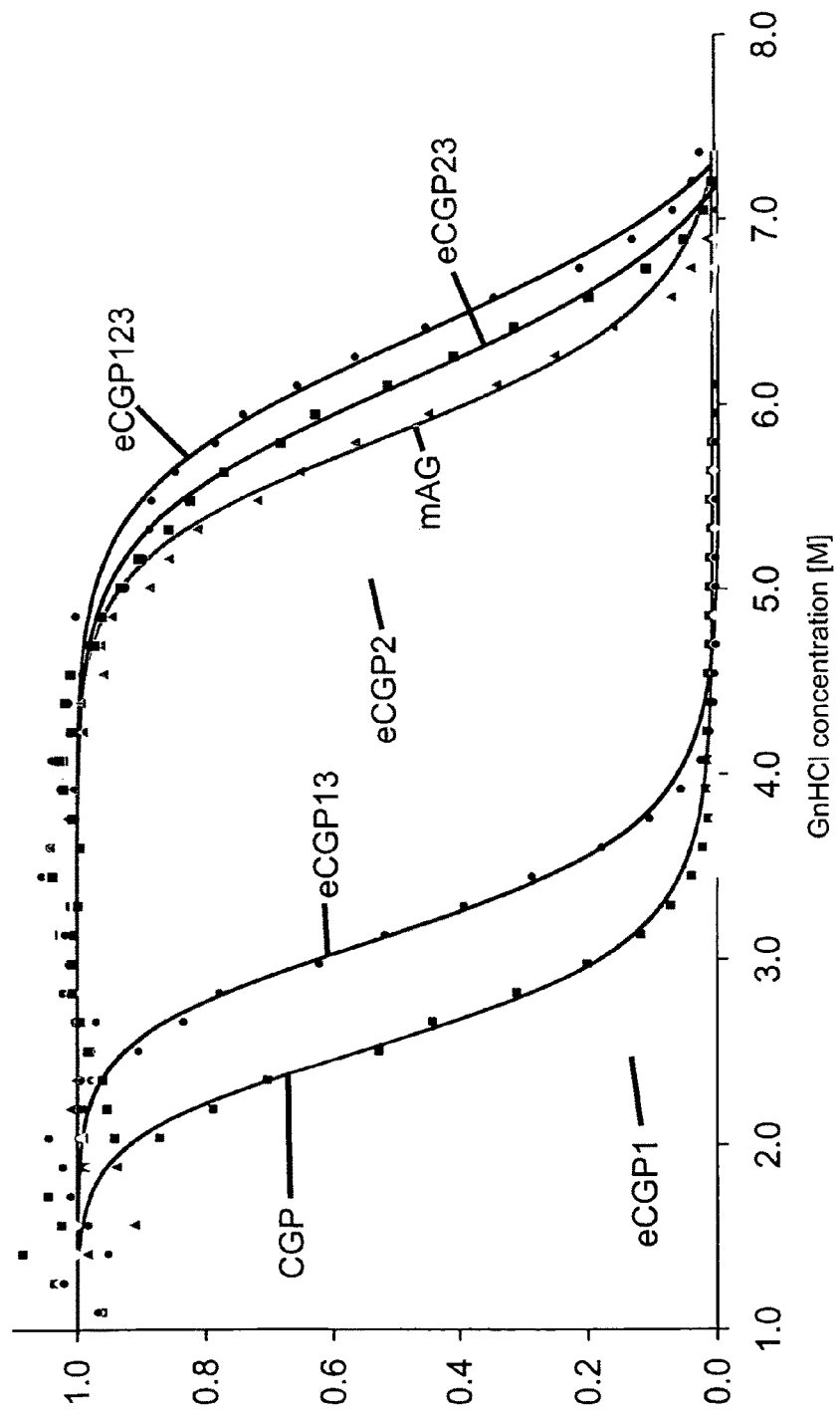
FIG. 6. Resistance to chemical denaturation. (A): Each of the evolved fluorescent proteins was diluted into 48 different Guanidium hydrochloride concentrations, with 7.4 M being the highest concentration. The residual fluorescence was measured at equilibrium, normalized and plotted. The recovered fluorescence was normalized by dividing the fluorescence of corresponding non-denatured samples diluted in parallel. (B): Dependence of the standard free energy of denaturation on guanidine concentration assuming a two-state folding model for the fluorescent proteins (TABLE III). (C): Refolding kinetics. Long-term (2000 s) progress curves for recovery of fluorescence during refolding of Gdn HCl-denatured eCGP123 (blue), CGP (magenta), and mAG (green) upon 20-fold dilution of denatured samples in fresh buffer containing 1 mM DTT at 25° C. (see Methods), with the inset showing the short-term progress curves. Initial rates $V_i$ were obtained from slope at t=0 s of $2^{nd}$-order polynomials fitted to the first 12 s of short-term progress curves. Fluorescence normalized by dividing by final fluorescence value at 15 h.

The eCGPs were also characterized by chemical denaturation using different concentrations of guanidine hydrochloride (FIG. 6a). See also, Example 1, infra.

General Nucleic Acid Methodology

The current invention employs basic nucleic acid methodology that is routine in the field of recombinant genetics. Basic texts disclosing the general methods of obtaining and manipulating nucleic acids in this invention include Sambrook and Russell, MOLECULAR CLONING, A LABORATORY MANUAL (3rd ed. 2001) and CURRENT PRO- TOCOLS IN MOLECULAR BIOLOGY (Ausubel et al., eds., John Wiley & Sons, Inc. 1994-1997, 2001 version)).

Often, the nucleic acid sequences encoding the fusion proteins of the invention are generated using amplification techniques. Examples of techniques sufficient to direct persons of skill through in vitro amplification methods are found in Berger, Sambrook, and Ausubel, as well as Dieffenfach & Dveksler, *PCR Primers: A Laboratory Manual* (1995): Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89:117.

Folding Interference Domains

Folding interference domains may be any protein, protein domain, or other polypeptide which causes the protein to fold improperly. In the practice of the internal destabilization method of the invention, such a peptide is inserted into a permissive site within the protein of interest. A permissive site is any region of the protein or polypeptide into which a destabilizing insert (or, folding interference domain) may be inserted with the effect of reducing the activity of the protein or polypeptide, but without completely destroying the activity of the protein or polypeptide. As will be appreciated, the choice of a folding interference domain may be somewhat dependent on the protein to which it is applied. Thus, for example, when applying the method to a fluorescent protein, a destabilizing insert should reduce fluorescence but not eliminate this activity altogether. Then, the directed evolution process may be used to recover as much of the activity lost as a result of the insert. In general, a permissive site may be anywhere within the protein of interest, and is usually within an exposed surface and/or hydrophilic region, such as for example a loop domain (i.e., beta turn). Any protein with an exposed loop in its structure is particularly amenable to the internal destabilization method of the invention.

In one embodiment, which may be generally applied to fluorescent or chromophoric proteins, a destabilizing insert domain based upon a heavy chain third antibody complementarity determining region (HCDR3) sequence is used, and inserted into one or more loops within the fluorescent or chromophoric protein structure (see Examples, infra). Although HCDR3 regions are highly diverse loops, they are embedded in a relatively conserved beta-sheet structure within an antibody in their native context. Based upon the results obtained form the studies described in the Examples, it is clear that the similarity between the context of the fluorescent protein loop regions into which the insert was made, and the context of the HCDR3s in an antibody molecule, resulted in favorable destabilization, whereby the insert was disruptive but not completely destructive to folding.

Folding interference domains may be inserted into a polynucleotide via well known molecular cloning methodologies. An example of a preferred methodology is PCR assembly (diagrammatically shown in FIG. 7).

The folding interference domain may be linked, either directly or via a linker, to either the N-terminus or C-terminus of the target polypeptide sequence. Alternatively, the domain may be inserted into an internal site of the target polypeptide that is permissive to the insertion. A permissive site of a host protein is one which tolerates the insertion of well-folded, soluble proteins or polypeptides (guest polypeptides) within the host protein scaffolding. Typical sites are turns and sterically open regions. One such example is amino acid residue 87 of *Escherichia coli* dihydrofolate reductase. If the protein has a measurable activity (enzyme, fluorescence, binding ability) associated with the native structure, a site is defined as permissive if the host protein containing the guest polypeptide retains at least 5%, or 10%, or preferably at least 20% of the host protein activity observed without the guest.

Target Polypeptides

A target protein or polypeptide can be any protein or polypeptide for which it is desirable to improve folding and stability. Often such polypeptides include those with reporter activity, such as a fluorescent protein, i.e., green or red fluorescent protein, or a chromophoric protein. Other proteins in relation to which the methods of the invention may be expected to result in the generation of enhanced folding variants include enzymes, including enzymes for which it would be desirable to increase thermostability.

A particular aspect of the invention relates to the generation of thermostable protein variants. There are a great number of proteins which could productively be modified to increase thermostability and thereafter be used in biotechnological, industrial and other processes demanding high temperatures, including without limitation polymerases, ligases, proteases, various enzymes used in starch processing (i.e., α-amylases, β-amylases, glucoamylases, α-glucosidases and others used in starch saccharification), enzymes useful in degradation of celluloses and in paper pulp processing (both of which require hot alkaline treatments), as well as various enzymes used in food processing (i.e., pectinolytic enzymes).

In the Examples which follow, dramatic thermostability was introduced into a consensus green protein (CGP)[47] fluorescent protein variant. Because of the close structural relationship among fluorescent and chromophoric proteins, the protocol used for generating thermostable variants of CGP may be easily applied to any other fluorescent or chromophoric protein with the aim of generating similarly increased thermostable variants (see subsection following).

Other proteins include various enzymes, e.g., antibiotic resistance proteins such as, chloramphenicol acetyltransferase, kanamycin resistance protein, beta-lactamase, tetracycline resistance protein, dihydrofolate reductase; and other enzymes such as subtilisin, fungal xylanases. Other target proteins include antibodies, for which increased binding to the target antigen can be used as the selection criterion.

Fluorescent and Chromophoric Proteins

A variety of fluorescent proteins and chromoproteins may be "evolved" according to the methods of the invention to generate variants having improved folding, solubility and/or stability. One group of such fluorescent proteins includes the Green Fluorescent Protein isolated from *Aequorea Victoria* (GFP), as well as a number of GFP variants, such as cyan fluorescent protein, blue fluorescent protein, yellow fluorescent protein, etc. A number of color shift mutants of GFP have been developed and may be employed in the directed evolution methods of the present invention. These colorshift GFP mutants have emission colors blue to yellow-green, increased brightness, and photostability (Tsien et al., 1998, Annual Review of Biochemistry 67: 509-544).

Additional GFP-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. Most recently, GFPs from the anthozoans *Renilla reniformis* and *Renilla kollikeri* were described (Ward et al., U.S. Patent Appn. 20030013849).

Another group of such fluorescent proteins includes the fluorescent proteins isolated from anthozoans, including without limitation the red fluorescent protein isolated from *Discosoma* species of coral, DsRed (Matz et al., 1999, Nat. Biotechnol. 17:969-973), (see, e.g., accession number AF168419 version AF168419.2). DsRed and the other anthozoan fluorescent proteins share only about 26-30% amino acid sequence identity to the wild-type GFP from *Aequorea Victoria*, yet all the crucial motifs are conserved, indicating the formation of the 11-stranded beta-barrel structure characteristic of GFP.

The crystal structure of DsRed has also been solved, and shows conservation of the 11-stranded beta-barrel structure of GFP MMDB Id: 5742 (Yarbrough et al., 2001, Proc. Natl. Acad. Sci. USA 98: 462-467).

A number of mutants of the longer wavelength red fluorescent protein DsRed have also been described, and similarly, may be evolved according to the invention. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989).

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with similar structures to GFP from corals, sea pens, sea squirts, and sea anemones have been described, and may be used to generate "superfolder" variants (for reviews, see Zimmer, 2002, Chem. Rev. 102: 759-781; Zhang et al., 2002, Nature Reviews 3: 906-918).

Fluorescent proteins from *Anemonia majano, Zoanthus* sp., *Discosoma striata, Discosoma* sp. and *Clavularia* sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

Additionally, another class of GFP-related proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3: 7; Lukyanov et al., 2000, supra).

Various other coral-derived chromoproteins closely related to the pocilloporins are also known (see, for example, Lukyanov et al. 2000, J. Biol. Chem. 275: 25879-82; Gurskaya et al., 2001, FEBS Letters 507:16-20).

Some fluorescent proteins are completely artificial and do not exist in nature, such as the consensus green protein (CGP) used as the starting material for example 1. This protein is based on the consensus sequence of 38 aligned proteins with homology to monomeric Azami green.

In one embodiment, fluorescent and chromophoric protein variants exhibiting enhanced folding, solubility, stability/thermostability are generated from any fluorescent or chromophoric protein having a structure with a root mean square deviation of less than 5 angstroms, often less than 3, or 4 angstroms, and preferably less than 2 angstroms from the 11-stranded beta-barrel structure of *Aequorea victoria* GFP MMDB Id: 5742. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID: 5742 structure is the conservation of the 11 beta strands, and the topology or connection order of the secondary structural elements (see, e.g., Ormo et al. "Crystal structure of the *Aequorea victoria* green fluorescent protein." Yang et al, 1996, *Science* 273: 5280, 1392-5; Yang et al., 1996 *Nat. Biotechnol.* 10:1246-51). Typically, most of the deviations between a fluorescent protein and the GFP structure are in the length(s) of the connecting strands or linkers between the crucial beta strands, see, e.g., the comparison of DsRed and GFP (Yarbrough et al., 2001, Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids although the sequence identity is only 23% comparing DsRed and GFP.

In comparing structure, the two structures to be compared are aligned using algorithms familiar to those with average skill in the art, using for example the CCP4 program suite. COLLABORATIVE COMPUTATIONAL PROJECT, NUMBER 4. 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Roger A. Sayle and E. J. Milner-White, "RasMol: Biomolecular graphics for all", Trends in Biochemical Science (TIBS), September 1995, Vol. 20, No. 9, p. 374.), or Swiss PDB Viewer, Guex, N and Peitsch, M. C. (1996) Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example DALI, Holm, L. & Sander, C. Protein-structure comparison by alignment of distance matrices. *Journal of Molecular Biology* 1993, 233, 123-138. The server site for the computer implementation of the algorithm is available, for example, at dali@ebi.ac.uk. The output of the DALI algorithm are blocks of sequence that can be superimposed between two structures using rigid body transformations. Regions with Z-scores at or above a threshold of Z=2 are reported as similar. For each such block, the overall RMSD is reported.

Generation of Fusion Proteins:

In some embodiments, an amino acid linker sequence is employed to separate polypeptide (and/or domain) components by a distance sufficient to ensure that each polypeptide could fold into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that can interact with functional epitopes on the first and second polypeptides; and (3) the lack of hydrophobic or charged residues that might react with the polypeptide functional epitopes. Typical peptide linker sequences contain Gly, Ser, Ala, Val and Thr residues. Often, a linker is a "flexible linker", that has a sequence such as $(Gly_4Ser)_x$, e.g., $(Gly_4Ser)_3$.

Amino acid sequences which may be usefully employed as linkers include those disclosed in Maratea et al. (1985) Gene 40:39-46; Murphy et al. (1986) *Proc. Natl. Acad. Sci. USA* 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other methods of joining the components of the chimeric protein include ionic binding by expressing negative and positive tails, and indirect binding through antibodies and streptavidin-biotin interactions. (See, e.g., *Bioconjugate Techniques*, supra). The components can also be joined together through an intermediate interacting sequence. The moieties included in the conjugate molecules can be joined in any order, although the most favorable configuration may be determined empirically.

Production of Proteins Using Recombinant Techniques

Well known recombinant methodology is used to generate the fusion proteins used in the practice of the method of the invention. Fusion constructs can be made by ligating the appropriate nucleic acid sequences encoding the desired amino acid sequences to each other by methods known in the art, in the proper reading frame, and expressing the product by methods known in the art. Nucleic acids encoding the domains to be incorporated into the fusion proteins of the invention can be obtained using routine techniques in the field of recombinant genetics (see, e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. New York, 1997).

Often, the nucleic acid sequences encoding the component domains to be incorporated into the fusion protein are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenbach & Dveksler, PCR Primers: A Laboratory Manual (1995)). Alternatively, overlapping oligonucleotides can be produced synthetically and joined to produce one or more of the domains. Nucleic acids encoding the component domains can also be isolated from expression libraries using antibodies as probes.

In an example of obtaining a nucleic acid encoding a domain to be included in the conjugate molecule using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89:117.

In some embodiments, it may be desirable to modify the polypeptides encoding the components of the conjugate molecules. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, the domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a disulfide linkage. The modification can be performed using either recombinant or chemical methods (see, e.g., Pierce Chemical Co. catalog, Rockford Ill.).

In some embodiments, the recombinant nucleic acids encoding the fusion proteins of the invention are modified to provide preferred codons which enhance translation of the nucleic acid in a selected organism (e.g., yeast preferred codons are substituted into a coding nucleic acid for expression in yeast).

Mutagenesis

Target polypeptides with enhanced folding ability are typically identified by mutating the nucleic acid sequence encoding the target polypeptide, generating a fusion protein (comprising the mutated target polypeptide, a poorly folding domain, and optionally, a reporter gene), and selecting those polypeptides with enhanced reporter activity, thus identifying target polypeptides that overcome the poor folding property imposed by the poorly folding domain.

The nucleic acid sequences encoding the target polypeptide of interest can be mutated using methods well known to those of ordinary skill in the art. The target polypeptide is usually mutated by mutating the nucleic acid. Techniques for mutagenizing are well known in the art. These include, but are not limited to, such techniques as error-prone PCR, chemical mutagenesis, DNA shuffling, and cassette mutagenesis. Alternatively, mutator strains of host cells may be employed to add mutational frequency (Greener and Callahan (1995) *Strategies in Mol. Biol.* 7: 32). For example, error-prone PCR (see, e.g., Ausubel, supra) uses low-fidelity polymerization conditions to introduce a low level of point mutations randomly over a long sequence. Other mutagenesis methods include, for example, recombination (WO98/42727); oligonucleotide-directed mutagenesis (see, e.g., the review in Smith, *Ann. Rev. Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al., Science 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

Folding Detection and Assessment

In the practice of the method of the invention, it is important to identify or develop a method to select or screen for correctly folded clones. When applied to fluorescent proteins, it is relatively straightforward to examine bacterial clones for fluorescence. A similar approach could be used for enzymes which can be expressed in bacteria, and for which calorimetric or fluorescent reagents are available. However, for the majority of proteins for which there is no obvious directly screenable phenotype, a separate screen for correct folding is required. This is not unlike the use of phage[78-80] or yeast display[81-84] to identify amino acids comprising specific binding sites: it is not sufficient to identify clones no longer binding to the binding partner, since loss of binding may be due to lack of folding. In addition to the negative selection for loss of binding, a positive selection for correct folding must also be included in the selection strategy. In the case of yeast, it is relatively straightforward, as only correctly folded proteins reach the cell surface and poorly folding proteins are retained in the endoplasmic reticulum. As a result it is sufficient to detect surface display using monoclona[82], polyclonal[81] or anti-tag[83] antibodies. In the case of phage display, recognition of conformational epitopes.

Typically, various phenotypic characteristics are used to provide surrogate indications of correct folding and enhancement thereof. In the practice of the methods of the invention, "folding activity", including "enhanced folding activity", may be detected and assessed using any number of surrogate tests commonly used to determine folding, including without limitation biological activity, spectroscopy, resistance to denaturation, kinetics, tolerance to high temperatures (thermostability), improved functionality of a fused folding reporter, and tolerance for additional random mutations and polypeptide insertions. In addition, circular dichroism may be used to distinguish between folded and unfolded forms of a polypeptide. Furthermore, folding kinetics may be used, wherein better folded versions of P are identified by their ability to adopt a correctly folded conformation faster than poorer folding variants or the wild type protein. Preferably, the evolved polypeptide will display about a 25% faster refolding time following denaturation.

In another embodiment, thermostability may be used to screen a library of protein variants for improved folding and stability. In this regard, any increase in the temperature at which the native protein may retain activity is significant, but the level of temperature increase may be adjusted according to the desired outcome. See, Examples, infra.

In another embodiment, resistance to denaturation (i.e., chemical denaturation) may be used to assess folding. For example, increasing concentrations of urea may be used to assess more robustly folding variants. A polypeptide variant with significantly improved folding activity is typically one which can tolerate about a 0.5 molar higher urea concentration compared to the wild type or starting polypeptide.

Tolerance to random mutations may also be used to assess the folding enhancement achieved following polypeptide evolution. Briefly, a library of random mutants of both the wild type (or pre-evolved) polypeptide and the test evolved polypeptide are generated. A 0.7% amino acid mutation rate, for example, may be appropriate. The library clones are then evaluated for fluorescence as a measure of correct folding. The presence and extent to which the evolved polypeptide mutant library displays a greater number of fluorescent clones relative to the wild type mutant library indicates the folding robustness of the evolved test polypeptide.

Similarly, tolerance to terminally fused or inserted polypeptides may provide an indication of the folding enhancement achieved following the directed evolution method of the invention. In one embodiment, random insertion mutant libraries may be created using, for example, transposon-mediated mutagenesis techniques (Gorshin et al., 2000, Nature Biotechnol. 18: 97) and commercially available kits (e.g., Epicentre Technologies, Madison, Wis.). More robustly folding mutants in the evolved mutant library relative to the unevolved mutant polypeptide library provides an indication of the extent to which the evolved test polypeptide has enhanced folding properties. Similarly, the tolerance to larger insertions may provide an indication of the extent to which the evolved polypeptide has acquired enhanced folding properties.

Another method for evaluating acquisition of enhanced folding in evolved polypeptides involves the generation of circular permutants of the test evolved polypeptide. Briefly, the native N and C termini of the test evolved polypeptide are ligated together at the polynucleotide level, and start codons are randomly introduced into the coding sequence. A library of circular permutants is then expressed and compared to a library of circular permutants generated from the unevolved polypeptide, wherein the relative number of permissive sites for the randomly inserted start codons may be determined by a functional screen indicative of correct folding and thereby provides an indication of folding enhancement acquired by the evolved polypeptide.

In general, "superfolder" polypeptides will enable the generation of a greater range of circular permutants, relative to the wild type or pre-evolved polypeptide from which the superfolder was generated. This is a particularly important consideration in regards to fluorescent proteins, for which the generation of a variety of circular permutants is desirable for developing appropriate FRET pairs. FRET, or Fluorescence Resonance Energy Transfer, is the non-radiative transfer of energy from a donor fluorophore to an acceptor fluorophore spatially located within about 80 Angstroms of each other. The relative geometric context of the two fluorophores is an important component of FRET. Circular permutation may be used to alter the geometric orientation of the fluorophores relative to each other.

Functional assays may also be utilized where appropriate, and may be preferred. For example, a biological property of a protein of interest may be measured as an indication of folding. For example, if the protein is a fluorescent or chromophoric protein, the presence and intensity of emitted fluorescence or color, respectively, provides an indication of folding. Brighter fluorescence, for example, provides an indication of better folding in relation to dimmer variants of P (or colonies expressing P).

Additionally, misfolded proteins often aggregate and become insoluble, and a corresponding test may be applied by first determining that the correctly folded protein is soluble, and that the incorrectly folded protein is insoluble. For example, if the protein is an enzyme, and the correctly folded enzyme is active and its activity can be measured, and the soluble protein is active while the insoluble protein is inactive, then if $P_1$-Xid-$P_2$ is soluble and active, P would be inferred to be correctly folded. If $P_1$-Xid-$P_2$ is not active, and also insoluble, then it may be concluded that P is misfolded. $P_1$-Xid-$P_2$ might be active and yet insoluble, or $P_1$-Xid-$P_2$ might be soluble but inactive.

Alternatively, the solubility of $P_1$-Xid-$P_2$ could be used to determine the folding of P in $P_1$-Xid-$P_2$ as above. If the correctly folded version of P binds a target peptide Pt, and the binding can be detected, for example if Pt is an antibody that is conjugated to a reporter domain. R, or has and intrinsically detectable signal, or P and Pt are binding or folding partners, or P and Pt comprise two of at least two domains of a split protein or multiprotein complex, which has a detectable phenotype when the fragments or components are assembled, the assembly dependent on the correct folding of P in $P_1$-Xid-$P_2$. Also, folding of P could be measured by the resistance of P to limited proteolysis coupled to selection by phage display (in which case the method is a way of increasing the stringency of selection by phage display (Martin et al., 2001, J. Mol. Biol. 309(3): 717-26.

Also, the folding of P in $P_1$-Xid-$P_2$ could be detected by using a folding reporter such as GFP or some other protein with a detectable phenotype (enzyme activity, fluorescence, ability to bind other proteins or molecules) such that the detection of R in $P_1$-Xid-$P_2$-R is an indication of correct folding by R and therefore of P.

Detectable phenotypes are not limited to enzymatic activity or fluorescence. For example, the phenotype associated with correct folding of P could be the ability of P to bind a target molecule, the binding event being detectable by some means. In this case, the reporter domain might not have activity until the binding event occurs. For example, P could be a component of a complementation system or split protein such as the S-protein or S-peptide (which associate to form active RNASE-A), or the split dihydrofolate reductase, or the split beta lactamase (Galarneau, A; Primeau, M; Trudeau, L E; Michnick, S W Beta-lactamase protein fragment complementation assays as in vivo and in vitro sensors of protein-protein interactions Nature Biotechnology; June 2002; v. 20, no. 6, p. 619-622, or the split beta galactosidase (Wigley, W C; Stidham, R D; Smith, N M; Hunt, J F; Thomas, P J Protein solubility and folding monitored in vivo by structural complementation of a genetic marker protein Nature Biotechnology; February 2001; v. 19, no. 2, p. 131-136). The split proteins could be self-assembling, or require the association via fused partners that are capable of association, such as coiled-coils. (Galarneau, A; Primeau, M; Trudeau, L E; Michnick, S W Beta-lactamase protein fragment complementation assays as in vivo and in vitro sensors of protein-protein interactions Nature Biotechnology; June 2002; v. 20, no. 6, p. 619-622.

It is desirable that the signal level given as the detectable phenotype be proportionate to the amount of correctly folded reporter molecule. The binding event could be that of an antibody that recognizes an epitope of the correctly-folded target P, binding of the antibody measured by some means such as the enzymatic activity of a linked enzyme.

The mutated target polypeptides tested for folding activity in the context of a fusion protein comprising a poorly folding domain, which was selected for its poor folding properties in the expression system of interest. Folding activity is typically measured by measuring the amount of reporter activity, as the amount of active protein is dependent on proper folding. The target polypeptide may itself have reporter activity or may be joined to another molecule that has reporter activity.

Reporter molecules that can be used include those with activities that can be directly measured, e.g., fluorescent polypeptides, e.g., green, blue, yellow, or red fluorescent proteins and variants of those proteins; polypeptides encoded by antibiotic resistance genes; and molecules that can be indirectly measured, e.g., enzymes such as β-galactosidase, alkaline phosphatase, horse radish peroxidase, β-lactamase, or other enzymes that require a secondary detection reagent. Other polypeptides such as antibodies or other binding protein, may be measured by assessing their ability to specifically bind to a binding partner. Other polypeptides could be parts of 'split protein' complementing pairs. Such as DHFR (1-105) and DHFR (106-186) from murine dihydrofolate reductase (see, Remy et al., 1999, Proc. Natl. Acad. Sci. USA, 96: 5394-5399). Also, various split proteins such as beta lactamase, beta galactosidase, etc. Also, this assay can be performed in vitro using cell free-expression and appropriate substrates (fluorogenic, chemiluminescent, etc.; see Galacton Star reagent for beta galactosidase, a ribonucleic acid donor/quencher substrate which is the target of RNASE-A, for example, the split S-protein S-peptide system (Novagen) Kelemen, B R; Klink, T A; Behlke, M A; Eubanks, S R; Leland, P A; Raines, R T Hypersensitive substrate for ribonucleases Nucleic Acids Research; Sep. 15 1999; v. 27, no. 18, p. 3696-3701. Various non-polypeptide reporters may also be employed, such as cyclic arseno compounds capable of binding to poly cysteine tags on proteins and cyclizing to become fluorescent. (Adams et al., 2002, Journal Of The American Chemical Society, 124: 6063-6076). Polypeptide with enhanced folding properties are then selected and can be obtained in the quantity desired using various expression systems.

Expression Cassettes And Host Cells For Expressing Polypeptides

There are many expression systems for producing the proteins of the invention, e.g., the GFP variants with enhanced folding or the fusion proteins, that are well know to those of ordinary skill in the art. (See, e.g., *Gene Expression Systems*, Fernandes and Hoeffler, Eds. Academic Press, 1999; Ausubel, supra; Russell & Sambrook, supra.) The protein may be, but need not be, expressed in the system in which the folding properties were determined. The polynucleotide that encodes the fusion polypeptide is placed under the control of a promoter that is functional in the desired host cell. An extremely wide variety of promoters are available, and can be used in the expression vectors of the invention, depending on the particular application. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res*. (1980) 8: 4057), the tac promoter (DeBoer, et al., *Proc. Natl. Acad. Sci. U.S.A*. (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, various pET vectors (e.g., pET23D, pETCK3[88]), λ-phage derived vectors, p15A-based vectors (Rose, *Nucleic Acids Res*. (1988) 16:355 and 356) and fusion expression systems such as GST. Epitope tags can also be added to recombinant proteins to provide convenient methods of isolation, e.g., c-myc, HA-tag, 6-His tag, maltose binding protein, VSV-G tag, anti-DYKDDDDK (SEQ ID NO: 28) tag, or any such tag, a large number of which are well known to those of skill in the art.

For expression of fusion polypeptides in prokaryotic cells other than *E. coli*, regulatory sequences for transcription and translation that function in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Russell & Sambrook and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Similarly, the for expression of fusion polypeptides in eukaryotic cells, transcription and translation sequences that function in the particular eukaryotic species are required. For example, eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include those employing the CMV promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol*.; Tabor et al. (1985) *Proc. Nat'l. Acad.*

*Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in host bacterial cells, or able to integrate into the genome of host bacterial cells. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*., Academic Press, Inc. N.Y. (1990)). Substantially pure compositions of at least about 90 to 95% homogeneity are preferred, and 98 to 99% or more homogeneity are most preferred.

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells).

Additional expression vectors suitable for attaching a tag, and corresponding detection systems, are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Uses of Evolved Polypeptides with Improved Folding and Stability Properties:

Evolved polypeptides with improved folding and stability can be used in any number of applications. In particular, those target polypeptides that can be used as reporter proteins can be used to report expression level, unaffected by folding. Conventional methods for assessing protein expression in vivo, require poorly folded proteins to be unfolded, for example, prior to probing with labeled antibodies. These proteins do not generally refold well prior to probing or sandwich ELISA, leading to an underestimate of expression level as the misfolded aggregated protein domains are not available for binding by the antibody. Obviously this denaturing method is not suited for intact, high throughput in vivo protein expression monitoring. Furthermore, conventional methods for assessing protein expression in vivo do not work well when the protein domains are buried in aggregates. In contrast, the reporter activity of a polypeptide that has enhanced folding can more accurately reflect expression.

The invention's method of generating thermostable proteins will be particularly applicable to a wide variety of target proteins. For example, thermostable variants of various lipases and proteases used in detergent formulations may be highly desirable inasmuch as such variants would be expected to be active at higher temperatures and for longer periods of time. Similarly, other enzymes used in various industrial processes could be evolved using the method of the invention to produce variants which operate for longer periods of time in such high temperature processes. Additionally, many other enzymes are difficult to incorporates into high temperature industrial processes. For example, thermostable variants of cellulases and other enzymes involved in the production of biofuels would facilitate integration into such processes at higher temperatures. Many enzymes used in various molecular biology applications, such as polymerases, helicases, ligases, and the like could be improved to attain greater thermostability, thus enabling retention of biological activity within high temperature environments.

In particular, the thermostable fluorescent proteins described herein may be used in a variety of applications in which enhanced stability, including particularly thermostability, is required. Thermostable fluorescent proteins in a number of challenging environments, they may find use in processes, assays and other applications in which a high degree of stability is required in order for the fluorescent phenotype to survive. For example, the eCGPs generated by the internal destabilization methods of the invention (see Examples) show a remarkable degree of thermostability. Some of the eCGPs, such as eCGP23 and eCGP123, are able to retain fluorescence after being exposed to very high temperatures. For example, both eCGP23 and eCGP123 are able to recover almost completely after heating at 99° C., a temperature that irreversibly destroys folding in all other fluorescent proteins tested. Similarly, both of these eCGPs are able to retain some degree of fluorescence even at the high temperature of 99° C. Additionally, both of these eCGPs retain approximately 85% of their ambient temperature fluorescence levels for at least 14 hours at 80° C. Thus, these two eCGPs demonstrate remarkable and hitherto unreported levels of thermostability for fluorescent proteins, and should find use in various applications for which thermostability as well as increased stability generally are required. Detailed characterization of eCGPs is provided in the Examples which follow.

In biotechnological applications, protein thermostabilization leads to longer survival times, improved reaction kinetics and diminished microbial contamination. In the pharmaceutical arena, thermostability of protein therapeutics leads to longer serum half lives and more effective drugs. Thermostability is also important in the use of proteins as scaffolds to generate libraries of specific binders: if a starting scaffold is more stable, it will be more tolerant to the destabilizing effects of mutations, or insertions, used to mediate binding. Finally, proteins of increased thermostability are generally more resistant to mutations than the protein from which they are derived, promoting evolvability by providing greater permissivity to mutations leading to novel functions[1, 2].

Various aspects of the invention are further described and illustrated by way of the several examples which follow, none of which are intended to limit the scope of the invention.

EXAMPLES

Example 1

Generation and Characterization of Evolved Consensus Green Fluorescent Proteins Using Internal Destabilization and Directed Evolution Materials and Methods:
HCDR3 Insertions into CGP The 60-bp HCDR3 sequences (acting as folding interference domains) were inserted into CGP by PCR assembly. The PCR primers generally contained a 20-bp long CGP specific sequence and a 40-bp 5' tail encoding one part of the HCDR3. The two HCDR3 containing primers had a 20-bp homologous overlapping sequence to facilitate PCR assembly. The following general procedure was used, unless otherwise described. The reaction was performed in 50 µl containing 1× Thermopol buffer (NEB), 250 µM dNTP, 0.5 µM of each primers and 1.25 U Taq polymerase (NEB) with cycling conditions as follows: 1 min initial denature at 94° C., then 30 cycles of 94° C., 15 sec, 55° C., 15 sec, 30 sec, 72° C., then a final elongation of 5 min at 72° C. TABLE IV contains the primer sequences. The nucleotide sequence encoding the 20 amino acid long HCDR3 sequence was different for each insert, using different codons, in order to prevent homologous recombination in the bacteria. Inserting single HCDR3s into CGP was achieved by performing two PCR reactions with 1) CGP-5' and CDR-loop-x-R-CGP and 2) CDR-loop-x-F-CGP and CGP-3' primers. The x denotes the loop number. The resulting bands were gel purified and assembled in an assembly reaction with CGP-5' and CGP-3' primers added after 25 cycles.

Multiple HCDR3s were inserted similarly. The double inserted libraries were assembled from 3 fragments; the triple inserted libraries used 4 fragments. For example the double library containing HCDR3 insert in loop 1 and loop 3 were assembled from fragments amplified using these primers: 1) CGP-5' and CDR-loop-1-R-CGP; 2) CDR-loop1-F-CGP and CDR-loop-3-R-CGP; 3) CDR-loop-3-F-CGP and CGP-3' (see TABLE IV). Other libraries were created similarly using the appropriate primers.

DNA Shuffling

DNA shuffling was performed according to Zhao, 1997[91]. Briefly, 10 µg of template DNA, CGP containing 1, 2 or 3 CDR3 inserts, were digested with 1 U of DNAse I (NEB) for 10 minutes at 15° C. in 50 mM Tris-Ac pH 7.5, 2 mM CoCl$_2$. The reaction was terminated by heating for 3 minutes at 90° C., and DNA fragments purified by spin-column chromatography on Sephadex-25 (GE Healthcare) columns. The digested template was assembled in a primerless PCR reaction with 1.25 U Pfu Exo DNA polymerase (Stratagene) using 15 µl of the digested template in a buffer containing 1×Pfu reaction buffer, 0.4 mM dNTP in a 25 µl reaction volume. The cycling conditions were 97° C., 3 min initial denature, then 35 cycles of 96° C. 25 sec, 56° C., 25 sec, 72° C. 1 min, with a final extension for 5 min at 72° C. 3 µl of the amplification reaction was amplified by 2.5 U Taq polymerase (NEB) in a 100 µl reaction containing 1× Thermopol buffer (NEB), 250 µM dNTP, 0.5 µM of CGP-5' and CGP-3' primers with the following cycling: 1 minute initial denature at 94° C., then 30 cycles of 94° C., 15 sec; 60° C., 15 sec; 72° C. 30 sec; with a final elongation for 5 minutes at 72° C. The PCR product was phenol/chloroform extracted and purified by spin-columns containing Sephadex G-75 (GE Healthcare). The purified DNA was digested with BssHII (NEB) and NheI (NEB) according to the manufacturer's recommendation and cloned into pETCK3 (Kiss et al., 2006[88]). The ligation was electroporated into BL21 (DE3) Gold electrocompetent cells. The cells were plated on nitrocellulose filters on LB agar plates containing 50 µg/ml kanamycin and 3% glucose and grown overnight at 37° C. The filters were transferred onto kanamycin LB plates containing 1 µg/ml IPTG and induced for 4 hours at 30° C. Colonies that were greenest after induction were picked and sequenced. The selected clones for the next round of shuffling were pooled and the CDR3 sequences were recreated by PCR assembly using CDR3 specific primers that lacked any CGP specific sequences.

Protein Expression and Purification

Plasmids encoding the fluorescent proteins cloned into pETCK3 were transformed into E. coli BL21 DE3 cells (Stratagene). Single colony transformants were cultured overnight at 37° in Luria Broth with 50 µg/ml kanamycin. The overnight cultures were suspended in fresh Terrific Broth containing 50 µg/ml Kanamycin and transferred to the Kalypsys Airlift Fermentation System, based on the system described by Lesley et al[89]. Cultures were grown at 37° for 3 hours (optical density of 1.5-2.5 (600 nm)) on 100% air. The temperature was reduced to 30° and IPTG added to a final concentration of 1 mM. After 4 hour of growth, 50% air and 50% oxygen, cells were harvested by centrifugation and the resulting pellets were stored overnight at −20°. The bacteria pellets were removed from storage, thawed, and suspended in lysis buffer (500 mM NaCl, 5 mM Imidazole). Cells were lysed by sonication in the Kalypsys pre-chilled rotor, using 4 cycles of one minute sonication (duty cycle 100, amplitude 75) followed by one minute rest, then centrifuged at 7000×g for 30 min. The Kalypsys Robot transferred the supernatant to the nickel columns (Nickel Chloride bound to GE Chelating Sepharose Fast Flow Resin) which were washed with (500 mM NaCl, 5 mM Imidazole). The bound proteins were eluted with (500 mM NaCl, 500 mM Imidazole).

The fluorescence of the purified proteins was measured (SPECTRAFluor Plus, 492 nm, optimal gain 44) in arbitrary fluorescence units measured at 535 nm. An SDS-PAGE gel was loaded with samples based on equal fluorescence and proteins were quantified against protein standards using the Syngene GeneTool Software.

Thermostability Measurements

Proteins of equal fluorescence were diluted into 50 μl of TNG buffer (100 mM Tris-Ac pH 7.5, 100 mM NaCl, 10% glycerol) and placed into 0.2 ml thin wall PCR tubes. Thermal cyclings were performed in a Rotor-Gene 6000 real time PCR machine (Corbett Life Science). Fluorescence and gain were adjusted so that the fluorescence of the starting samples was between 90-100. The melting profile was resolved between 30° C. and 99° C. Temperature was raised by 0.5° C. increments. The samples were incubated at each temperature for 60 sec.

Single Molecule Spectroscopy

Fluorescence Correlation Spectroscopy was performed in the same setup described previously. Quantum yield was determined relative to Fluorescein from the ratio of integrated fluorescence signal to the absorbance at 488 nm.

Chemical Denaturation

Equilibrium fluorescence values were measured by diluting guanidine hydrochloride denatured eCGP variants into TNG containing 5 mM DTT to various final guanidine concentrations between 1 and 8 M in increments of 0.15 M guanidine, and allowing refolding to proceed at 15° C. Fluorescence values were measured using a FL600 Microplate Fluorescence Reader (488-nm excitation, 530-nm emission, 10-nm band pass) and scaled by dividing by the fluorescence levels of corresponding nondenatured samples diluted in parallel as a reference. Midpoint recovery concentrations of guanidine Cm (recovery of 50% of the initial fluorescence) were determined from sigmoidal fits using SOLVER in EXCEL, to the scaled fluorescence value F using the equation Fj ¼ a+b/(1+(Cj/Cm)h), where a, b, Cm and h are adjustable parameters, and Cj is the molarity of the guanidine in the refolding experiment j. The data were used to calculate the dependence of the standard free energy of denaturation, DG1 ¼–RT ln K, on guanidine concentration, where R is the gas constant, T is the absolute temperature and K is the equilibrium constant, which can be calculated from the experimental data by using the standard equation K ¼ [(y)N–(y)]/[(y)–(y)D], where (y) is the observed value of the parameter used to follow unfolding, and (y)N and (y)D are the (y) values for the native state and the denatured state, respectively, under the same conditions under which (y) was measured.

Results

Evolutionary Strategy

A recursive evolutionary strategy was employed, in which single inserts were grafted into exposed loops in such a way that upon each insertion, folding and function were significantly affected but not destroyed (FIG. 1A). This provides a baseline which may be improved by evolution. Upon overcoming the effect of a single insert, the procedure is then repeated with a second, and finally a third insert. In this way it is possible to overcome a final destabilizing force that would completely destroy both folding and function if applied in a single step.

This method was applied to CGP by modeling the structure of this protein on that of Dronpa, the closest fluorescent protein for which a structure has been determined (Wilmann et al., 2006[90]), and targeting three identified beta turns for insertion. These were termed loop 1 (V18/N19), loop 2 (E96/D97) and loop 3 (E164/G165). The destabilizing insert used was based on a human heavy chain third antibody complementarity determining region (HCDR3) sequence. Although HCDR3s are highly diverse loops, they are embedded into a relatively conserved beta sheet structure[66], as a result of which the amino acids at either end (cysteine 104 and tryptophan 119; IMGT numbering[67] are always joined by two hydrogen bonds. As the usual distance between these two amino acids is similar to that between amino acids just before the turns described above, it was presumed that the insertion of such a sequence into a CGP loop would probably be disruptive to folding, but would not destroy it completely. In order to avoid the presence of an unpaired cysteine (the HCDR3 N terminal cysteine normally disulfide bonds with another cysteine in framework one), this codon was mutated to a serine, which is able to form the same hydrogen bonds. The final sequence used (SARSFYLQSDLAAGDFDSWG; SEQ ID NO: 26), based on a randomly picked HCDR3 with a few internal changes to facilitate cloning, was inserted at V18/N19 and E96/D97 in two independent PCR assemblies. As expected, this resulted in a significant reduction in the fluorescence of induced bacterial colonies as shown in FIG. 1B.

After three rounds of error prone PCR and DNA shuffling on these two modified genes, the fluorescence of induced bacterial colonies increased significantly, some reaching the levels of the original CGP protein (FIG. 1B). During the mutation and selection process, the gene was always reassembled using the HCDR3 as an anchor, in order to force mutations into the CGP and not the inserted HCDR3. After three rounds, PCR assembly was again used to insert the same HCDR3 amino acid sequence at position E164/G165 of the genes from 23 fluorescent evolved clones containing an insert at V18/N19 and 22 clones containing an insert at E96/D97. The DNA sequence encoding the HCDR3 insert was altered to avoid recombination with the first insert. A significant reduction in fluorescence was again observed, which could be restored after three further rounds of evolution, carried out as before by PCR assembly of now three fragments using the two HCDR3 inserts as anchors.

The process was repeated a final time, pooling fluorescent colonies and inserting the HCDR3 into three sites (V18/N19, E96/D97 and E164/G165). With the proteins containing three inserts, four rounds of evolution were required before fluorescence was significantly restored. After each round of evolution approximately 100 clones were sequenced, allowing analysis of the accumulated mutations (FIG. 2). It should be pointed out that although the use of assembly PCR to insert each additional loop into CGP allowed mutations accumulated in previous rounds to persist into the following evolutionary rounds, this was not true of those mutations close to the insert site, which were "overridden" by the primers used for insertion in the first round. In subsequent rounds, the HCDR3 insertion sequences themselves were used for assembly, allowing reappearance of mutations close to insertions. In general 4 classes of mutations were observed: 1) those (e.g. D7E, M40L, T59P, V60A) appearing immediately and retained throughout; 2) those which first appear with a single insert, are specific for that insert (e.g. Q98H for 18/19 inserts, and K22E for 96/97 inserts), are retained in the presence of two inserts, but are then lost when three inserts are present; 3) those appearing in the presence of two inserts, and persisting in the presence of three inserts (e.g. E164K, K190E, K208R); and 4) those (e.g. A17S, K30I, F34Y, A53S) which are only found when three inserts are present.

Gene Synthesis

Genes corresponding to the proteins without inserts were synthesized (Blue Heron Biotechnology) for each of the five evolutionary paths (FIG. 1A). Synthesized genes contained those mutations that led to amino acid changes in at least 20% of sequences, and silent mutations found in greater than 90% of sequences. In addition, one silent mutation frequently found adjacent to a non-silent mutation was also included. In order to concentrate on mutations responsible for global increases in stability, rather than mutations responding to specific changes in secondary structure adjacent to the insert site, those mutations found within two amino acids of an insertion point were not included, even though there are examples of mutations in loops (e.g. Y39N in sfGFP[7]) which are globally stabilizing.

The aligned amino acid sequences of the final genes synthesized, compared to CGP, are shown in FIG. 3. As can be seen, some mutations (eight of eighteen) recapitulate amino acids found in fluorescent proteins used to create the CGP consensus sequence. The remaining ten mutations are equally split between those found in mAG (and modified for CGP) and those not previously found in any other fluorescent protein, and unique to these evolved proteins. Of the mutations which revert back to mAG, three (D7E, M40L, A69T) are found in most of the evolved proteins, while the remaining two (K32N and F34Y) are each found in only one or two of the proteins. The reversion of such presumably destabilizing mutations in consensus sequences is similar to those found in other examples[37-40], and underlie the importance of examining the roles of individual amino acids for their contributions to stability.

Properties of eCGPs

Figure 4A:
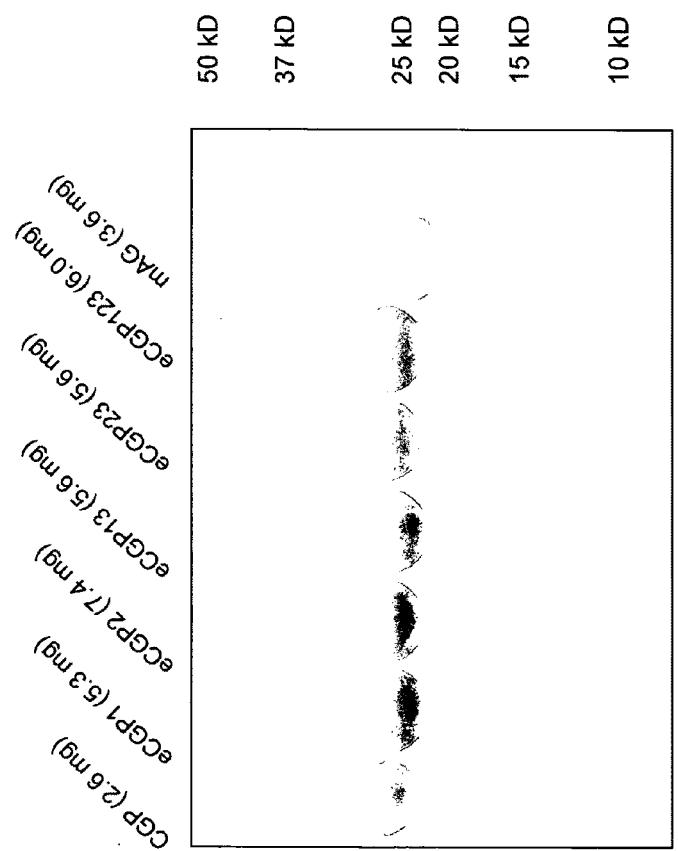
FIG. 4. Absorption and emission of purified thermostable fluorescent protein variants. (A) shows purification and expression levels of the different purified proteins. The amounts given correspond to the total amount of purified protein from 60 ml fermentation volume. (B) shows absorption and emission of the purified CGP, various eCGP proteins, and mAG normalized to 1 for the respective peaks. Peak values are provided in TABLE I.

The five fluorescent protein genes were cloned into pETCK3[88] and expressed in BL21. All were able to direct the synthesis of fluorescent proteins at levels comparable to, or exceeding, CGP and mAG (FIG. 4a). The excitation/emission properties (FIG. 4b and TABLE I) of the proteins were similar to either CGP (eCGP1 and eCGP2) or mAG (eCGP13, eCGP23 and eCGP123), with the CGP series being slightly red shifted compared to the mAG series. The quantum yields of the proteins ranged from 0.54 (eCGP1) to 0.75 (eCGP13), not too dissimilar to that of mAG (0.83). All proteins were monomeric as determined by gel filtration (not shown) or fluorescence correlation spectroscopy (TABLE I).

In a first test of protein thermostability, the proteins were slowly melted at 0.5° C./min, using a real time PCR machine (Rotor-Gene 6000, Corbett Life Sciences, FIG. 5a) which monitored fluorescence changes with temperature in real time. The temperature was gradually increased to 99° C., and then returned to 30° C., to monitor recovery. After approximately 38° C., all proteins showed a reduction in fluorescent with increasing temperature as shown in FIG. 5a. This fluorescence loss is characteristic of fluorescent proteins, and thought to be due to two components: changes in the immediate fluorophore environment caused by increased thermal vibrations, and unfolding of the proteins. Fluorescence loss due to the former are immediately reversible and do not represent unfolding[68, 69], while fluorescence loss due to the latter require refolding for fluorescence to return. As temperature increases, the proportion of fluorescence loss due to these two components will vary, depending upon the stability of the protein and the temperature. In general, little of the fluorescence loss is caused by unfolding until the temperature at which cooperative unfolding starts is reached. This is recognized as an inflection point in the melting curve, and represents the point at which unfolding suddenly accelerates. This is similar to changes in CD spectra observed with increasing temperature[70].

All proteins, with the exception of eCGP23 and eCGP123, showed cooperative unfolding as the temperature was increased, with inflection points between 73 and 87° C., cooperative transition midpoints two to three degrees later, and characteristic steeper denaturation curves[69]. eCGP23 and eCGP123 were characterized by the absence of a clear cooperative transition, and even at 99° C., some fluorescence remained (FIG. 5b). Recovery upon cooling to 30° C. resulted in essentially complete (96%) recovery of eCGP123, and 85% recovery of eCGP23 (TABLE II). The remaining proteins recovered to varying degrees, depending upon the degree of evolution. For all the evolved proteins, 54-61% of the fluorescence recovery occurred instantaneously, while for mAG and CGP, the instant recovery was lower (35% and 44% respectively).

The same order of stability was observed when the proteins were treated with multiple heat cool cycles (equivalent to 60 "PCR cycles" with 1 minute denaturation at 99° C. and 2 minutes recovery at 30° C.—FIG. 5c for CGP and eCGP123). eCGP123 and eCGP23 continued to show low levels of fluorescence at 99° C., while the other proteins rapidly lost fluorescence at this temperature. After 60 heat/cool cycles, and at each return to 30° C., the fluorescence of the two stable proteins returned to their pretreatment levels, while the remaining proteins showed a dramatic drop after the first heat cycle, with fluorescence further decreasing to zero with additional cycles, and little recovery upon return to 30° C.

One last test of thermal stability was the ability of the proteins to resist high temperature for prolonged periods. The proteins were all heated to 80° C. or 85° C. This resulted in the initial rapid loss of over 80% fluorescence due to thermal vibration, which stabilized after about six to seven minutes. The fluorescence of the different proteins was normalized at this time (arrow FIG. 5d), and further fluorescence loss monitored for 14 hours. eCGP123 and eCGP23 lost approximately 15% fluorescence after 14 hours at 80° C., while all the other proteins, with the exception of eCGP13 which was intermediate, had lost all fluorescence by 2-3 hours (FIG. 5e). At 85° C. the fluorescence loss of the less stable proteins (CGP, eCGP1 and mAG) was complete by five minutes. eCGP1 and eCGP13 showed complete loss of fluorescence by three hours, while after 14 hours eCGP23 and eCGP123 still retained approximately 10-15% of the normalized fluorescence at 85° C. (FIG. 5F).

Figure 6B:
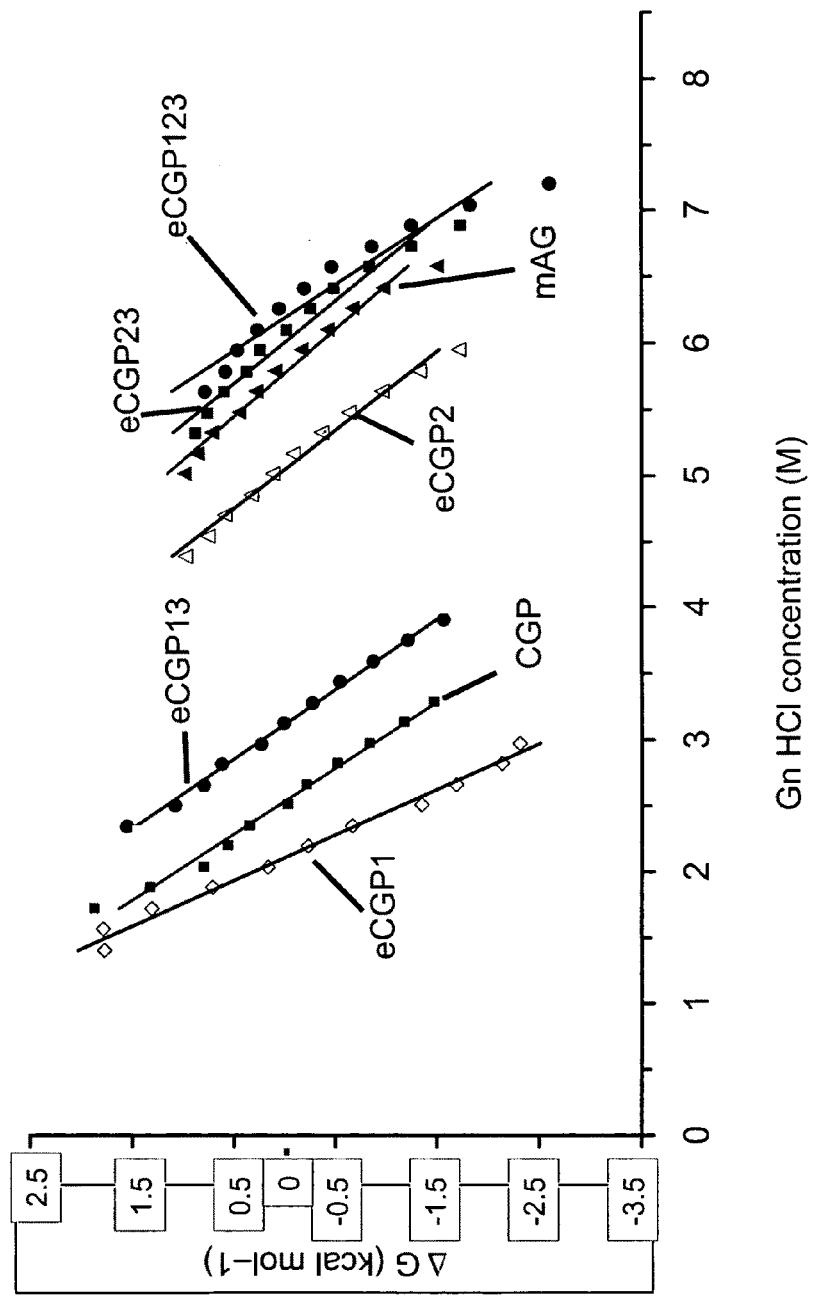

Thermal denaturation was monitored using measures independent of intrinsic fluorescence. However, the Thermofluor assay[71, 72] was unsuccessful due to degradation of the Sypro Orange at temperatures above 80° C., and it also proved impossible to carry out circular dichroism at the high temperatures required.

eCGP stability was also studied by denaturation in guanidine hydrochloride (FIG. 6A and TABLE III) with unfolding monitored by fluorescence. At equilibrium, which required over two weeks, eCGP123 and eCGP23 were again the most stable proteins, with melting (kd) occurring at 6.45 M guanidine for eCGP123 and 6.19 M for eCGP23. However, the order of stability for the remaining proteins was slightly different to that observed with thermal denaturation, with eCGP2 being significantly more stable than eCGP13, and CGP being more stable than eCGP1. By extrapolating a natural log fit of the sigmoidal denaturation curve to infinite dilution (FIG. 6B), the □G was determined, which again showed eCGP123 to be by far the most stable protein at 12.4 kcal/mol.

Figure 6C:
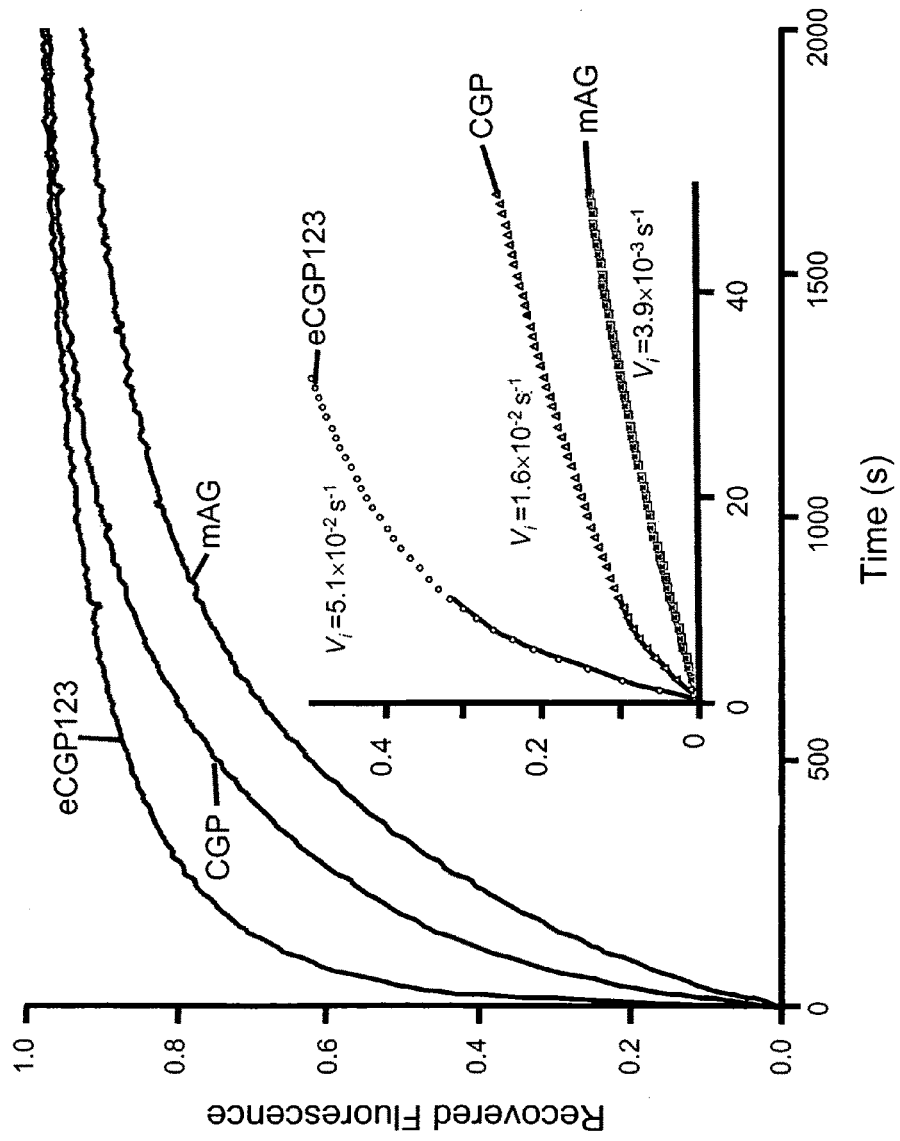

CGP, mAG, and eCGP123, representing the starting, evolved, and closest natural proteins, were also analyzed for folding kinetics. Proteins were denatured in Gdn HCl, and fluorescence recovery monitored upon dilution into fresh buffer. Although CGP is much less stable than mAG, it displayed an approximately 3.5-fold faster initial rate for fluorescence recovery relative to the more stable mAG (FIG. 6C, inset). This faster folding behavior is consistent with the observation that CGP also unfolds much faster than mAG in 8 M Gdn HCl as noted above. Such behavior is typical of simple two-state folders, for which increased forward folding rate is mirrored by a corresponding increased unfolding rate.

eCGP123 folds 4-fold faster than CGP. The increased stability of eCGP123 relative to CGP likely results from the very slow unfolding of eCGP123 consistent with the slow approach to equilibrium during the equilibrium Gdn HCl unfolding experiments and the thermal stability.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE I

|  | Absorption max (nm) | Emission max (nm) | Q.Y. | $R_0$, nm |
|---|---|---|---|---|
| CGP | 503 | 515 | 0.66 | 20.3 |
| eCGP1 | 504 | 514 | 0.54 | 19.3 |
| eCGP2 | 501 | 511 | 0.59 | 22.9 |
| eCGP13 | 493 | 505 | 0.75 | 20.9 |
| eCGP23 | 493 | 504 | 0.73 | 16.6 |
| eCGP123 | 493 | 504 | 0.69 | 21.3 |
| mAG | 491 | 505 | 0.83 | 18.6 |

TABLE II

RECOVERY AFTER THERMAL MELT

|  | % instant recovery | % final recovery | instant recovery as % of total recovery |
|---|---|---|---|
| eCGP123 | 58.8 | 96.0 | 61.3 |
| eCGP23 | 47.7 | 85.5 | 55.8 |
| eCGP13 | 33.4 | 55.2 | 60.5 |
| eCGP2 | 12.0 | 22.3 | 53.8 |
| eCGP1 | 15.0 | 27.0 | 55.6 |
| CGP | 8.0 | 18 | 44.4 |
| mAG | 7.5 | 21.3 | 35.2 |

TABLE III

STABILITY BY GUANIDINE DENATURATION

|  | kd [GnHCl] | h | $\Delta G(H_2O)$ | m |
|---|---|---|---|---|
| CGP | 2.56 | 9.71 | 4.9 ± 0.1 | 1.9 ± 0.05 |
| eCGP1 | 2.12 | 12.45 | 6.1 ± 0.0 | 2.9 ± 0.02 |
| eCGP2 | 5.12 | 15.53 | 8.5 ± 0.5 | 1.7 ± 0.10 |

TABLE III-continued

STABILITY BY GUANIDINE DENATURATION

|  | kd [GnHCl] | h | $\Delta G(H_2O)$ | m |
|---|---|---|---|---|
| eCGP13 | 3.15 | 11.08 | 5.9 ± 0.1 | 1.9 ± 0.04 |
| eCGP23 | 6.19 | 14.43 | 9.8 ± 1.4 | 1.6 ± 0.23 |
| eCGP123 | 6.45 | 14.29 | 12.4 ± 2.2 | 2.0 ± 0.33 |
| mAG | 5.86 | 16.66 | 8.9 ± 0.9 | 1.5 ± 0.15 |

TABLE IV

OLIGONUCLEOTIDES USED

| Name | Oligo Sequence |
|---|---|
| CDR3-loop1-F | CTTGCAATCCGATCTTGCAGCAGGTGACTTCGAC TCTTGGGGT [SEQ ID NO: 11] |
| CDR3-loop1-F-CGP | CTTGCAATCCGATCTTGCAGCAGGTGACTTCGAC TCTTGGGGTAACGGCCATAAATTTGTAATTG [SEQ ID NO: 12] |
| CDR3-loop1-R | CACCTGCTGCAAGATCGGATTGCAAGTAGAAGCT ACGAGCACT [SEQ ID NO: 13] |
| CDR3-loop1-R-CGP | CACCTGCTGCAAGATCGGATTGCAAGTAGAAGCT ACGAGCACTAACGGCACCTTCCATACGC [SEQ ID NO: 14] |
| CDR3-loop2-F | CCTCCAAAGTGACTTAGCTGCCGGCGATTTTGAT AGCTGGGGC [SEQ ID NO: 15] |
| CDR3-loop2-F-CGP | CCTCCAAAGTGACTTAGCTGCCGGCGATTTTGAT AGCTGGGGCGATCAAGGAATTTGTATCGC [SEQ ID NO: 16] |
| CDR3-loop2-R | CGCCGGCAGCTAAGTCACTTTGGAGGTAAAATGA GCGGGCCGA [SEQ ID NO: 17] |
| CDR3-loop2-R-CGP | CGCCGGCAGCTAAGTCACTTTGGAGGTAAAATGA GCGGGCCGATTCATAGGTCATAGAGCGTTC [SEQ ID NO: 18] |
| CDR3-loop3-F | TTTACAGTCTGACTTGGCGGCTGGGGATTTCGAT TCGTGGGGG [SEQ ID NO: 19] |
| CDR3-loop3-F-CGP | TTTACAGTCTGACTTGGCGGCTGGGGATTTCGAT TCGTGGGGGGGAGGTGGACACTACCGCTG [SEQ ID NO: 20] |
| CDR3-loop3-R | CCCCAGCCGCCAAGTCAGACTGTAAATAGAAAGA CCGCGCAGA [SEQ ID NO: 21] |
| CDR3-loop3-R-CGP | CCCCAGCCGCCAAGTCAGACTGTAAATAGAAAGA CCGCGCAGATTCGAGCAGAAGTGCCATG [SEQ ID NO: 22] |
| CGP-3' | TTTGCCGCTAGCTTTAGCCTGAGACGGTAACATA GAATAGC [SEQ ID NO: 23] |
| CGP-5' | TACATATGGGCGCGCATGCCTCAGTAATTAAACC G [SEQ ID NO: 24] |

TABLE OF DNA AND PROTEIN SEQUENCES eCGP DNA Sequences:

eCGP1 [SEQ ID NO: 1]
```
  1 ATGTCAG TAATTAAACC GGAAATGAAA ATTAAATTGC GTATGGAAGG TGCCGTTAAC GGCCATAAAT TTGTAATTGA AGGGGAAGGA
    AAAGGCAACC
 98 CATTCGAAGG AACCCAGACC CTGGATTTAA CCGTAAAAGA AGGCGCACCT CTCCCTTTCG CGTACGACAT CCTCACCCCA GTCTTCCAAT
    ACGGCAATCG
198 CGCTTTCGCC AAATACCCAC AAGATATTCC AGACTATTTT AAACAAACAT TCCCCGAAGG CTATTCTTGG AACGCTCTA TGACCTATGA
    AGATCATGGA
298 ATTTGTATCG CTACCTCCGA CATTACTATG GAAGGCGACT GTTTTATTTA TAAAATTCGC TTTGATGGAA CTAACTTCCC CCCGAACGGC
    CCTGTAATGC
398 AAAAGAAGAC CTTAAAATGG GAACCTAGCA CCGAAAAAAT GTATGTACGC GACGGAGTTC TTAAGGGTGA CGTAAACATG GCACTTCTGC
    TCGAAGGAGG
498 TGGACACTAC CGCTGCGATT TTAAAACCAC TTATAAAGCC AAAAAAGATG TTCGTCTTCC AGATGCACAC AAGGTGGACC ACCGCATTGA
    AATCCTGAGC
598 CACGATAAAG ATTATAATAA AGTTAAACTC TATGAACACG CCGAAGCCCG CTATTCTATG TTACCGTCTC AGGCTAAAGC TAGC
``` eCGP2 [SEQ ID NO: 2]
```
  1 ATGTCAG TAATTAAACC GGAAATGAAA ATTAAATTGC GTTTGGAAGG TGCCGTTAAC GGCCATGAAT TTGTAATTGA AGGAGAAGGA
    AAAGGCAAAC
 98 CATTCGAAGG AACCCAGACC CTGGATTTAA CCGTAAAAGA AGGCGCACCT CTCCCTTTCG CGTACGACAT CCTCACCCCA GCCTTCCAAT
    ACGGCAATCG
198 CGCTTTCGCC AAATACCCAA AAGATATTCC AGACTATTTT AAACAAACAT TCCCCGAAGG CTATTCTTGG AACGCTCTA TGACCTATGA
    AGATCAAGGA
298 ATTTGTATCG CTACCTCCGA CATTACTATG GAAGGAGACT GTTTTTTTTA TAAAATTCGC TTTGATGGAA CTAACTTCCC CCCGAACGGC
    CCTGTAATGC
398 AAAAGAAGAC CTTAAAATGG GAACCTAGCA CCGAAAAAAT GTATGTACGC GACGGAGTTC TTAAGGGTGA CGTAAACATG GCACTTCTGC
    TCGAAGGAGG
498 TGGACACTAC CGCTGCGATT TTAAAACCAC TTATAAAGCC AAAAAAGATG TTCGTCTTCC AGATGCACAC AAGGTGGACC ACCGCATTGA
    AATCCTGAGC
598 CACGATAAAG ATTATAATAA AGTTAAACTC TATGAACACG CCGAAGCCCG CTATTCTATG TTACCGTCTC AGGCTAAAGC TAGC
``` eCGP13 [SEQ ID NO: 3]
```
  1 ATGTCAG TAATTAAACC GGAAATGAAA ATTAAATTGC GTATGGAAGG TGCCGTTAAC GGCCATAAAT TTGTAATTGA AGGGGAAGGA
    AAAGGCAACC
 98 CATTCGAAGG AACCCAGACC CTGGATTTAA CCGTAAAGGA AGGCGCACCT CTCCCTTTCG CGTACGACAT CCTCACCCCA GTCTTCCAAT
    ACGGCAATCG
198 CGCTTTCACC AAATACCCAC AAGATATTCC AGACTATTTT AAACAAACAT TCCCCGAAGG CTATTCTTGG AACGCTCTA TGACCTATGA
    AGATCATGGA
298 ATTTGTATCG CTACCTCCGA CATTACTATG GAAGGCGACT GTTTTATTTA TAAAATTCGC TTTGATGGAA CTAACTTCCC CCCAAACGGC
    CCTGTAATGC
398 AAAAGAAGAC CTTAAAATGG GAACCTAGCA CCGAAAAAAT GTATGTACGC GACGGAGTTC TTAAGGGTGA CGTAAACATG GCACTTCTGC
    TCGAAGGAGG
498 TGGACACTAC CGCTGCGATT TTAAAACCAC TTATAAAGCC AAAAAAGATG TTCGTCTTCC AGGTGCACAC AAGGTGGACC ACCGCATTGA
    AATCCTGAGC
598 CACGATAAAG ATTATAATAA AGTTAAACTC TATGAACACG CCGAAGCCCG CTATTCTATG TTACCGTCTC AGGCTAAAGC TAGC
``` eCGP23 [SEQ ID NO: 4]
```
  1 ATGTCAG TAATTAAACC GGAAATGAAA ATTAAATTGC GTTTGGAAGG TGCCGTTAAC GGCCATGAAT TTGTAATTGA AGGAGAAGGA
    AAAGGCAAAC
 98 CATTCGAAGG AACCCAGACC CTGGATTTAA CCGTAAAAGA AGGCGCACCT CTCCCTTTCG CGTACGACAT CCTCACCCCA GCCTTCCAAT
    ACGGCAATCG
198 CGCTTTCACC AAATACCCAA AAGATATTCC AGACTATTTT AAACAAACAT TCCCCGAAGG CTATTCTTGG AACGCTCTA TGACCTATGA
    AGATCAAGGA
298 ATTTGTATCG CTACCTCCGA CATTACTATG GAAGGAGACT GTTTTTTTTA TAAGATTCGC TTTGATGGAA CTAACTTCCC CCCGAACGGC
    CCTGTAATGC
398 AAAAGAAGAC CTTAAAATGG GAACCTAGCA CCGAAAAAAT GTATGTACGC GACGGAGTTC TTAAGGGTGA CGTAAACATG GCACTTCTGC
    TCGAAGGAGG
498 TGGACACTAC CGCTGCGATT TTAAAACCAC TTATAAAGCC AAAAAAGATG TTCGTCTTCC AGATGCACAC GAGGTGGACC ACCGCATTGA
    AATCCTGAGC
598 CACGATAAAG ATTATAATAA AGTTAAACTC TATGAACACG CCGAAGCCCG CTATTCTATG TTACCGTCTC AGGCTAAAGC TAGC
``` eCGP123 [SEQ ID NO: 5]
```
  1 ATGTCAG TAATTAAACC GGAAATGAAA ATTAAATTGC GTATGGAAGG TGCCGTTAAC GGCCATAAAT TTGTAATTGA AGGAGAAGGA
    ATAGGCAAAC
 98 CATACGAAGG AACCCAGACC CTGGATTTAA CCGTAAAAGA AGGCGCACCT CTCCCTTTCT CGTACGACAT CCTCACCCCA GCCTTCCAAT
    ACGGCAATCG
198 CGCTTTCACC AAATACCCAA AAGATATTCC AGACTATTTT AAACAAGCAT TCCCCGAAGG CTATTCTTGG AACGCTCTA TGACCTATGA
    AGATCAAGGA
298 ATTTGTATCG CTACCTCCGA CATTACTATG GAAGGAGACT GTTTTTTTTA TAAGATTCGC TTTGATGGAA CTAACTTCCC CCCGAACGGC
    CCTGTAATGC
398 AAAAGAAGAC CTTAAAATGG GAACCTAGCA CCGAAAAAAT GTATGTACGC GACGGAGTTC TTAAGGGTGA CGTAAACATG GCACTTCTGC
    TCGAAGGAGG
498 TGGACACTAC CGCTGCGATT TTAAAACCAC TTATAAAGCC AAAAAAGATG TTCGTCTTCC AGATGCACAC GAGGTGGACC ACCGCATTGA
    AATCCTGAGC
598 CACGATAAAG ATTATAATAA AGTTAGACTC TATGAACACG CCGAAGCCCG CTATTCTATG TTACCGTCTC AGGCTAAAGC TAGC
```

TABLE OF DNA AND PROTEIN SEQUENCES

-continued eCGP Amino Acid Sequences:

eCGP1 [SEQ ID NO: 6]
MSVIKPEMKIKLRMEGAVNGHKFVIEGEGKGNPFEGTQTLDLTVKEGAPLPFAYDILTPVFQYGNRAFAKYPQDIPDYFKQTFPEGYSWERSMTYEDHGICIA
TSDITMEGDCFIYKIRFDGTNFPPNGPVMQKKTLKWEPSTEKMYVRDGVLKGDVNMALLLEGGGHYRCDFKTTYKAKKDVRLPDAHKVDHRIEILSHDKDYNK
VKLYEHAEARYSMLPSQAK eCGP2 [SEQ ID NO: 7]
MSVIKPEMKIKLRLEQAVNGHEFVIEGEGKGKPFEGTQTLDLTVKEGAPLPFAYDILTPAFQYGNRAFAKYPKDIPDYFKQTFPEGYSWERSMTYEDQGICIA
TSDITMEGDCFFYKIRFDGTNFPPNGPVMQKKTLKWEPSTEKMYVRDGVLKGDVNMALLLEGGGHYRCDFKTTYKAKKDVRLPDAHKVDHRIEILSHDKDYNK
VKLYEHAEARYSMLPSQAK eCGP13 [SEQ ID NO: 8]
MSVIKPEMKIKLRMEGAVNGHKFVIEGEGKGNPFEGTQTLDLTVKEGAPLPFAYDILTPVFQYGNRAFTKYPQDIPDYFKQTFPEGYSWERSMTYEDHGICIA
TSDITMEGDCFIYKIRFDGTNFPPNGPVMQKKTLKWEPSTEKMYVRDGVLKGDVNMALLLEGGGHYRCDFKTTYKAKKDVRLPGAHKVDHRIEILSHDKDYNK
VKLYEHAEARYSMLPSQAK eCGP23 [SEQ ID NO: 9]
MSVIKPEMKIKLRLEGAVNGHEFVIEGEGKGKPFEGTQTLDLTVKEGAPLPFAYDILTPAFQYGNRAFTKYPKDIPDYFKQTFPEGYSWERSMTYEDQGICIA
TSDITMEGDCFFYKIRFDGTNFPPNGPVMQKKTLKWEPSTEKMYVRDGVLKGDVNMALLLEGGGHYRCDFKTTYKAKKDVRLPDAHEVDHRIEILSHDKDYNK
VKLYEHAEARYSMLPSQAK eCGP123 [SEQ ID NO: 10]
MSVIKPEMKIKLRMEGAVNGHKFVIEGEGIGKPYEGTQTLDLTVKEGAPLPFSYDILTPAFQYGNRAFTKYPKDIPDYFKQAFPEGYSWERSMTYEDQGICIA
TSDITMEGDCFFYKIRFDGTNFPPNGPVMQKKTLKWEPSTEKMYVRDGVLKGDVNMALLLEGGGHYRCDFKTTYKAKKDVRLPDAHEVDHRIEILSHDKDYNK
VRLYEHAEARYSMLPSQAK

LITERATURE CITED BY SUPERSCRIPT FOOTNOTES

1. Zacchi, P., Sblattero, D., Florian, F., Marzari, R. & Bradbury, A. R. (2003). Selecting open reading frames from DNA. *Genome Res* 13, 980-90.
2. Maxwell, K. L., Mittermaier, A. K., Forman-Kay, J. D. & Davidson, A. R. (1999). A simple in vivo assay for increased protein solubility. *Protein Sci.* 8, 1908-11.
3. Lutz, S., Fast, W. & Benkovic, S. J. (2002). A universal, vector-based system for nucleic acid reading-frame selection. *Protein Eng* 15, 1025-30.
4. Fisher, A. C., Kim, W. & DeLisa, M. P. (2006). Genetic selection for protein solubility enabled by the folding quality control feature of the twin-arginine translocation pathway. *Protein Sci* 15, 449-58.
5. Nakayama, M. & Ohara, O. (2003). A system using convertible vectors for screening soluble recombinant proteins produced in *Escherichia coli* from randomly fragmented cDNAs. *Biochem Biophys Res Commun* 312, 825-30.
6. Liu, J. W., Boucher, Y., Stokes, H. W. & Ollis, D. L. (2006). Improving protein solubility: the use of the *Escherichia coli* dihydrofolate reductase gene as a fusion reporter. *Protein Expr Purif* 47, 258-63.
7. Waldo, G. S., Standish, B. M., Berendzen, J. & Terwilliger, T. C. (1999). Rapid protein-folding assay using green fluorescent protein. *Nat. Biotechnol.* 17, 691-5.
8. Wigley, W. C., Stidham, R. D., Smith, N. M., Hunt, J. F. & Thomas, P. J. (2001). Protein solubility and folding monitored in vivo by structural complementation of a genetic marker protein. *Nat Biotechnol* 19, 131-6.
9. Pedelacq, J. D., Piltch, E., Liong, E. C., Berendzen, J., Kim, C. Y., Rho, B. S., Park, M. S., Terwilliger, T. C. & Waldo, G. S. (2002). Engineering soluble proteins for structural genomics. *Nat Biotechnol* 20, 927-32.
10. Arnold, F. H., Giver, L., Gershenson, A., Zhao, H. & Miyazaki, K. (1999). Directed evolution of mesophilic enzymes into their thermophilic counterparts. *Ann N Y Acad Sci* 870, 400-3.
11. Giver, L., Gershenson, A., Freskgard, P. O. & Arnold, F. H. (1998). Directed evolution of a thermostable esterase. *Proc Natl Acad Sci USA* 95, 12809-13.
12. Palackal, N., Brennan, Y., Callen, W. N., Dupree, P., Frey, G., Goubet, F., Hazlewood, G. P., Healey, S., Kang, Y. E., Kretz, K. A., Lee, E., Tan, X., Tomlinson, G. L., Verruto, J., Wong, V. W., Mathur, E. J., Short, J. M., Robertson, D. E. & Steer, B. A. (2004). An evolutionary route to xylanase process fitness. *Protein Sci* 13, 494-503.
13. Fridjonsson, O., Watzlawick, H. & Mattes, R. (2002). Thermoadaptation of alpha-galactosidase AgaB1 in *Thermus thermophilus*. *J Bacteriol* 184, 3385-91.
14. Nakamura, A., Takakura, Y., Kobayashi, H. & Hoshino, T. (2005). In vivo directed evolution for thermostabilization of *Escherichia coli* hygromycin B phosphotransferase and the use of the gene as a selection marker in the host-vector system of *Thermus thermophilus*. *J Biosci Bioeng* 100, 158-63.
15. Sieber, V., Pluckthun, A. & Schmid, F. X. (1998). Selecting proteins with improved stability by a phage-based method. *Nat Biotechnol* 16, 955-60.
16. Kristensen, P. & Winter, G. (1998). Proteolytic selection for protein folding using filamentous bacteriophages. *Fold Des* 3, 321-8.
17. Wunderlich, M. & Schmid, F. X. (2006). In vitro evolution of a hyperstable Gbeta1 variant. *J Mol Biol* 363, 545-57.
18. Wunderlich, M., Martin, A., Staab, C. A. & Schmid, F. X. (2005). Evolutionary protein stabilization in comparison with computational design. *J Mol Biol* 351, 1160-8.
19. Wunderlich, M., Martin, A. & Schmid, F. X. (2005). Stabilization of the cold shock protein CspB from *Bacillus subtilis* by evolutionary optimization of Coulombic interactions. *J Mol Biol* 347, 1063-76.
20. Martin, A., Schmid, F. X. & Sieber, V. (2003). Proside: a phage-based method for selecting thermostable proteins. *Methods Mol Biol* 230, 57-70.
21. Martin, A. & Schmid, F. X. (2003). Evolutionary stabilization of the gene-3-protein of phage fd reveals the principles that govern the thermodynamic stability of two-domain proteins. *J Mol Biol* 328, 863-75.
22. Martin, A., Sieber, V. & Schmid, F. X. (2001). In-vitro selection of highly stabilized protein variants with optimized surface. *J Mol Biol* 309, 717-26.
23. Shusta, E. V., Kieke, M. C., Parke, E., Kranz, D. M. & Wittrup, K. D. (1999). Yeast polypeptide fusion surface display levels predict thermal stability and soluble secretion efficiency. *J. Mol. Biol.* 292, 949-56.
24. Park, S., Xu, Y., Stowell, X. F., Gai, F., Saven, J. G. & Boder, E. T. (2006). Limitations of yeast surface display in engineering proteins of high thermostability. *Protein Eng Des Sel* 19, 211-7.
25. Steipe, B. (2004). Consensus-based engineering of protein stability: from intrabodies to thermostable enzymes. *Methods Enzymol* 388, 176-86.
26. Steipe, B., Schiller, B., Pluckthun, A. & Steinbacher, S. (1994). Sequence statistics reliably predict stabilizing mutations in a protein domain. *J. Mol. Biol.* 240, 188-92.
27. Ohage, E. & Steipe, B. (1999). Intrabody construction and expression. I. The critical role of VL domain stability. *J. Mol. Biol.* 291, 1119-28.
28. Wirtz, P. & Steipe, B. (1999). Intrabody construction and expression III: engineering hyperstable V(H) domains. *Protein Sci.* 8, 2245-50.
29. Visintin, M., Settanni, G., Maritan, A., Graziosi, S., Marks, J. D. & Cattaneo, A. (2002). The intracellular antibody capture technology (IACT): towards a consensus sequence for intracellular antibodies. *J. Mol. Biol.* 317, 73-83.
30. Knappik, A., Ge, L., Honegger, A., Pack, P., Fischer, M., Wellnhofer, G., Hoess, A., Wolle, J., Pluckthun, A. & Virnekas, B. (2000). Fully synthetic human combinatorial antibody libraries (HuCAL) based on modular consensus frameworks and CDRs randomized with trinucleotides. *J. Mol. Biol.* 296, 57-86.
31. Arndt, M. A., Krauss, J., Schwarzenbacher, R., Vu, B. K., Greene, S. & Rybak, S. M. (2003). Generation of a highly stable, internalizing anti-CD22 single-chain Fv fragment for targeting non-Hodgkin's lymphoma. *Int J Cancer* 107, 822-9.
32. McDonagh, C. F., Beam, K. S., Wu, G. J., Chen, J. H., Chace, D. F., Senter, P. D. & Francisco, J. A. (2003). Improved yield and stability of L49-sFv-beta-lactamase, a single-chain antibody fusion protein for anticancer prodrug activation, by protein engineering. *Bioconjug Chem* 14, 860-9.
33. Whitcomb, E. A., Martin, T. M. & Rittenberg, M. B. (2003). Restoration of Ig secretion: mutation of germline-encoded residues in T15L chains leads to secretion of free light chains and assembled antibody complexes bearing secretion-impaired heavy chains. *J Immunol* 170, 1903-9.
34. Demarest, S. J., Rogers, J. & Hansen, G. (2004). Optimization of the antibody C(H)₃ domain by residue frequency analysis of IgG sequences. *J Mol Biol* 335, 41-8.
35. Wang, Q., Buckle, A. M. & Fersht, A. R. (2000). Stabilization of GroEL minichaperones by core and surface mutations. *J Mol Biol* 298, 917-26.
36. Wang, Q., Buckle, A. M., Foster, N. W., Johnson, C. M. & Fersht, A. R. (1999). Design of highly stable functional GroEL minichaperones. *Protein Sci* 8, 2186-93.
37. Nikolova, P. V., Henckel, J., Lane, D. P. & Fersht, A. R. (1998). Semirational design of active tumor suppressor p53 DNA binding domain with enhanced stability. *Proc Natl Acad Sci USA* 95, 14675-80.
38. Jiang, X., Kowalski, J. & Kelly, J. W. (2001). Increasing protein stability using a rational approach combining sequence homology and structural alignment: Stabilizing the WW domain. *Protein Sci* 10, 1454-65.
39. Maxwell, K. L. & Davidson, A. R. (1998). Mutagenesis of a buried polar interaction in an SH3 domain: sequence conservation provides the best prediction of stability effects. *Biochemistry* 37, 16172-82.
40. Lehmann, M., Loch, C., Middendorf, A., Studer, D., Lassen, S. F., Pasamontes, L., van Loon, A. P. & Wyss, M. (2002). The consensus concept for thermostability engineering of proteins: further proof of concept. *Protein Eng* 15, 403-11.
41. Lehmann, M. & Wyss, M. (2001). Engineering proteins for thermostability: the use of sequence alignments versus rational design and directed evolution. *Curr Opin Biotechnol* 12, 371-5.
42. Lehmann, M., Pasamontes, L., Lassen, S. F. & Wyss, M. (2000). The consensus concept for thermostability engineering of proteins. *Biochim Biophys Acta* 1543, 408-415.
43. Lehmann, M., Kostrewa, D., Wyss, M., Brugger, R., D'Arcy, A., Pasamontes, L. & van Loon, A. P. (2000). From DNA sequence to improved functionality: using protein sequence comparisons to rapidly design a thermostable consensus phytase. *Protein Eng* 13, 49-57.
44. Devi, V. S., Binz, H. K., Stumpp, M. T., Pluckthun, A., Bosshard, H. R. & Jelesarov, I. (2004). Folding of a designed simple ankyrin repeat protein. *Protein Sci* 13, 2864-70.
45. Kohl, A., Binz, H. K., Forrer, P., Stumpp, M. T., Pluckthun, A. & Grutter, M. G. (2003). Designed to be stable: Crystal structure of a consensus ankyrin repeat protein. *Proc Natl Acad Sci USA* 100, 1700-5.
46. Main, E. R., Jackson, S. E. & Regan, L. (2003). The folding and design of repeat proteins: reaching a consensus. *Curr Opin Struct Biol* 13, 482-9.
47. Dai, M., Fisher, H. E., Temirov, J., Kiss, C., Phipps, M. E., Pavlik, P., Werner, J. H. & Bradbury, A. R. (2007). The creation of a novel fluorescent protein by guided consensus engineering. *Protein Eng Des Sel* 20, 69-79.
48. Karasawa, S., Araki, T., Yamamoto-Hino, M. & Miyawaki, A. (2003). A green-emitting fluorescent protein from Galaxeidae coral and its monomeric version for use in fluorescent labeling. *J Biol Chem* 278, 34167-71.
49. Serrano, L. & Fersht, A. R. (1989). Capping and alpha-helix stability. *Nature* 342, 296-9.
50. Sali, D., Bycroft, M. & Fersht, A. R. (1988). Stabilization of protein structure by interaction of alpha-helix dipole with a charged side chain. *Nature* 335, 740-3.
51. Nicholson, H., Becktel, W. J. & Matthews, B. W. (1988). Enhanced protein thermostability from designed mutations that interact with alpha-helix dipoles. *Nature* 336, 651-6.
52. Nicholson, H., Anderson, D. E., Dao-pin, S. & Matthews, B. W. (1991). Analysis of the interaction between charged side chains and the alpha-helix dipole using designed thermostable mutants of phage T4 lysozyme. *Biochemistry* 30, 9816-28.
53. Blaber, M., Zhang, X. J. & Matthews, B. W. (1993). Structural basis of amino acid alpha helix propensity. *Science* 260, 1637-40.
54. Serrano, L., Sancho, J., Hirshberg, M. & Fersht, A. R. (1992). Alpha-helix stability in proteins. I. Empirical correlations concerning substitution of side-chains at the N and C-caps and the replacement of alanine by glycine or serine at solvent-exposed surfaces. *J Mol Biol* 227, 544-59.

55. Serrano, L., Neira, J. L., Sancho, J. & Fersht, A. R. (1992). Effect of alanine versus glycine in alpha-helices on protein stability. *Nature* 356, 453-5.
56. Schwehm, J. M., Fitch, C. A., Dang, B. N., Garcia-Moreno, E. B. & Stites, W. E. (2003). Changes in stability upon charge reversal and neutralization substitution in staphylococcal nuclease are dominated by favorable electrostatic effects. *Biochemistry* 42, 1118-28.
57. Makhatadze, G. I., Loladze, V. V., Ermolenko, D. N., Chen, X. & Thomas, S. T. (2003). Contribution of surface salt bridges to protein stability: guidelines for protein engineering. *J Mol Biol* 327, 1135-48.
58. Pace, C. N., Alston, R. W. & Shaw, K. L. (2000). Charge-charge interactions influence the denatured state ensemble and contribute to protein stability. *Protein Sci* 9, 1395-8.
59. Strop, P. & Mayo, S. L. (2000). Contribution of surface salt bridges to protein stability. *Biochemistry* 39, 1251-5.
60. Waldburger, C. D., Schildbach, J. F. & Sauer, R. T. (1995). Are buried salt bridges important for protein stability and conformational specificity? *Nat Struct Biol* 2, 122-8.
61. Dao-pin, S., Nicholson, H., Baase, W. A., Zhang, X. J., Wozniak, J. A. & Matthews, B. W. (1991). Structural and genetic analysis of electrostatic and other interactions in bacteriophage T4 lysozyme. *Ciba Found Symp* 161, 52-62.
62. Serrano, L., Horovitz, A., Avron, B., Bycroft, M. & Fersht, A. R. (1990). Estimating the contribution of engineered surface electrostatic interactions to protein stability by using double-mutant cycles. *Biochemistry* 29, 9343-52.
63. Anderson, D. E., Hurley, J. H., Nicholson, H., Baase, W. A. & Matthews, B. W. (1993). Hydrophobic core repacking and aromatic-aromatic interaction in the thermostable mutant of T4 lysozyme Ser 117→Phe. *Protein Sci* 2, 1285-90.
64. Serrano, L., Bycroft, M. & Fersht, A. R. (1991). Aromatic-aromatic interactions and protein stability. Investigation by double-mutant cycles. *J Mol Biol* 218, 465-75.
65. Burley, S. K. & Petsko, G. A. (1985). Aromatic-aromatic interaction: a mechanism of protein structure stabilization. *Science* 229, 23-8.
66. Matsumura, M., Signor, G. & Matthews, B. W. (1989). Substantial increase of protein stability by multiple disulphide bonds. *Nature* 342, 291-3.
67. Matthews, B. W., Nicholson, H. & Becktel, W. J. (1987). Enhanced protein thermostability from site-directed mutations that decrease the entropy of unfolding. *Proc Natl Acad Sci USA* 84, 6663-7.
68. Clarke, J. & Fersht, A. R. (1993). Engineered disulfide bonds as probes of the folding pathway of barnase: increasing the stability of proteins against the rate of denaturation. *Biochemistry* 32, 4322-9.
69. Eijsink, V. G., Bjork, A., Gaseidnes, S., Sirevag, R., Synstad, B., van den Burg, B. & Vriend, G. (2004). Rational engineering of enzyme stability. *J Biotechnol* 113, 105-20.
70. Heinis, C., Alessi, P. & Neri, D. (2004). Engineering a thermostable human prolyl endopeptidase for antibody-directed enzyme prodrug therapy. *Biochemistry* 43, 6293-303.
71. Willuda, J., Honegger, A., Waibel, R., Schubiger, P. A., Stahel, R., Zangemeister-Wittke, U. & Pluckthun, A. (1999). High thermal stability is essential for tumor targeting of antibody fragments: engineering of a humanized anti-epithelial glycoprotein-2 (epithelial cell adhesion molecule) single-chain Fv fragment. *Cancer Res* 59, 5758-67.
72. Binz, H. K., Amstutz, P., Kohl, A., Stumpp, M. T., Briand, C., Forrer, P., Grutter, M. G. & Pluckthun, A. (2004). High-affinity binders selected from designed ankyrin repeat protein libraries. *Nat Biotechnol* 22, 575-82.
73. Bloom, J. D., Labthavikul, S. T., Otey, C. R. & Arnold, F. H. (2006). Protein stability promotes evolvability. *Proc Natl Acad Sci USA* 103, 5869-74.
74. Pedelacq, J. D., Cabantous, S., Tran, T., Terwilliger, T. C. & Waldo, G. S. (2006). Engineering and characterization of a superfolder green fluorescent protein. *Nat Biotechnol* 24, 79-88.
75. Wilmann, P. G., Turcic, K., Battad, J. M., Wilce, M. C., Devenish, R. J., Prescott, M. & Rossjohn, J. (2006). The 1.7 A crystal structure of Dronpa: a photoswitchable green fluorescent protein. *J Mol Biol* 364, 213-24.
76. Waldo, G. S. (2004). Directed evolution methods for improving polypeptide folding and solubility and superfolder fluorescent proteins generated thereby (USPTO, ed.). Los Alamos National Laboratory, US.
77. Lefranc, M. P., Pommie, C., Kaas, Q., Duprat, E., Bosc, N., Guiraudou, D., Jean, C., Ruiz, M., Da Piedade, I., Rouard, M., Foulquier, E., Thouvenin, V. & Lefranc, G. (2005). IMGT unique numbering for immunoglobulin and T cell receptor constant domains and Ig superfamily C-like domains. *Dev Comp Immunol* 29, 185-203.
78. Jespers, L., Jenne, S., Lasters, I. & Collen, D. (1997). Epitope mapping by negative selection of randomized antigen libraries displayed on filamentous phage. *J. Mol. Biol.* 269, 704-18.
79. Pannekoek, H., van Meijer, M., Schleef, R. R., Loskutoff, D. J. & Barbas, C. d. (1993). Functional display of human plasminogen-activator inhibitor 1 (PAI-1) on phages: novel perspectives for structure-function analysis by error-prone DNA synthesis. *Gene* 128, 135-40.
80. van Meijer, M., Roelofs, Y., Neels, J., Horrevoets, A., van Zonneveld, A. & Pannekoek, H. (1996). Selective screening of a large phage display library of plasminogen activator inhibitor 1 mutants to localize interaction sites with either thrombin or the variable region 1 of tissue-type plasminogen activator. *J. Biol. Chem.* 271, 7423-7428.
81. Oliphant, T., Engle, M., Nybakken, G. E., Doane, C., Johnson, S., Huang, L., Gorlatov, S., Mehlhop, E., Marri, A., Chung, K. M., Ebel, G. D., Kramer, L. D., Fremont, D. H. & Diamond, M. S. (2005). Development of a humanized monoclonal antibody with therapeutic potential against West Nile virus. *Nat Med* 11, 522-30.
82. Levy, R., Forsyth, C. M., LaPorte, S. L., Geren, I. N., Smith, L. A. & Marks, J. D. (2007). Fine and domain-level epitope mapping of botulinum neurotoxin type A neutralizing antibodies by yeast surface display. *J Mol Biol* 365, 196-210.
83. Chao, G., Cochran, J. R. & Wittrup, K. D. (2004). Fine epitope mapping of anti-epidermal growth factor receptor antibodies through random mutagenesis and yeast surface display. *J Mol Biol* 342, 539-50.
84. Johns, T. G., Adams, T. E., Cochran, J. R., Hall, N. E., Hoyne, P. A., Olsen, M. J., Kim, Y. S., Rothacker, J., Nice, E. C., Walker, F., Ritter, G., Jungbluth, A. A., Old, L. J., Ward, C. W., Burgess, A. W., Wittrup, K. D. & Scott, A. M. (2004). Identification of the epitope for the epidermal growth factor receptor-specific monoclonal reveals that it preferentially recognizes an untethered form of the receptor. *J Biol Chem* 279, 30375-84. antibody 806

What is claimed is:

1. A method of generating a polynucleotide encoding an enhanced folding variant of a cyan fluorescent protein, comprising:
   (a) providing a polynucleotide encoding a fusion protein comprising a heterologous folding interference domain inserted into a permissive site of a cyan fluorescent protein, wherein
      the cyan fluorescent protein consists of the amino acid sequence set forth as SEQ ID NO: 27; and
      the heterologous folding interference domain consists of the amino acid sequence set forth as SEQ ID NO: 26 and is inserted between residues 18 and 19 of the cyan fluorescent protein in the fusion protein;
      the amino acid sequence of the fusion protein comprises, from N- to C-terminus, residues 1-18 of SEQ ID NO: 27, SEQ ID NO: 26, and residues 19-225 of SEQ ID NO: 27;
   (b) providing a library of test polynucleotides encoding mutants of (a), wherein the library of test polynucleotides is obtained from the polynucleotide of (a) mutagenized by error-prone PCR mutagenesis;
   (c) expressing the library of test polynucleotides to produce the mutants of the fusion protein;
   (d) assaying fluorescence of the mutants of the fusion protein;
   (e) selecting from the library a test polynucleotide encoding a mutant of the fusion protein with increased fluorescence compared to the fluorescence of the fusion protein; and
   (f) removing the polynucleotide encoding the heterologous folding interference domain from the selected test polynucleotide of step (e) to generate a polynucleotide encoding an enhanced folding variant of the cyan fluorescent protein.

2. The method of claim 1, further comprising:
   (g) inserting a polynucleotide encoding a second heterologous folding interference domain into the test polynucleotide selected in step (e) to generate a polynucleotide encoding a second fusion protein, wherein the second heterologous folding interference domain consists of the amino acid sequence set forth as SEQ ID NO: 26 and is inserted between residues 96 and 97 of the cyan fluorescent protein in the second fusion protein;
   (h) providing a second library of test polynucleotides encoding mutants of (g), wherein the second library of test polynucleotides is obtained from the polynucleotide of (g) mutagenized by error-prone PCR mutagenesis;
   (i) expressing the second library of test polynucleotides to produce the mutants of the second fusion protein;
   (j) assaying fluorescence of the mutants of the second fusion proteins;
   (k) selecting from the second library a test polynucleotide encoding a mutant of the second fusion protein with increased fluorescence compared to the fluorescence of the second fusion protein; and
   (l) removing the polynucleotides encoding the heterologous folding interference domains from the selected test polynucleotide of step (k) to generate a second polynucleotide encoding an enhanced folding variant of the cyan fluorescent protein.

3. The method of claim 2, further comprising:
   (m) inserting a polynucleotide encoding a third heterologous folding interference domain into the test polynucleotide selected in step (k) to generate a polynucleotide encoding a third fusion protein, wherein the third heterologous folding interference domain consists of the amino acid sequence set forth as SEQ ID NO: 26 and is inserted between residues 164 and 165 of the cyan fluorescent protein of the third fusion protein;
   (n) providing a third library of test polynucleotides encoding mutants of (m), wherein the third library of test polynucleotides is obtained from the polynucleotide of (m) mutagenized by error-prone PCR mutagenesis;
   (o) expressing the third library of test polynucleotides to produce the mutants of the third fusion protein;
   (p) assaying fluorescence of the mutants of the third fusion proteins;
   (q) selecting from the third library a test polynucleotide encoding a mutant of the third fusion protein with increased fluorescence compared to the fluorescence of the third fusion protein; and
   (r) removing the polynucleotides encoding the heterologous folding interference domains from the selected test polynucleotide of step (q) to generate a third polynucleotide encoding an enhanced folding variant of the cyan fluorescent protein.

* * * * *